US012773464B2

(12) United States Patent
Sohn

(10) Patent No.: US 12,773,464 B2
(45) Date of Patent: Oct. 27, 2026

(54) SELECTIVE LIGANDS FOR TAU AGGREGATES

(71) Applicant: Sentonix, Inc., Arlington, MA (US)

(72) Inventor: Daniel Dungan Sohn, Stockholm (SE)

(73) Assignee: Sentonix, Inc., Arlington, MA (US)

( * ) Notice: Subject to any disclaimer, the term of this patent is extended or adjusted under 35 U.S.C. 154(b) by 1210 days.

(21) Appl. No.: 17/768,660

(22) PCT Filed: Oct. 15, 2020

(86) PCT No.: PCT/EP2020/079139
§ 371 (c)(1),
(2) Date: Apr. 13, 2022

(87) PCT Pub. No.: WO2021/074351
PCT Pub. Date: Apr. 22, 2021

(65) Prior Publication Data

US 2024/0165276 A1 May 23, 2024

(30) Foreign Application Priority Data

Oct. 16, 2019 (GB) ...................................... 1914989

(51) Int. Cl.

| | |
|---|---|
| ***A61P 25/28*** | (2006.01) |
| ***A61K 51/04*** | (2006.01) |
| ***C07D 401/14*** | (2006.01) |
| ***C07D 417/14*** | (2006.01) |

(52) U.S. Cl.
CPC .......... *A61K 51/0455* (2013.01); *A61P 25/28* (2018.01); *C07D 401/14* (2013.01); *C07D 417/14* (2013.01)

(58) Field of Classification Search
CPC ... A61K 51/0455; A61P 25/28; C07D 401/14; C07D 417/14
See application file for complete search history.

(56) References Cited

U.S. PATENT DOCUMENTS

| | | | | |
|---|---|---|---|---|
| 12,304,901 | B2 | 5/2025 | Sohn | |
| 2012/0302755 | A1 | 11/2012 | Szardenings et al. | |
| 2015/0374662 | A1* | 12/2015 | Bode | A61K 31/454 435/375 |
| 2021/0138092 | A1 | 5/2021 | Sohn | |

FOREIGN PATENT DOCUMENTS

| | | | | |
|---|---|---|---|---|
| DE | 3722992 | A1 | 1/1989 | |
| WO | WO-2006044503 | A2 | 4/2006 | |
| WO | WO-2006080821 | A1 | 8/2006 | |
| WO | WO-2007009236 | A1 * | 1/2007 | A61P 3/04 |
| WO | WO-2007086800 | A1 * | 8/2007 | C07B 59/002 |
| WO | WO-2012001107 | A1 * | 1/2012 | A61P 3/10 |
| WO | 2012164071 | A1 | 12/2012 | |
| WO | WO-2014140592 | A1 | 9/2014 | |
| WO | WO-2015110263 | A1 | 7/2015 | |
| WO | WO-2017009454 | A1 | 1/2017 | |
| WO | 2017/153601 | A1 | 9/2017 | |
| WO | WO-2019025595 | A1 | 2/2019 | |
| WO | 2019/049061 | A1 | 3/2019 | |
| WO | 2019/197502 | A1 | 10/2019 | |
| WO | WO-2019234243 | A1 * | 12/2019 | C07D 513/04 |
| WO | WO-2024094816 | A1 | 5/2024 | |

OTHER PUBLICATIONS

CAS Registry No. 2299229-31-3, entered Registry on Apr. 2, 2019. (Year: 2019).*
CAS Registry No. 1207531-56-3, entered on Mar. 1, 2010. (Year: 2010).*
Database Registry [Online] Chemical Abstracts Service, "XP002791969," accessed on May 21, 2019, 1 page.
Database Registry [Online] Chemical Abstracts Service, "XP002791970," accessed on May 21, 2019, 1 page.
Database Registry [Online] Chemical Abstracts Service, "XP002791971," accessed on May 21, 2019, 1 page.
International Search Report and Written Opinion for International Application No. PCT/EP2019/059165, European Patent Office, Netherlands, mailed on Jul. 10, 2019, 29 pages.
International Search Report and Written Opinion for International Application No. PCT/EP2020/079139, European Patent Office, Netherlands, mailed on Feb. 1, 2021, 16 pages.

(Continued)

*Primary Examiner* — Kamal A Saeed
*Assistant Examiner* — Ashli A Chicks
(74) *Attorney, Agent, or Firm* — Sterne, Kessler, Goldstein & Fox P.L.L.C.

(57) ABSTRACT

The present invention provides a compound of formula (I) and compositions comprising a compound of formula (I) or a pharmaceutically acceptable salt, ester, amide or carbamate thereof, or a salt of such an ester, amide or carbamate. The present invention also provides a compound of formula (X) and compositions comprising a compound of formula (X) or a pharmaceutically acceptable salt, ester, amide or carbamate thereof, or a salt of such an ester, amide or carbamate. The present invention further provides uses of the compounds of formula (I) and (X) and compositions comprising compounds of formula (I) and (X), including the use of such compounds and compositions for the diagnosis and treatment of neurodegenerative diseases, and especially tauopathies such as Alzheimer's disease.

(I)

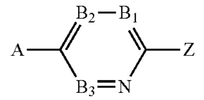

(X)

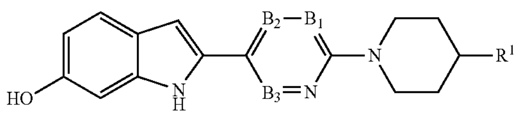

22 Claims, No Drawings

(56) References Cited

OTHER PUBLICATIONS

Morozova, O.A., "Conformational features of tau fibrils from Alzheimer's disease brain are faithfully propagated by unmodified recombinant protein," Biochemistry 52(40):6960-6967, ACS Publications, United States (Oct. 2013).
Mullard, A., "Pharma pumps up anti-tau Alzheimer pipeline despite first Phase III failure," Nature Reviews Drug Discovery 15(9):591-592, Nature Portfolio, Germany (Aug. 2016).
United Kingdom Search for GB Application No. 1806004.6, United Kingdom Intellectual Property Office, United Kingdom, mailed on Dec. 10, 2018, 5 pages.
Written Opinion for International Application No. PCT/EP2023/080605, European Patent Office, Germany, mailed on Oct. 5, 2024, 7 pages.
Co-pending Application, U.S. Appl. No. 19/096,266, inventor Sohn, Daniel. D., filed Mar. 31, 2025 (Not yet Published).
Robert J. Gleave et al., Synthesis and evaluation of 3-amino-6-aryl-pyridazines as selective CB"2 agonists for the treatment of inflammatory pain, Biorganic & Medicinal Chemistry Letters, Jan. 5, 2010 (Jan. 15, 2010), vol. 20, No. 2, pp. 465-468.
Eric D. Hostetler et al., Preclinical Characterization of 18F-MK-6240, a Promising PET Tracer for In Vivo Quantification of Human Neurofibrillary Tangles, J Nucl Med, 2016, 57, pp. 1599-1606.
Masahiro Maruyama et al., Imaging of Tau Pathology in a Tauopathy Mouse Model and in Alzheimer Patients Compared to Normal Controls, Neuron, 2013, 79, pp. 1094-1108.
Arendt, et al., "Tau and tauopathies", Brain Research Bulletin, vol. 126, pp. 238-292, 2016.
Aslund, et al., "Novel Pentameric Thiophene Derivatives for in Vitro and in Vivo Optical Imaging of a Plethora of Protein Aggregates in Cerebral Amyloidoses", ACS Chemical Biology, vol. 4, No. 8, pp. 673-684, 2009.
Biernat, et al., "The switch of tau protein to an Alzheimer-like state includes the phosphorylation of two serine-proline motifs upstream of the microtubule binding region", The EMBO Journal, vol. 11, No. 4, pp. 1593-1597, 1992.
Ballatore, et al., "Tau-mediated neurodegeneration in Alzheimer's disease and related disorders", Nature Reviews Neuroscience, vol. 8, pp. 663-672, Sep. 2007.
Ross, et al., "Protein aggregation and neurodegenerative disease", Nature Medicine, pp. 510-517, Jul. 2004.
Cesura, et al., "Characterization of the Binding of [$^3$H]Ro 41-1049 to the Active Site of Human Monoamine Oxidase-A", Molecular Pharmacology, vol. 37, pp. 358-366, 1989.
Xia, et al., "[$^{18}$F]T807, a novel tau positron emission tomography imaging agent for Alzheimer's disease", Alzheimer's & Dimentia, vol. 9, pp. 666-676, 2013.
Maarouf, et al., "Histopathological and molecular heterogeneity among individuals with dementia associated with Presenilin mutations", Molecular Neurodegeneration, vol. 3, No. 20, pp. 1-18, 2008.
Clavaguera, et al., "Brain homogenates from human tauopathies induce tau inclusions in mouse brain", PNAS, vol. 110, No. 23, pp. 9535-9540, Jun. 2013.
Small, et al., "PET of Brain Amyloid and Tau in Mild Cognitive Impairment", The New England Journal of Medicine, vol. 355, No. 25, pp. 2652-2663, Dec. 21, 2006.
Levine, et al., "Molecular polymorphism of Aβ in Alzheimer's disease", Neurobiology of Aging, vol. 31, pp. 542-548, 2010.
Shirani, et al., "A Palette of Fluorescent Thiophene-Based Ligands for the Identification of Protein Aggregates", Chemistry; A European Journal Communication, vol. 21, pp. 15133-15137, 2015.
Hashimoto, et al., "Radiosynthesis, Photoisomerization, Biodistribution, and Metabolite Analysis of $^{11}$C-PBB3 as a Clinically Useful PET Probe for Imaging of Tau Pathology", The Journal of Nuclear Medicine, vol. 55, No. 9, pp. 1532-1539, Sep. 2014.
Johnson, et al., "AZD:2184: a radioligand for sensitive detection of β-amyloid deposits", Journal of Neurochemistry, vol. 108, pp. 1177-1186, 2009.
Juréus, et al., "Characterization of AZD4694, a novel fluorinated Aβ plaque neuroimaging PET radioligand", Journal of Neurochemistry, vol. 114, pp. 784-794, 2010.
Lu, et al., "Molecular Structure of β-Amyloid Fibrils in Alzheimer's Disease Brain Tissue", Cell, vol. 154, pp. 1257-1268, Sep. 12, 2013.
Nilsson, "Small organic probes as amyloid specific ligands—Past and recent molecular scaffolds", FEBS Letters, vol. 583, pp. 2593-2599, 2009.
Yang, et al., "Brain Amyloid Imaging—FDA Approval of Florbetapir F18 Injection", The New England Journal of Medicine; Perspective, vol. 36, No. 10, pp. 885-887, Sep. 6, 2012.
Li, et al., "Tau-based therapies in neurodegeneration: opportunities and challenges", Nature Reviews; Drug Discovery, vol. 16, pp. 863-883, Dec. 2017.
Bäck, et al., "Anionic Oligothiophenes Compete for Binding of X-34 but not PIB to Recombinant Aβ AMyloid Fibrils and Alzheimer's Disease Brain-Derived Aβ", Biochemistry; A European Journal of Communication, pp. 18335-18338, 2016.
Fodero-Tavoletti, et al., "$^{18}$F-THK523: a novel in vivo tau imaging ligand for Alzheimer's disease", Brain, vol. 134, pp. 1089-1100, 2011.
Murugan, et al., "Cross-interaction of tau PET tracers with monoamine oxidase B: evidence from silico modelling and in vivo imaging", European Journal of Nuclear Medicine and Molecular Imaging, vol. 46, pp. 1369-1382, 2019.
Saint-Aubert, et al., "Tau PET imaging: present and future directions", Molecular Neurodegeneration, vol. 12, No. 19, pp. 1-21, 2017.
Shirani, et al., "Synthesis of Thiophene-Based Optical Ligands that Selectivity Detect Tau Pathology in Alzheimer's Disease", Bioorganic Chemistry; Chemistry A European Journal, vol. 23, pp. 17127-17135, 2017.
Klingstedt, et al., "Synthesis of a library of oligothiophenes and their utilization as fluorescent ligands for spectral assignment of protein aggregates", Organic * Biomolecular Chemistry, vol. 9, pp. 8356-8370, 2011.
Klingstedt, et al., "The Structural Basis for Optimal Performance of Oligothiophene-Based Fluorescent Amyloid Ligands: Conformational Flexibility is Essential for Spectral Assignment of a Diversity of Protein Aggregates", Chemistry; A European Journal, vol. 19, pp. 10179-10192, 2013.
Klingstedt, et al., "Distinct Spacing Between Anionic Groups: An Essential Chemical Determinant for Achieving Thipphene-Based Ligands to Distinguish β-Amyloid or Tau Polymorphic Aggregates", Chemistry; A European Journal, vol. 21, pp. 9072-9082, 2015.
Taghavi, et al., "N'-Benzylidene-Benzohydrazides as Novel and Selective Tau-PHF Ligands", Journal of Alzheimer's Disease, vol. 27, pp. 835-843, 2011.
Tsugeno, et al., "Regions of the Molecule Responsible for Substrate Specificity of Monoamine Oxidase A and B: A Chimeric Enzyme Analysis", J. Biochemistry, vol. 118, pp. 974-980, 1995.
Qiang, et al., "Structural variation in amyloid-β fibrils from Alzheimer's disease clinical subtypes", Nature, vol. 541, pp. 217-231, Jan. 12, 2017.
Klunk, et al., "Imaging Brain Amyloid in Alzheimer's Disease with Pittsburgh Compound-B", Original Article, pp. 306-317, 2004.
Weyler, et al., "Purification and Properties of Mitochondrial Monoamine Oxidase Type A from Human Placenta", The Hournal of Biological Chemistry, vol. 260, No. 24, pp. 13199-13207, 1985.
Kudo, et al., "2-(2-[2-Dimethylaminothiazol-5-yl]Ethenyl)-6-(2-[Fluoro]Ethoxy)Benzoxazole: A Novel PET Agent for In Vivo Detection of Dense Amyloid Plaques in Alzheimer's Disease Patients", PET Agent for Dense Amyloid-β Deposits, pp. 553-562, 2007.
Zhang, et al., "A Highly Selective and Specific PET Tracer for Imaging of Tau Pathologies", Journal of Alzheimer's Disease, vol. 31, pp. 601-612, 2012.
Enamine Advanced HTS Collection Catalogue, Jun. 2019, Compound and with CAS Registry No. 930868-12-5.

(56) References Cited

OTHER PUBLICATIONS

Search Report based on Application No. GB1914989.7 filed Oct. 16, 2019.

* cited by examiner

SELECTIVE LIGANDS FOR TAU AGGREGATES

CROSS REFERENCES TO RELATED APPLICATIONS

This application is a national-stage application under 35 U.S.C. § 371 of International Application No. PCT/EP2020/079139, filed Oct. 15, 2020, which International Application claims benefit of priority to Great British Patent Application No. 1914989.7, filed Oct. 16, 2019.

FIELD OF THE INVENTION

The present invention relates to compounds of formula (I) and compositions comprising compounds of formula (I). The present invention also relates to compounds of formula (X) and compositions comprising compounds of formula (X). The compounds of the present invention are useful in the diagnosis and treatment of neurodegenerative diseases, and especially tauopathies such as Alzheimer's disease.

INTRODUCTION

Alzheimer's disease is a neurodegenerative disorder causing symptoms that include memory loss, difficulties with thinking, problem-solving, speech and/or language, personality changes, hallucinations, delusions, low mood and anxiety. It is the most common cause of dementia. Alzheimer's is a progressive disease and over time more symptoms develop, and the symptoms become more severe.

Protein deposits are the pathological hallmarks of a wide range of neurodegenerative diseases (C. A. Ross, M. A. Poirier, *Nat. Med.* 2004, 10, 10-17), including Alzheimer's disease and corticobasal degeneration. Small hydrophobic ligands that are selective for protein aggregates having an extensive cross β-pleated sheet conformation and sufficient structural regularity have been developed. The most common ligands are derivatives of Congo Red or thioflavins and a variety of other molecular scaffolds have also been reported (K. P. R. Nilsson, *FEBS Lett.* 2009, 583, 2593-2599). However, most of these ligands can only generally detect disease-associated protein aggregates, and they are not able to detect specific disease-associated protein aggregates consisting of a distinct protein.

The microtubule associated protein tau is one protein deposit shown to cause neurodegeneration. Tau can form intracellular fibrillary deposits in neurons and glial cells, and these tau deposits are linked to a large variety of disorders, collectively referred to as tauopathies. Tauopathies include more than 20 disorders including Alzheimer's disease, progressive supranuclear palsy (PSP), corticobasal degeneration (CBD), and Pick's disease. Although dysfunction of tau has unequivocally been shown to be able to cause neurodegeneration, the precise mechanisms of how tau is involved in neurodegenerative disorders is still poorly understood. According to currently emerging cell biological concepts, tau might play a role in the regulation of neuronal plasticity in a wide array of neuronal networks. In addition, it might be involved in regulating genome stability (Arendt, T., et al, Brain Research Bulletin, 2016, 126, 238-292).

In Alzheimer's disease, the two major proteinaceous deposits are extracellular senile plaques consisting of aggregated amyloid-β (Aβ) peptide and intraneuronal neurofibrillary tangles (NFTs) composed of aggregated tau (C. A. Ross, M. A. Poirier, *Nat. Med.* 2004, 10, 10-17; C. Ballatore, V. M. Y Lee, J. Q. Trojanowski. *Nat Rev Neurosci.* 2007, 8, 663-672). The development of ligands that can specifically target Aβ or tau deposits are essential for clinical diagnostic of Alzheimer's disease, as well as for evaluating the contribution of these respective aggregated species to the complex molecular pathology in Alzheimer's disease brain. Molecular scaffolds enabling visualization of Aβ deposits in humans with Alzheimer's disease by positron emission tomography (PET) imaging have been presented (W. E. Klunk, et al, *Ann. Neurol.* 2004, 55, 306-319; Y. Kudo, et al, *J. Nucl. Med.* 2007, 48, 553-561; and L. Yang, D., et al, *N. Engl. J. Med.* 2012, 367, 885-887). More recently, some molecular scaffolds targeting the other pathological hallmark in Alzheimer's disease, tau deposits, have also been recognized (G. W. Small, et al, *N. Eng. J. Med.* 2006, 355, 2652-2663; Taghavi, et al, *Alzheimers Dis.* 2011, 27, 835-843; M. T. Fodero-Tavoletti, et al, *Brain.* 2011, 134, 1089-1100; W. Zhang, et al, *Alzheimers Dis.* 2012, 31, 601-612; M. Maruyama, et al, *Neuron* 2013, 79, 1094-1108; and C. F. Xia, et al. *Alzheimers Dement.* 2013, 9, 666-676).

Luminescent conjugated oligothiophenes (LCOs) have been utilized for fluorescence imaging of protein aggregates. Compared to conventional ligands, LCOs have been shown to detect a wider range of disease-associated protein aggregates (A. Åslund, et al, ACS Chem. Biol. 2009, 4, 673-684; T. Klingstedt, et al, *Org. Biomol. Chem.* 2011, 9, 8356-8370; H. Shirani, et al, *Chemistry* 2015, 21, 15133-15137). In addition, LCOs having distinct chemical compositions can be utilized for spectral assessment of distinct protein aggregates, such as Aβ or tau deposits in Alzheimer's disease (T. Klingstedt, et al, *Chemistry* 2013, 19, 10179-1019; T. Klingstedt, et al, *Chemistry* 2015, 21, 9072-9082.). Lately, a thiophene based tetrameric ligand, q-FTAA-CN with a striking higher affinity for Aβ deposits than aggregated species composed of tau was identified (M. Back, et al, *Chemistry.* 2016, 22, 18335-18338).

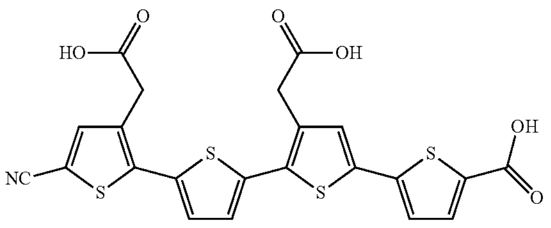

q-FTAA-CN

PBB3 is also known to be a tau specific ligand (M. Maruyama, et al, *Neuron* 2013, 79, 1094-1108).

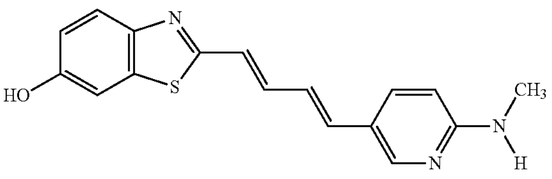

PBB3

MK6240 is also known to be a tau specific ligand (E. D. Hostetler, et al, J Nucl Med 2016, 57, 1599-1606).

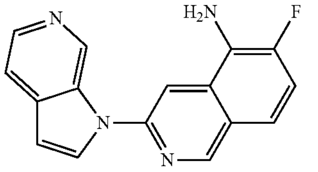

MK-6240

However, different morphotypes of Aβ and tau aggregates have been reported (C. L. Maarouf, I et al, *Mol. Neurodegener.* 2008, 3, 20; H. Levine, L. C. Walker, *Neurobiol. Aging* 2010, 31, 542-548; F. Clavaguera, et al, *Proc. Natl. Acad. Sci. USA* 2013, 110, 9535-9540; J. X. Lu, et al, *Cell* 2013, 154, 1257-1268; W. Qiang, et al, *Nature.* 2017, 541, 217-221). The existence of distinct aggregate morphotypes has been suggested to explain the heterogeneous phenotype reported for several neurodegenerative protein aggregation diseases. Hence, a variety of ligands will be necessary to achieve an accurate assessment of the diversity of pathological protein deposits present in neurodegenerative diseases, such as Alzheimer's disease. As such, there is a need to develop further small molecular ligands that target specific disease-associated protein aggregates, and in particular further molecular scaffolds enabling visualization of tau deposits, for example in humans with Alzheimer's disease (and other tauopathies).

Further, the known tau specific ligand PBB3 has been reported to have the significant disadvantage of undergoing photoisomerisation when exposed to fluorescent light (Hashimoto, H., et al, J Nucl Med (2014), Vol. 55, No. 9, pages 1532-1538). Hashimoto et al reported that at 1 min after exposure of a sample of $^{11}C$-PBB3 to fluorescent light, the radiochemical purity of $^{11}C$-PBB3 decreased to 77%, and from 10 to 60 min, the radiochemical purity was approximately 50%. Hashimoto et al also reported that the isomer of $^{11}C$-PBB3 that was formed showed much less specific binding to tau in the brain sections of Alzheimer's disease patients. This property makes PBB3 difficult to synthesize, radiolabel, store, and handle. This limits the practicality of using this tau ligand in in vitro experimentation and in vivo acquisitions (Saint-Aubert, L., et al, Molecular Neurodegeneration (2017), Vol. 12, No. 9*: Tau PET imaging: present and future directions*).

SUMMARY OF INVENTION

The invention provides a compound of formula (I), or a pharmaceutically acceptable salt, ester, amide or carbamate thereof, or a salt of such an ester, amide or carbamate, (I)

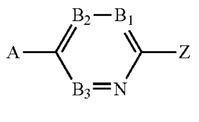

wherein

A is

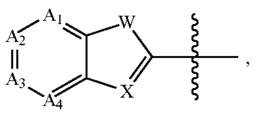

, and $A_1$ and $A_4$ are independently selected from the group consisting of N and CH;

$A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

W is selected from the group consisting of O, S and NH;

X is selected from the group consisting of N and CH;

or A is

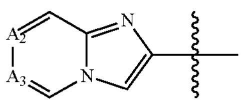

, and $A_2$ is selected from the group consisting of N, $CR^2$ and CH and $A_3$ is selected from the group consisting of N and CH, or $A_2$ is selected from the group consisting of N and CH and $A_3$ is selected from the group consisting of N, $CR^2$ and CH;

$B_1$, $B_2$, and $B_3$, are each independently selected from the group consisting of N, CH and $CR^3$, wherein at least one of $B_1$, $B_2$, and $B_3$ is CH or $CR^3$;

Z is selected from the group consisting of

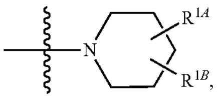

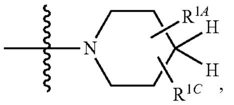

,

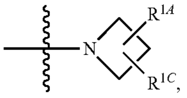

, and

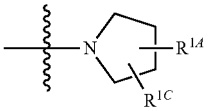

when present $R^{1A}$ is selected from the group consisting of halogen (for example Cl, Br or I); —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; $C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present $R^{1B}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present $R^{1C}$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS—; $C_{1-6}$alkylS(=O)—; $C_{1-6}$alkylS($O_2$)—; $NO_2$; —N(Ra)$_2$; —$C_{1-6}$alkylN(Ra)$_2$; —N($R^a$)C(O)H; —N($R^a$)C(O)$C_{1-6}$alkyl optionally substituted with 1, 2 or 3 halogen; C(O)N($R^g$)$_2$; —$C_{1-6}$alkylC(O)N($R^g$)$_2$; and —$(OCH_2CH_2)_p$—$R^f$;

when present $R^3$ is selected from the group consisting of halogen; OH; $C_{1-6}$alkyl optionally substituted with 1, 2 or 3 halogen (preferably 1, 2 or 3 fluorine); and —O$C_{1-6}$alkyl optionally substituted with 1, 2 or 3 halogen (preferably 1, 2 or 3 fluorine);

when present $R^1$, $R^b$, $R^c$ and $R^d$ are each independently selected from the group consisting of H and $C_{1-6}$alkyl optionally substituted with 1, 2 or 3 halogen;

when present $R^e$ is selected from the group consisting of H and $C_{1-6}$alkyl optionally substituted with 1, 2 or 3 halogens;

when present $R^f$ is selected from the group consisting of H; halogen; —$CH_2$(halogen), —CH(halogen)$_2$, —C(halogen)$_3$, and OH;

when present each $R^g$ is independently selected from the group consisting of H; $C_{1-6}$alkyl; $C_{1-6}$alkyl substituted with 1, 2 or 3 halogen; $C_{1-6}$alkyl substituted with 1, 2 or 3 OH groups; $C_{1-6}$alkyl substituted with 1, 2 or 3 —O$C_{1-3}$alkyl groups; $C_{1-6}$alkyl substituted with a —OS(O)$_2CH_3$ group; and $C_{1-6}$alkyl substituted with a —S(O)$_2OCH_3$ group; and p is 2, 3, 4, 5, 6, 7 or 8.

The present invention also provides a compound of formula (X), or a pharmaceutically acceptable salt, ester, amide or carbamate thereof, or a salt of such an ester, amide or carbamate,

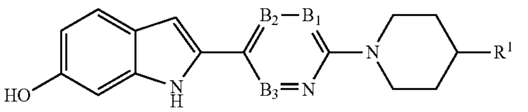

(X)

wherein $B_1$, $B_2$, and $B_3$, are each independently selected from the group consisting of N, CH and $CR^3$, wherein at least one of $B_1$, $B_2$, and $B_3$ is CH or $CR^3$;

$R^1$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O) $C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C (O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present $R^3$ is selected from the group consisting of halogen; OH; $C_{1-6}$alkyl optionally substituted with 1, 2 or 3 halogen (preferably 1, 2 or 3 fluorine); and —$OC_{1-6}$alkyl optionally substituted with 1, 2 or 3 halogen (preferably 1, 2 or 3 fluorine);

when present $R^b$, $R^c$ and $R^d$ are each independently selected from the group consisting of H and $C_{1-6}$alkyl optionally substituted with 1, 2 or 3 halogen;

when present $R^e$ is selected from the group consisting of H and $C_{1-6}$alkyl optionally substituted with 1, 2 or 3 halogens;

when present $R^f$ is selected from the group consisting of H; halogen; —$CH_2$(halogen), —CH(halogen)$_2$, —C(halogen)$_3$, and OH; and p is 2, 3, 4, 5, 6, 7 or 8.

The invention also provides a pharmaceutical or diagnostic composition comprising a compound of formula (I) or (X), together with a pharmaceutically suitable carrier.

The invention further provides a compound of formula (I) or (X) (or a composition comprising a compound of formula (I) or (X)) for use as a diagnostic agent wherein the compound of formula (I) or (X) comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

The invention further provides the use of a compound of formula (I) or (X) for the detection of tau deposits.

The invention further provides a method of diagnosing a patient or monitoring disease progression in a patient comprising administering a compound of formula (I) or (X) (or a composition comprising a compound of formula (I) or (X)) to the patient, wherein the compound of formula (I) or (X) comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

The invention further provides a compound of formula (I) or (X) or a composition comprising a compound of formula (I) or (X), for use as a medicament.

DETAILED DESCRIPTION

The present inventors have synthesized various compounds of formula (I) and (X) and shown that compounds of the invention have excellent binding affinity for tau deposits. The preferred compounds of the invention are also selective tau deposit ligands, i.e. as well as having excellent binding affinity for tau deposits, they also selectively bind tau deposits in preference to amyloid beta (Aβ) deposits.

Furthermore, the compounds of the present invention are not light sensitive, as they do not have a photoisomerisable double bonds in their structure. Therefore, they have significant advantages over the known tau selective ligand PBB3 with respect to their synthesis (including radiolabeling), storage, and handling, and can be feasibly used in in vitro experimentation and in vivo acquisitions.

A further advantage of the compounds of the invention is that the compounds bind to the four-repeat (4R) isomer forms of tau. 4R forms of tau are known to be present in various tauopathies, such as Alzheimer's disease, progressive supranuclear palsy and corticobasal degeneration. This makes the compounds of the invention especially useful for the diagnosis and/or the treatment or prophylaxis of conditions associated with 4R forms of tau, such as Alzheimer's disease, progressive supranuclear palsy and corticobasal degeneration.

A further advantage of the compounds of the invention is that they are expected to have low binding affinity for MAO enzymes in the human brain. As reported in Murugan, N. A., et al, Eur J Nucl Med Mol Imaging. (2019) doi: 10.1007/s00259-019-04305-8, areas of the brain with the highest concentrations of MAO-B overlap with areas of tau pathology in taopathies such as CBD and PSP. Therefore, it is undesirable for a tau deposit ligand to have off-target binding to MAO, as such off-target effects severely limit the use of the tau deposit ligand for in vivo tau imaging. The compounds of the invention are expected to be specific to tau accumulation in the brain, and thus have good specificity and sensitivity when used as tau imaging agent in vivo in all taupathies, including CBD and PSP.

Isotopic forms, for example where a hydrogen atom is replaced with deuterium ($^2H$) or tritium ($^3H$), or a carbon atom is replaced with a $^{13}C$ atom, or a fluorine atom is replaced with a $^{18}F$ atom, are included within the invention. Certain isotopic forms may have beneficial biological properties, for example improved metabolic stability or enhanced therapeutic activity over other isotopic forms. Some specific isotopic forms may be useful for biological imaging purposes, for example carbon-11 ($^{11}C$), nitrogen-13 ($^{13}N$), oxygen-15 ($^{15}O$), fluorine-18 ($^{18}F$) or iodine-120 ($^{120}I$) isotopic variants may be used for positron emission tomography, and tritium ($H^3$) and iodine-125 ($I^{125}$) may be used for in vitro studies.

The present invention provides compounds of formula (I):

(I)

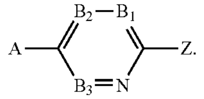

In the compound of formula (I), A may be

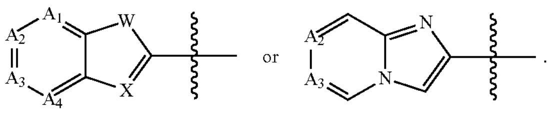

In embodiments where A is:

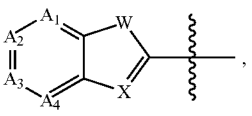

$A_1$ and $A_4$ are independently selected from the group consisting of N and CH; $A_2$ is selected from the group consisting of N, $CR^2$ and CH, and $A_3$ is selected from the group consisting of N and CH, and wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH.

$A_1$ and $A_4$ may independently selected from the group consisting of N and CH; and $A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH; In certain preferred embodiments, $A_1$ and $A_4$ are CH; or $A_1$ is N and $A_4$ is CH.

Preferably $A_1$ and $A_4$ are CH. Even more preferably, $A_1$ and $A_4$ are CH, and $A_2$ is selected from the group consisting of N, $CR^2$ and CH and $A_3$ is selected from the group consisting of N and CH; or $A_2$ is selected from the group consisting of N and CH and $A_3$ is selected from the group consisting of N, $CR^2$ and CH.

Even more preferably, $A_1$ and $A_4$ are CH, $A_2$ is selected from the group consisting of N and CH, and $A_3$ is selected from the group consisting of N, $CR^2$ and CH.

In other preferred embodiments, $A_1$ is N and $A_4$ is CH. Even more preferably, $A_1$ is N, $A_4$ is CH, $A_2$ is selected from the group consisting of N, $CR^2$ and CH, and $A_3$ is selected from the group consisting of N and CH; or $A_1$ is N, $A_4$ is CH, $A_2$ is selected from the group consisting of N and CH, and $A_3$ is selected from the group consisting of N, $CR^2$ and CH. Even more preferably, $A_1$ is N, $A_4$ is CH, $A_2$ is selected from the group consisting of N, $CR^2$ and CH, and $A_3$ is selected from the group consisting of N and CH.

In certain preferred embodiments, $A_2$ is selected from the group consisting of $CR^2$ and CH and $A_3$ is selected from the group consisting of N and CH. In another preferred embodiment, $A_2$ is selected from the group consisting of N and CH (and is preferably CH) and $A_3$ is selected from the group consisting of $CR^2$ and CH.

In certain preferred embodiments, $A_3$ and $A_4$ are independently selected from the group consisting of N and CH. In such embodiments, preferably at least three of $A_1$, $A_2$, $A_3$ and $A_4$ are CH or at least two of $A_1$, $A_2$, $A_3$ and $A_4$ are CH.

In one preferred embodiment, $A_1$ and $A_4$ are independently selected from the group consisting of N and CH, and:

$A_2$ is selected from the group consisting of N, $CR^2$ and CH, and $A_3$ is selected from the group consisting of N and CH, wherein at least three of $A_1$, $A_2$, $A_3$, and $A_4$ are CH, or wherein $A_2$ is $CR^2$ and at least two of $A_1$, $A_3$ and $A_4$ is CH; or $A_2$ is selected from the group consisting of N and CH, and $A_3$ is selected from the group consisting of N, $CR^2$ and CH, wherein at least three of $A_1$, $A_2$, $A_3$, and $A_4$ are CH, or wherein $A_3$ is $CR^2$ and at least two of $A_1$, $A_2$ and $A_4$ is CH.

More preferably, $A_1$ and $A_4$ are CH. For example, $A_1$ and $A_4$ are CH, and:

$A_2$ is selected from the group consisting of N, $CR^2$ and CH, and $A_3$ is selected from the group consisting of N and CH, wherein at least one of $A_2$ and $A_3$ is CH, or wherein $A_2$ is $CR^2$; or $A_2$ is selected from the group consisting of N and CH, and $A_3$ is selected from the group consisting of N, $CR^2$ and CH, wherein at least one of $A_2$ and $A_3$ is CH, or wherein $A_3$ is $CR^2$.

In another preferred embodiment, at least two of $A_1$, $A_2$, $A_3$, and $A_4$ are CH, for example three of $A_1$, $A_2$, $A_3$, and $A_4$ are CH. In one preferred embodiment each of $A_1$, $A_2$, $A_3$, and $A_4$ is CH.

In another preferred embodiment, at least one of $A_1$, $A_2$, $A_3$, and $A_4$ are CH and at least one of $A_1$, $A_2$, $A_3$, and $A_4$ is N, for example one of $A_1$, $A_2$, $A_3$, and $A_4$ is CH and two of $A_1$, $A_2$, $A_3$, and $A_4$ are N.

In another preferred embodiment, three of $A_1$, $A_2$, $A_3$, or $A_4$ are CH, and the remaining $A_1$, $A_2$, $A_3$, or $A_4$ group is N or CH; or is N or $CR^2$; or is $CR^2$. For example, each of $A_1$, $A_2$, and $A_4$ are CH, and $A_3$ is N or CH; or $A_3$ is N or $CR^2$; or $A_3$ is $CR^2$. In another embodiment, each of $A_1$, $A_3$, and $A_4$ are CH, and $A_2$ is N or CH; or $A_2$ is N or $CR^2$; or $A_2$ is $CR^2$. In one preferred embodiment each of $A_1$, $A_3$, and $A_4$ are CH, and $A_2$ is $CR^2$ (and even more preferably, $R^2$ is O—$C_{1-6}$alkyl optionally substituted with 1, 2 or 3 halogen or OH groups).

In another preferred embodiment, $A_1$, $A_2$, $A_3$, and $A_4$ are independently selected from the group consisting of N and CH, wherein at least three of $A_1$, $A_2$, $A_3$, and $A_4$ are CH (for example $A_1$, $A_2$, and $A_4$ are CH, and $A_3$ is N or CH).

In an especially preferred embodiment, $A_1$ and $A_4$ are CH, $A_2$ is selected from the group consisting of $CR^2$ and CH, and $A_3$ is selected from the group consisting of N and CH; or $A_1$ and $A_4$ are CH, $A_2$ is selected from the group consisting of N and CH (and is preferably CH), and $A_3$ is selected from the group consisting of $CR^2$ and CH. Even more preferably, $A_1$ and $A_4$ are CH, $A_2$ is selected from the group consisting of $CR^2$ and CH (and preferably is $CR^2$), and $A_3$ is selected from the group consisting of N and CH (and preferably is CH).

In another especially preferred embodiment, each of $A_1$ and $A_3$ is N, $A_3$ is CH, and $A_2$ is $CR^2$; or each of $A_2$ and $A_4$ is N, $A_1$ is CH, and $A_3$ is $CR^2$. Even more preferably $A_1$ and $A_3$ is N, $A_3$ is CH, and $A_2$ is $CR^2$ (and preferably $R^2$ is O—$C_{1-6}$alkyl optionally substituted with 1, 2 or 3 halogen or OH groups).

In embodiments where A is:

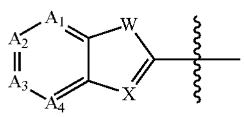

,

W is selected from the group consisting of O, S and NH; and X is selected from the group consisting of N and CH. In some preferred embodiments, W is selected from the group consisting of S or O. In other preferred embodiments, X is N. In certain embodiments W is selected from the group consisting of S or O, and X is selected from the group consisting of N or CH. In one preferred embodiment, W is S and X is N. In another preferred embodiment W is NH and X is CH.

In certain embodiments, W is S and X is CH; W is NH and X is N; or W is O and X is CH. In an especially preferred embodiment, W is S and X is N.

In certain embodiments, W is S and X is N or CH; W is NH and X is CH; or W is O and X is CH or N. More preferably W is S and X is N or CH; or W is NH and X is CH; or W is O and X is CH.

In another especially preferred embodiment, W is NH and X is CH.

In compounds where A is

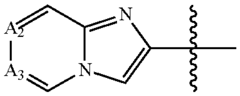, preferably $A_2$ is selected from the group consisting of $CR^2$ and CH and $A_3$ is selected from the group consisting of N and CH, or $A_2$ is selected from the group consisting of N and CH (and is preferably CH) and $A_3$ is selected from the group consisting of $CR^2$ and CH. In certain preferred embodiments, $A_2$ is $CR^2$ and $A_3$ is selected from the group consisting of N and CH, or $A_2$ is selected from the group consisting of N and CH (and is preferably CH) and $A_3$ is $CR^2$.

In one preferred embodiment, $A_2$ is CH or N and $A_3$ is selected from the group consisting of N and CH, or $A_2$ is selected from the group consisting of N and CH (and is preferably CH) and $A_3$ is selected from the group consisting of CH or N (and is preferably CH).

$B_1$, $B_2$, and $B_3$ are each independently selected from the group consisting of N, CH and $CR^3$, wherein at least one of $B_1$, $B_2$, and $B_3$ is selected from the group consisting of CH and $CR^3$ (for example, two of $B_1$, $B_2$, and $B_3$ are independently selected from the group consisting of N, CH and $CR^3$, and one of $B_1$, $B_2$, and $B_3$ is selected from the group consisting of CH and $CR^3$). Preferably, at least two of $B_1$, $B_2$, and $B_3$ are selected from the group consisting of CH and $CR^3$ (for example, one of $B_1$, $B_2$, and $B_3$ is selected from the group consisting of N, CH and $CR^3$, and two of $B_1$, $B_2$, and $B_3$ are independently selected from the group consisting of CH and $CR^3$). For example, at least one of $B_1$, $B_2$, and $B_3$ is CH, and at least one of $B_1$, $B_2$, and $B_3$ (i.e. at least one of the remaining two of $B_1$, $B_2$, and $B_3$) is selected from the group consisting of $CR^3$ and CH. In certain preferred embodiments, at least two of $B_1$, $B_2$, and $B_3$ are CH.

In certain preferred embodiments, $B_1$ is N. In certain other preferred embodiments, $B_3$ is N.

In certain preferred embodiments, $B_1$, $B_2$, and $B_3$ are each independently selected from the group consisting of N, CH and $CR^3$, wherein at least one of $B_1$, $B_2$, and $B_3$ is CH, and at least one of $B_1$, $B_2$, and $B_3$ (i.e. at least one of the remaining two of $B_1$, $B_2$, and $B_3$) is selected from the group consisting of $CR^3$ and CH. Even more preferably, $B_1$, $B_2$, and $B_3$ are each independently selected from the group consisting of N, CH and $CR^3$, wherein at least two of $B_1$, $B_2$, and $B_3$ are CH.

In certain preferred embodiments, two of $B_1$, $B_2$, and $B_3$ are CH, and the other $B_1$, $B_2$, or $B_3$ group is selected from the group consisting of N and $CR^3$.

In one preferred embodiment $B_1$ and $B_2$ are selected from the group consisting of N and CH, and $B_3$ is selected from the group consisting of N, CH and $CR^3$, wherein at least one of $B_1$, $B_2$, and $B_3$ is CH or $CR^3$, and preferably at least two of $B_1$, $B_2$, and $B_3$ are CH and/or $CR^3$. For example, $B_1$ and $B_2$ are CH and $B_3$ is CH or $CR^3$ (and preferably $B_1$ and $B_2$ are CH and $B_3$ is $CR^3$), or $B_1$ is N, $B_2$ is CH, and $B_3$ is CH or $CR^3$ (and preferably $B_1$ is N, $B_2$ is CH, and $B_3$ is CH).

In another preferred embodiment, $B_2$ and $B_3$, are each independently selected from the group consisting of $CR^3$ and CH, and $B_1$ is selected from the group consisting of N, $CR^3$ and CH (for example, $B_1$ is N or CH). Preferably, $B_2$ and $B_3$ are each CH, and $B_1$ is selected from the group consisting of N, $CR^3$ and CH (for example, $B_1$ is N or CH). Even more preferably, $B_2$ and $B_3$ are each CH, and $B_1$ is N; or $B_1$, $B_2$, or $B_3$ are each CH. In an alternative embodiment, one of $B_2$ and $B_3$ is $CR^3$ and the other is CH, and $B_1$ is selected from the group consisting of N, $CR^3$ and CH (and preferably N and CH, for example $B_1$ is N, or $B_1$ is CH).

In another embodiment, $B_1$ and $B_2$ are each independently selected from the group consisting of $CR^3$ and CH, and $B_3$ is selected from the group consisting of N, $CR^3$ and CH (for example, $B_3$ is N or CH). Preferably, $B_1$ and $B_2$ are each CH, and $B_3$ is selected from the group consisting of N, $CR^3$ and CH (for example, $B_3$ is N or CH). Even more preferably, $B_1$ and $B_2$ are each CH, and $B_3$ is N; or $B_1$, $B_2$, and $B_3$ are each CH. In an alternative embodiment, one of $B_1$ and $B_2$ is $CR^3$ and the other is CH, and $B_3$ is selected from the group consisting of N, $CR^3$ and CH (and preferably N and CH, for example $B_3$ is N, or $B_3$ is CH).

In certain preferred embodiments, $B_1$ or $B_3$ is $CR^3$ (and preferably $B_1$ or $B_3$ is CF).

In embodiments wherein $B_1$, $B_2$, and/or $B_3$ may be $CR^3$ (especially in embodiments wherein $B_1$ or $B_3$ is $CR^3$) it is especially preferred that $R^3$ is F (i.e. preferably $B_1$, $B_2$ and/or $B_3$ are CF (for example $B_1$ is CF, or $B_3$ is CF).

In certain preferred embodiments, $B_2$ is CH.

In one especially preferred embodiment, $B_1$, $B_2$, and $B_3$ are each CH. In another especially preferred embodiment, two of $B_1$, $B_2$, and $B_3$ are CH, and one of $B_1$, $B_2$, and $B_3$ is CF. In another especially preferred embodiment, two of $B_1$, $B_2$, and $B_3$ are CH, and one of $B_1$, $B_2$, and $B_3$ is N.

In another especially preferred embodiment, $B_1$ and $B_2$ are each CH and $B_3$ is CH or $CR^3$ (more preferably $B_3$ is $CR^3$); or $B_2$ and $B_3$ are each CH and $B_1$ is CH or N (more preferably $B_1$ is N). In very especially preferred embodiment, $B_1$ and $B_2$ are each CH and $B_3$ is CH or CF (more preferably $B_3$ is CF); or $B_2$ and $B_3$ are each CH and $B_1$ is CH or N (more preferably $B_1$ is N).

In the compounds of formula (I), Z is selected from the group consisting of

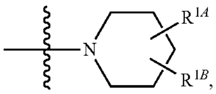, 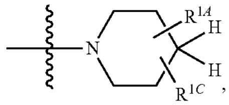,

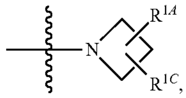, 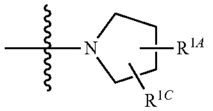

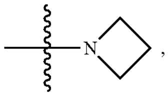, and 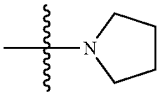.

For example, Z is selected from the group consisting of

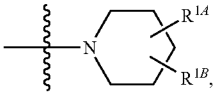, 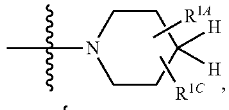,

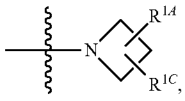, and 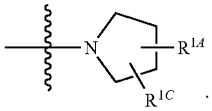.

Preferably, Z is selected from the group consisting of
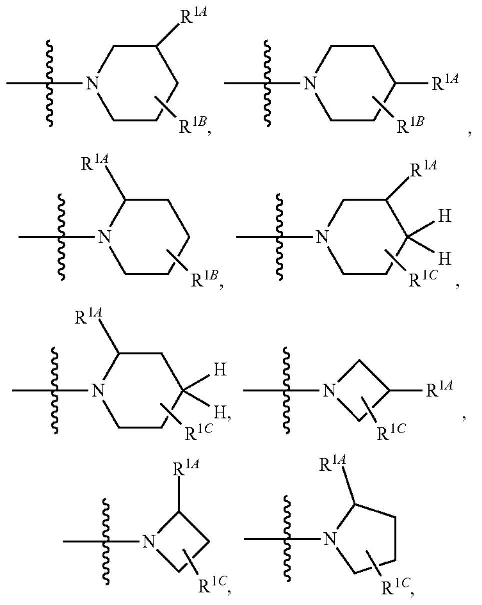
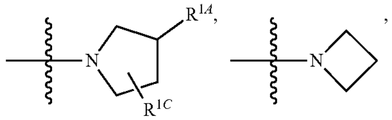
and
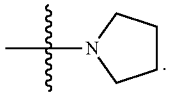
For example, Z is selected from the group consisting of
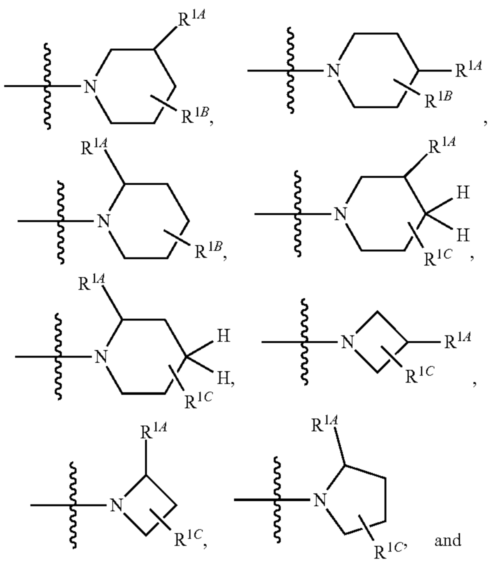
and
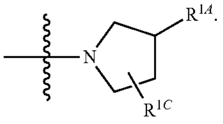
In one preferred embodiment, Z is selected from the group consisting of
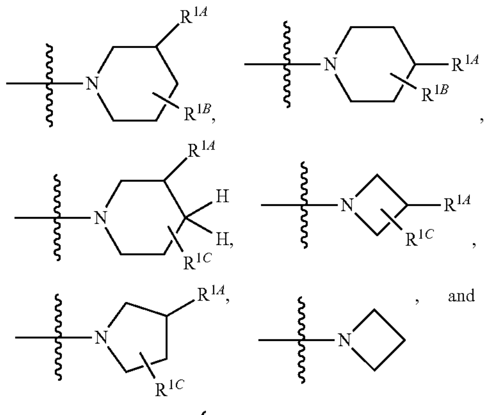
and
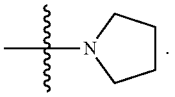
For example, Z is selected from the group consisting of
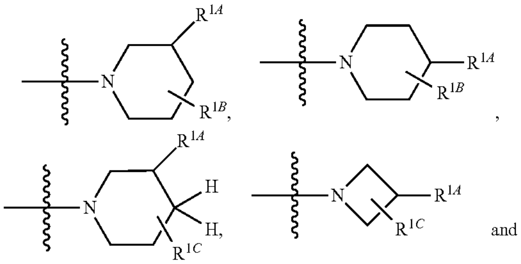
and
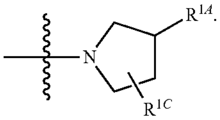
In one preferred embodiment, Z is selected from the group consisting of
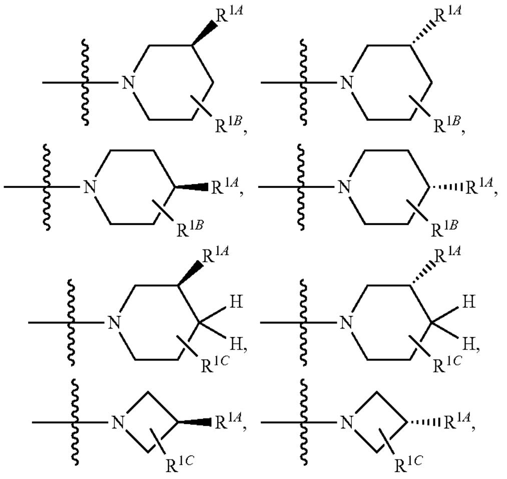

-continued
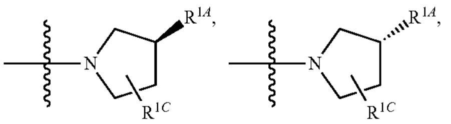
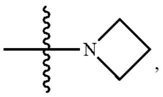
and
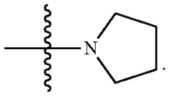
In another preferred embodiment, Z is selected from the group consisting of
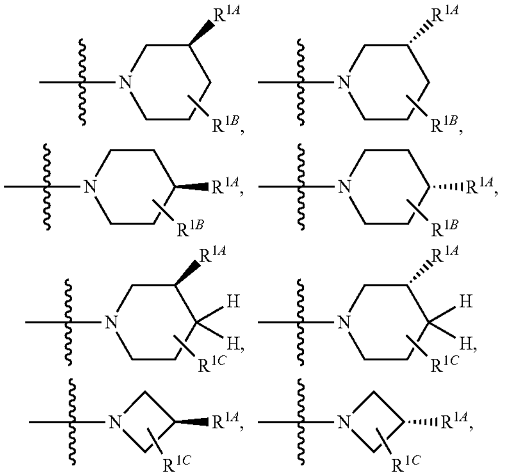
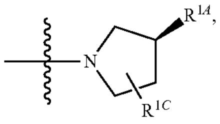
and
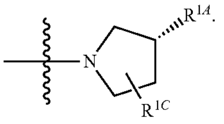
For example, Z is selected from the group consisting of
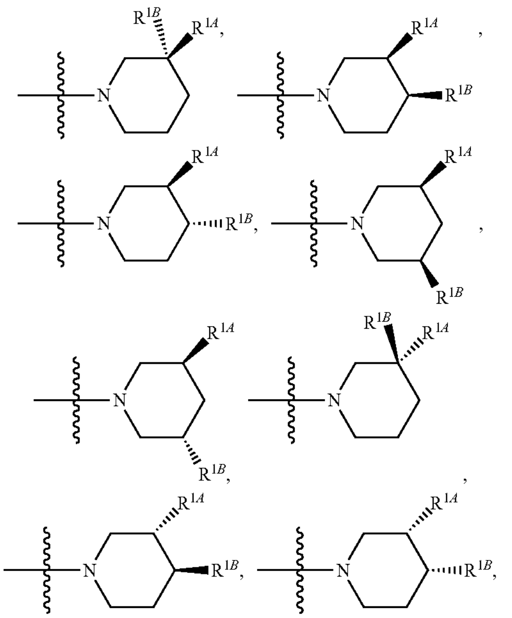
-continued
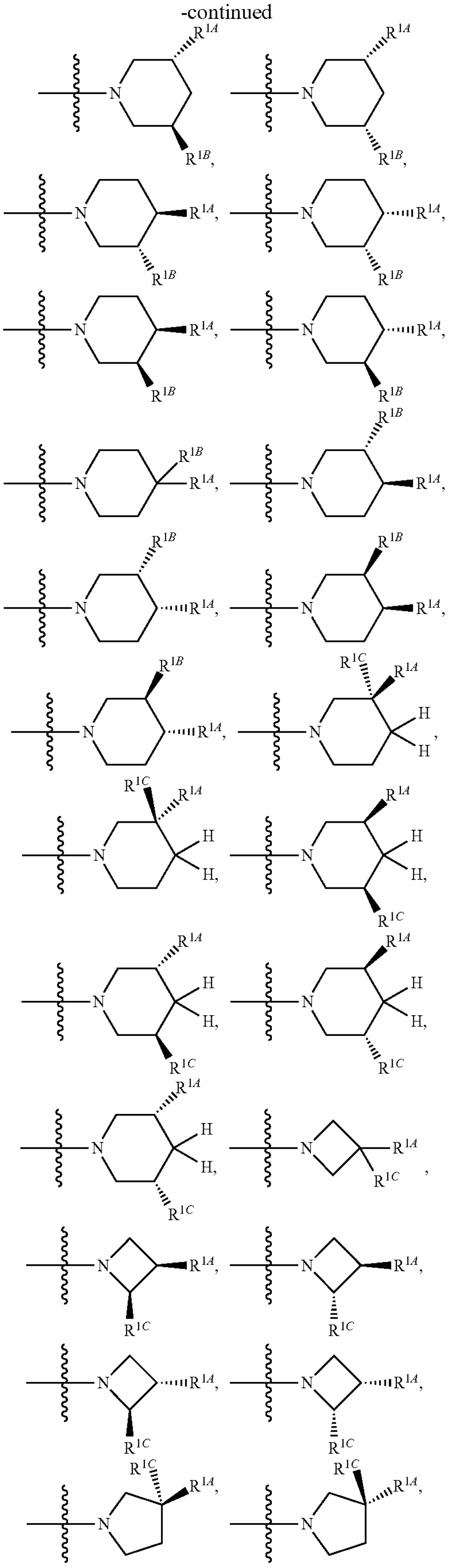

-continued
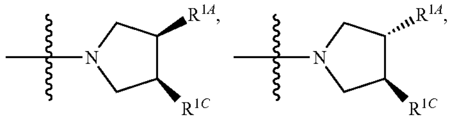
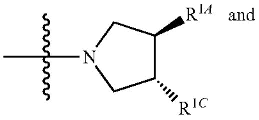
and
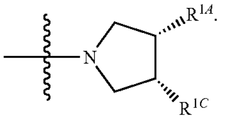
In one embodiment, Z is selected from the group consisting of
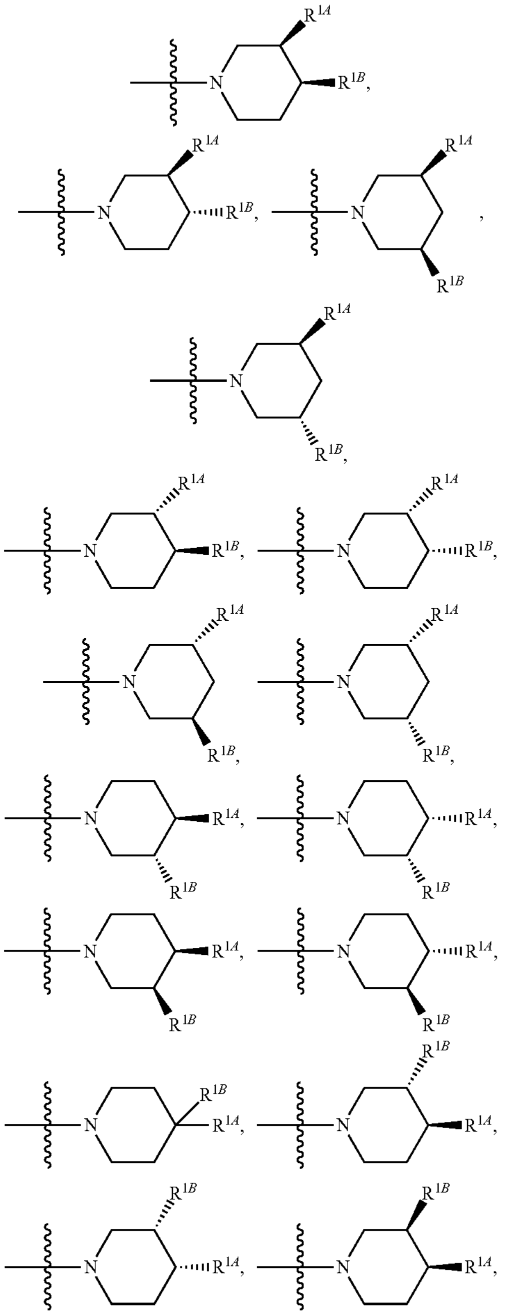
-continued
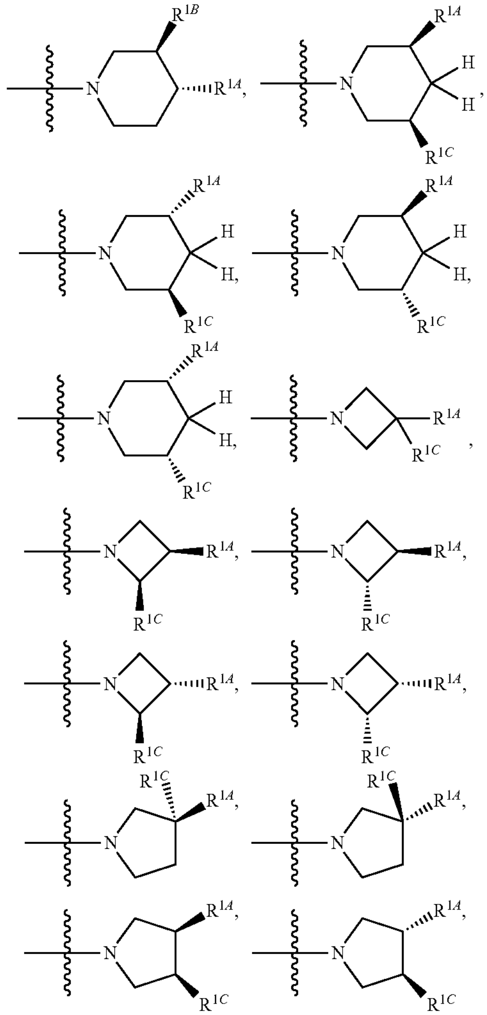
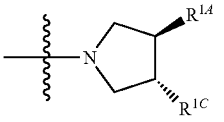
and
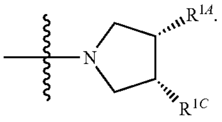
In certain preferred embodiments, when Z is
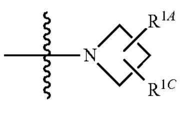
or
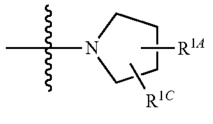
$R^{1C}$ is hydrogen. In such embodiments, Z may selected from the group consisting of
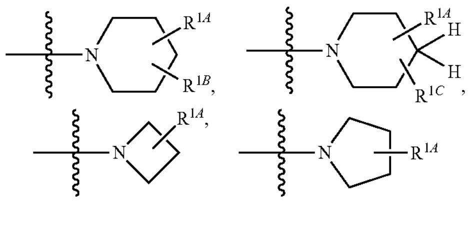

-continued

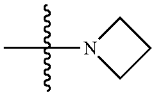
, and
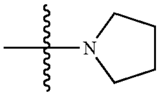
.

For example, Z may selected from the group consisting of

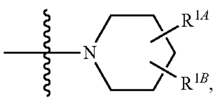
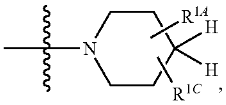
,
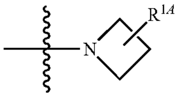
and
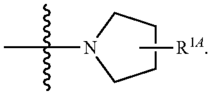

In one preferred embodiment, Z may be selected from the group consisting of:

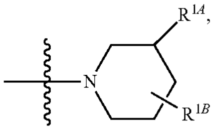
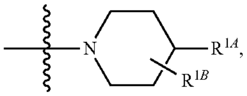
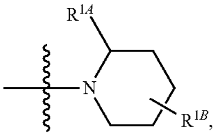
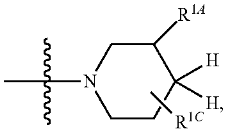
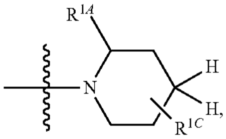
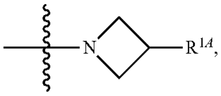
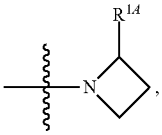
,
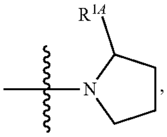
,
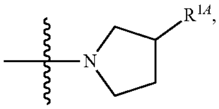
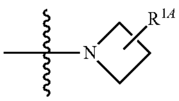
and
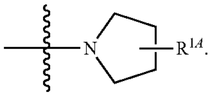

For example, Z may be selected from the group consisting of:

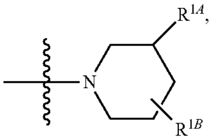
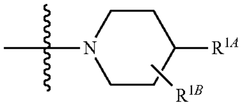
,

-continued

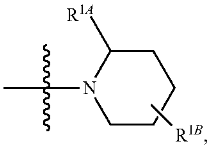
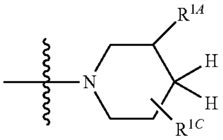
,
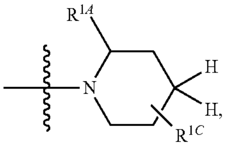
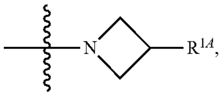
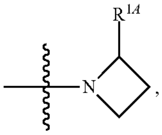
,
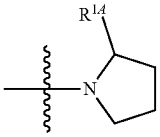
, and
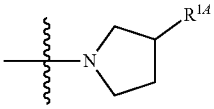
.

In particular, Z may be selected from the group consisting of:

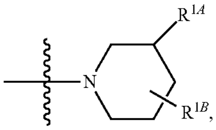
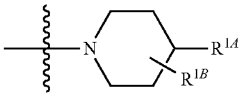
,
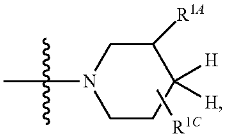
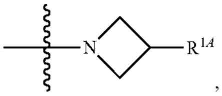
, and
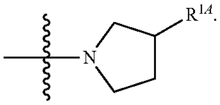

In certain preferred embodiments, Z is selected from the group consisting of

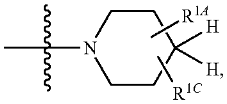
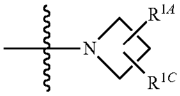
and
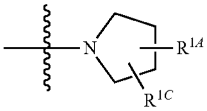

and $R^{1C}$ is hydrogen. In such embodiments, Z may selected from the group consisting of

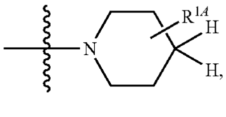
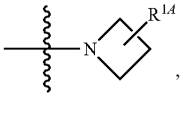
, and

-continued

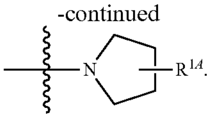

For example, Z may be selected from the group consisting of:

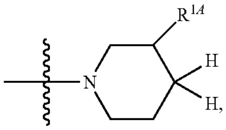 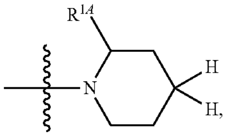

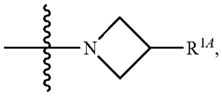 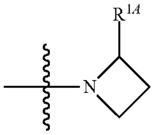,

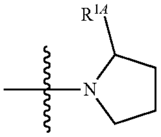, and 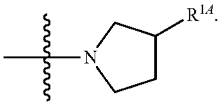

In such embodiments, Z may additionally be selected from the group consisting of

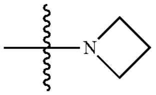, and 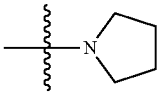.

In particular, Z may be selected from the group consisting of:

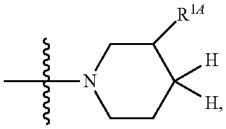 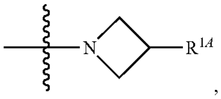, and

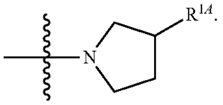

For example Z may be selected from the group consisting of:

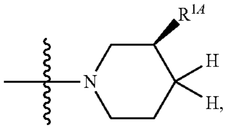 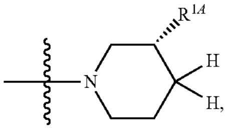

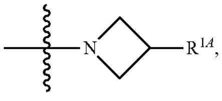 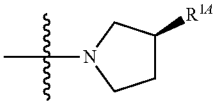 and

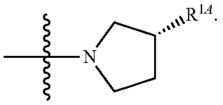

In another preferred embodiment, Z is

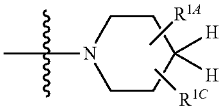

and $R^{1C}$ is hydrogen. In such embodiments, Z may selected from the group consisting of

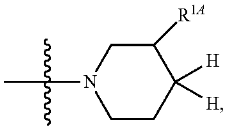 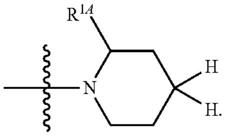

More preferably, Z is

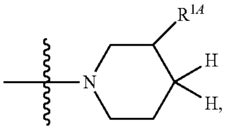

for example Z is

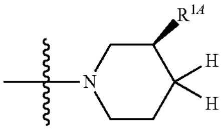 or 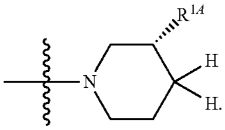

In certain embodiments, Z is

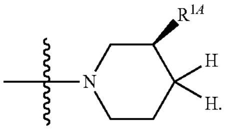

In certain embodiments, Z is

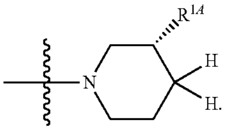

In another embodiment, Z is

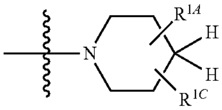

and $R^{1C}$ is not hydrogen (i.e. $R^{1C}$ is selected from a list of described herein, wherein hydrogen is omitted from the list). In such embodiments, Z may selected from the group consisting of

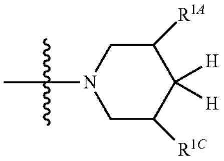

and

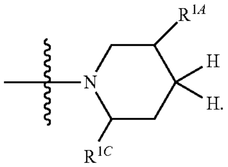

More preferably, Z is

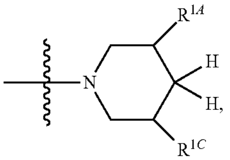

for example Z is

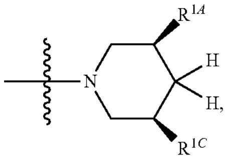

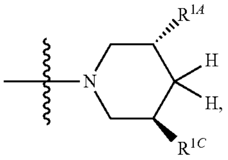

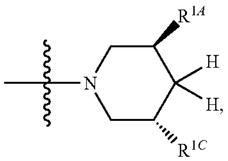

or

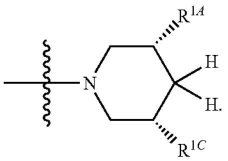

In certain embodiments, Z is,

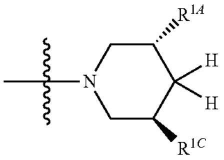

or

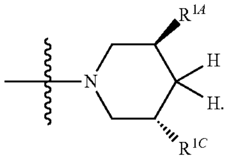

In another embodiment, Z is

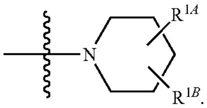

In such embodiments, Z may selected from the group consisting of

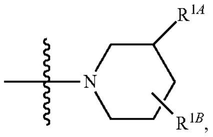

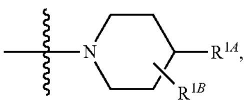

and

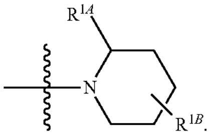

More preferably, Z is

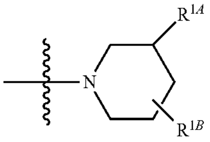

or

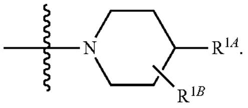

For example Z is

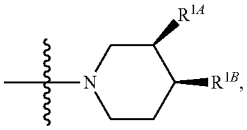

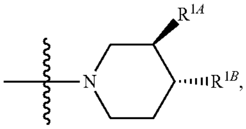

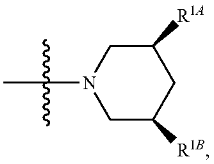

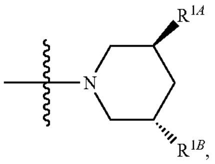

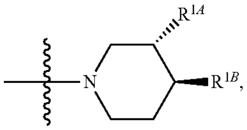

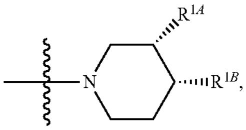

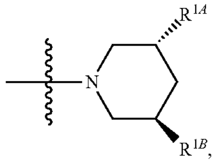

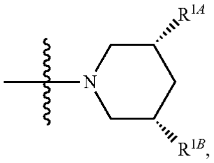

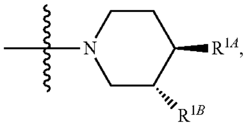

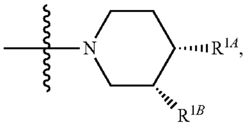

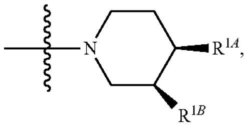

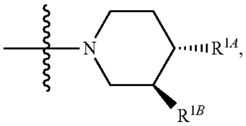

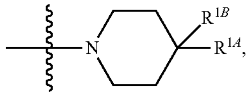

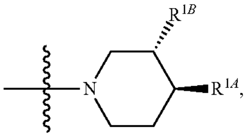

-continued

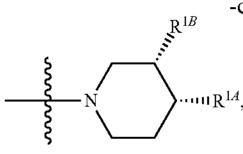

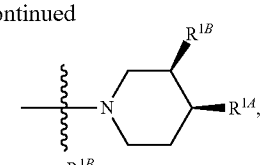

or

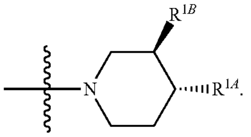

In certain embodiments, Z is,

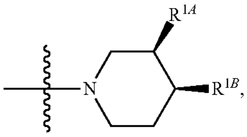

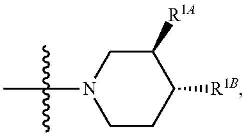

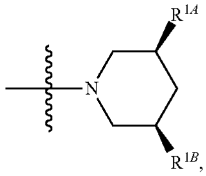

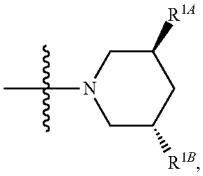

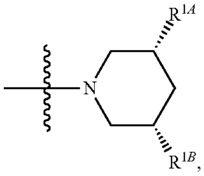

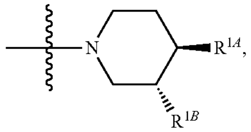

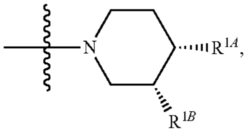

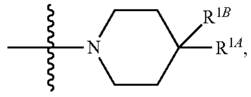

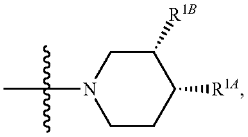

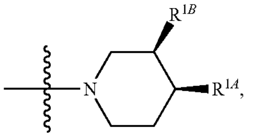

or

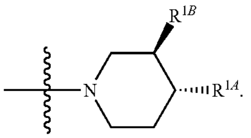

In compounds of formula (I), when present $R^{1A}$ may be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^{1A}$ may also be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

More preferably, $R^{1A}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^{1A}$ may also be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

Even more preferably, $R^{1A}$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen.

Also preferably, $R^{1A}$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In especially preferred embodiments, $R^{1A}$ is selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen. $R^{1A}$ may also be selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In another embodiment, $R^{1A}$ is selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F); C(O)—$N(H)_2$; and C(O)—O—$C_{1-3}$alkyl optionally substituted with 1, 2 or 3 halogen (preferably F). $R^{1A}$ may also be selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); and —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F).

In another embodiment, $R^{1A}$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and more preferably wherein $R^{1A}$ is selected from the group consisting of $C_{1-3}$alkyl optionally substituted with 1 OH group; C(O)—$N(H)_2$; and C(O)—O—$C_{1-3}$alkyl.

In another preferred embodiment, $R^{1A}$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^{1A}$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^{1A}$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F); C(O)—$N(R^d)_2$; and C(O)—O—$C_{1-6}$alkyl optionally substituted with 1 halogen (preferably F).

In another preferred embodiment, $R^{1A}$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^{1A}$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^{1A}$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F).

In another preferred embodiment, $R^{1A}$ is selected from the group consisting of halogen (preferably F); —OH; —$C_{1-6}$alkyl optionally substituted with 1, 2 or 3 (preferably 1) halogen (preferably F) or OH groups; —O—$C_{1-6}$alkyl optionally substituted with 1, 2 or 3 (preferably 1) halogen (preferably F) or OH groups; C(O)—$N(R^d)_2$; and C(O)—O—$C_{1-6}$alkyl optionally substituted with 1, 2 or 3 (preferably 1) halogen (preferably F).

In another preferred embodiment, $R^{1A}$ is selected from the group consisting of halogen (preferably F); —OH; —$C_{1-6}$alkyl optionally substituted with 1, 2 or 3 (preferably 1) halogen (preferably F) or OH groups; and —O—$C_{1-6}$alkyl optionally substituted with 1, 2 or 3 (preferably 1) halogen (preferably F) or OH groups.

In a further preferred embodiment, $R^{1A}$ is —OH, $C_{1-3}$alkyl optionally substituted with 1, 2 or 3 (preferably 1) halogen (preferably F) or OH groups, C(O)—$N(H)_2$ or C(O)—O—$C_{1-3}$alkyl. For example, $R^{1A}$ is OH. For example, $R^{1A}$ is —$C_{1-3}$alkyl optionally substituted with 1, 2 or 3 (preferably 1) halogen (preferably F). For example, $R^{1A}$ is C(O)—$N(H)_2$. For example, $R^{1A}$ is C(O)—O—$C_{1-3}$alkyl.

In one especially preferred embodiment, $R^{1A}$ is —OH or $C_{1-3}$alkyl optionally substituted with 1, 2 or 3 (preferably 1) halogen (preferably F) or OH groups (for example $CH_2OH$).

In compounds of formula (I), when present, $R^{1B}$ may be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)$C(O)H; $N(R^d)$C(O)$C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^{1B}$ may also be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)$C(O)H; $N(R^d)$C(O)$C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

More preferably, $R^{1B}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^{1B}$ may also be selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

Even more preferably, $R^{1B}$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen.

Also preferably, $R^{1B}$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In especially preferred embodiments, $R^{1B}$ is selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen. $R^{1B}$ may also be selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In another embodiment, $R^{1B}$ is selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F); C(O)—$N(H)_2$; and C(O)—O—$C_{1-3}$alkyl optionally substituted with 1, 2 or 3 halogen (preferably F). $R^{1B}$ may also be selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); and —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F).

In another embodiment, $R^{1B}$ is selected from the group consisting of —$C_{1-6}$alkyl optionally substituted with 1 halogen (preferably F) or OH group; C(O)—N($R^d$)$_2$ (preferably wherein each $R^d$ is H); and C(O)—O—$C_{1-6}$alkyl optionally substituted with 1 halogen (preferably F); and more preferably wherein $R^{1B}$ is selected from the group consisting of $C_{1-3}$alkyl optionally substituted with 1 OH group; C(O)—N(H)$_2$; and C(O)—O—$C_{1-3}$alkyl.

In another preferred embodiment, $R^{1B}$ is selected from the group consisting of OH; —$C_{1-6}$alkyl optionally substituted with 1 halogen (preferably F) or OH group; —$C_{1-6}$alkyl-O—S(O)$_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-S(O)$_2$—O-phenyl wherein said phenyl is optionally substituted with 1 $C_{1-3}$alkyl group and said $C_{1-3}$alkyl is optionally substituted with 1 halogen (preferably F). For example, $R^{1B}$ is selected from the group consisting of OH; —$C_{1-2}$alkyl optionally substituted with 1 halogen (preferably F) or OH group; and —$C_{1-2}$alkyl-O—S(O)$_2$-phenyl wherein said phenyl is optionally substituted with 1 $C_1$alkyl group; or, for example, $R^{1B}$ is selected from the group consisting of —$C_{1-2}$alkyl optionally substituted with 1 halogen (preferably F) or OH group; and —$C_{1-2}$alkyl-O—S(O)$_2$-phenyl wherein said phenyl is optionally substituted with 1 $C_1$alkyl group and said $C_1$alkyl optionally substituted with 1 halogen (preferably F); C(O)—N($R^d$)$_2$; and C(O)—O—$C_{1-6}$alkyl optionally substituted with 1 halogen (preferably F).

In another preferred embodiment, $R^{1B}$ is selected from the group consisting of OH; —$C_{1-6}$alkyl optionally substituted with 1 halogen (preferably F) or OH group; —$C_{1-6}$alkyl-O—S(O)$_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-S(O)$_2$—O-phenyl wherein said phenyl is optionally substituted with 1 $C_{1-3}$alkyl group and said $C_{1-3}$alkyl is optionally substituted with 1 halogen (preferably F). For example, $R^{1B}$ is selected from the group consisting of OH; —$C_{1-2}$alkyl optionally substituted with 1 halogen (preferably F) or OH group; and —$C_{1-2}$alkyl-O—S(O)$_2$-phenyl wherein said phenyl is optionally substituted with 1 $C_1$alkyl group; or, for example, $R^{1B}$ is selected from the group consisting of —$C_{1-2}$alkyl optionally substituted with 1 halogen (preferably F) or OH group; and —$C_{1-2}$alkyl-O—S(O)$_2$-phenyl wherein said phenyl is optionally substituted with 1 $C_1$alkyl group and said $C_1$alkyl optionally substituted with 1 halogen (preferably F).

In another preferred embodiment, $R^{1B}$ is selected from the group consisting of halogen (preferably F); —OH; —$C_{1-6}$alkyl optionally substituted with 1, 2 or 3 (preferably 1) halogen (preferably F) or OH groups; —O—$C_{1-6}$alkyl optionally substituted with 1, 2 or 3 (preferably 1) halogen (preferably F) or OH groups; C(O)—N($R^d$)$_2$; and C(O)—O—$C_{1-6}$alkyl optionally substituted with 1, 2 or 3 (preferably 1) halogen (preferably F).

In another preferred embodiment, $R^{1B}$ is selected from the group consisting of halogen (preferably F); —OH; —$C_{1-6}$alkyl optionally substituted with 1, 2 or 3 (preferably 1) halogen (preferably F) or OH groups; and —O—$C_{1-6}$alkyl optionally substituted with 1, 2 or 3 (preferably 1) halogen (preferably F) or OH groups.

In a further preferred embodiment, $R^{1B}$ is —OH, $C_{1-3}$alkyl optionally substituted with 1, 2 or 3 (preferably 1) halogen (preferably F) or OH groups, C(O)—N(H)$_2$ or C(O)—O—$C_{1-3}$alkyl. For example, $R^{1B}$ is OH. For example, $R^{1B}$ is —$C_{1-3}$alkyl optionally substituted with 1, 2 or 3 (preferably 1) halogen (preferably F). For example, $R^{1B}$ is C(O)—N(H)$_2$. For example, $R^{1B}$ is C(O)—O—$C_{1-3}$alkyl.

In one especially preferred embodiment, $R^{1B}$ is —OH or $C_{1-3}$alkyl optionally substituted with 1, 2 or 3 (preferably 1) halogen (preferably F) or OH groups (for example $CH_2OH$).

In compounds of formula (I), when present, $R^{1C}$ may be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—S(O)$_2$—$C_{1-3}$alkyl optionally substituted with 1, 2 or 3 halogen or OH groups; —$C_{1-6}$alkyl-S(O)$_2$—O—$C_{1-3}$alkyl optionally substituted with 1, 2 or 3 halogen or OH groups; —$C_{1-6}$alkyl-O—S(O)$_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-S(O)$_2$—O-phenyl wherein said phenyl is optionally substituted with 1 $C_{1-3}$alkyl group and said $C_{1-3}$alkyl is optionally substituted with 1, 2 or 3 halogen; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; C(O)—O—$C_{1-6}$alkyl optionally substituted with 1, 2 or 3 halogen; —($CH_2CH_2O$)$_p$—$R^e$; —($CH_2CH_2O$)$_p$—$CH_2CH_2R^f$; and —($OCH_2CH_2$)$_p$—$R^f$.

$R^{1C}$ may also be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—S(O)$_2$—$C_{1-3}$alkyl optionally substituted with 1, 2 or 3 halogen or OH groups; —$C_{1-6}$alkyl-S(O)$_2$—O—$C_{1-3}$alkyl optionally substituted with 1, 2 or 3 halogen or OH groups; —$C_{1-6}$alkyl-O—S(O)$_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-S(O)$_2$—O-phenyl wherein said phenyl is optionally substituted with 1 $C_{1-3}$alkyl group and said $C_{1-3}$alkyl is optionally substituted with 1, 2 or 3 halogen; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —($CH_2CH_2O$)$_p$—$R^e$; —($CH_2CH_2O$)$_p$—$CH_2CH_2R^f$; and —($OCH_2CH_2$)$_p$—$R^f$.

More preferably, $R^{1C}$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—S(O)$_2$—$C_{1-3}$alkyl optionally substituted with 1, 2 or 3 halogen or OH groups; —$C_{1-6}$alkyl-S(O)$_2$—O—$C_{1-3}$alkyl optionally substituted with 1, 2 or 3 halogen or OH groups; —$C_{1-6}$alkyl-O—S(O)$_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-S(O)$_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—N($R^d$)$_2$; —O—$C_{1-6}$alkyl-C(O)—N($R^d$)$_2$; C(O)—O—$C_{1-6}$alkyl optionally substituted with 1, 2 or 3 halogen; —($CH_2CH_2O$)$_p$—$R^e$; —($CH_2CH_2O$)$_p$—$CH_2CH_2R^f$; and —($OCH_2CH_2$)$_p$—$R^f$.

$R^{1C}$ may also be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

Even more preferably, $R^{1C}$ is selected from the group consisting of hydrogen; OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen.

Also preferably, $R^{1C}$ is selected from the group consisting of hydrogen; OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In especially preferred embodiments, $R^{1C}$ is selected from the group consisting of hydrogen; OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen. $R^{1C}$ may also be selected from the group consisting of hydrogen; OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In another embodiment, $R^{1C}$ is selected from the group consisting of hydrogen; —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F); C(O)—$N(H)_2$; and C(O)—O—$C_{1-3}$alkyl optionally substituted with 1, 2 or 3 halogen (preferably F). $R^{1C}$ may also be selected from the group consisting of hydrogen; —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); and —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F).

In another embodiment, $R^{1C}$ is selected from the group consisting of hydrogen; —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and more preferably wherein $R^{1C}$ is selected from the group consisting of hydrogen; $C_{1-3}$alkyl optionally substituted with 1 OH group; C(O)—$N(H)_2$; and C(O)—O—$C_{1-3}$alkyl.

In another preferred embodiment, $R^{1C}$ is selected from the group consisting of hydrogen; OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^{1C}$ is selected from the group consisting of hydrogen; OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^{1C}$ is selected from the group consisting of hydrogen; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F); C(O)—$N(R^d)_2$; and C(O)—O—$C_{1-6}$alkyl optionally substituted with 1 halogen (preferably F).

In another preferred embodiment, $R^{1C}$ is selected from the group consisting of hydrogen; OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^{1C}$ is selected from the group consisting of hydrogen; OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^{1C}$ is selected from the group consisting of hydrogen; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F).

In another preferred embodiment, $R^{1C}$ is selected from the group consisting of hydrogen; halogen (preferably F); —OH; —$C_{1-6}$alkyl optionally substituted with 1, 2 or 3 (preferably 1) halogen (preferably F) or OH groups; —O—$C_{1-6}$alkyl optionally substituted with 1, 2 or 3 (preferably 1) halogen (preferably F) or OH groups; C(O)—N$(R^d)_2$; and C(O)—O—$C_{1-6}$alkyl optionally substituted with 1, 2 or 3 (preferably 1) halogen (preferably F).

In another preferred embodiment, $R^{1C}$ is selected from the group consisting of hydrogen; halogen (preferably F); —OH; —$C_{1-6}$alkyl optionally substituted with 1, 2 or 3 (preferably 1) halogen (preferably F) or OH groups; and —O—$C_{1-6}$alkyl optionally substituted with 1, 2 or 3 (preferably 1) halogen (preferably F) or OH groups.

In another embodiment, $R^{1C}$ is selected from the group consisting of halogen (preferably F); —OH; —$C_{1-6}$alkyl optionally substituted with 1, 2 or 3 (preferably 1) halogen (preferably F) or OH groups; and —O—$C_{1-6}$alkyl optionally substituted with 1, 2 or 3 (preferably 1) halogen (preferably F) or OH groups.

In a further preferred embodiment, $R^{1C}$ is hydrogen; —OH, $C_{1-3}$alkyl optionally substituted with 1, 2 or 3 (preferably 1) halogen (preferably F) or OH groups, C(O)—N$(H)_2$ or C(O)—O—$C_{1-3}$alkyl. For example, $R^{1C}$ is hydrogen. For example, $R^{1C}$ is OH. For example, $R^{1C}$ is —$C_{1-3}$alkyl optionally substituted with 1, 2 or 3 (preferably 1) halogen (preferably F). For example, $R^{1C}$ is C(O)—N$(H)_2$. For example, $R^{1C}$ is C(O)—O—$C_{1-3}$alkyl.

In an another embodiment, $R^{1C}$ is —OH, $C_{1-3}$alkyl optionally substituted with 1, 2 or 3 (preferably 1) halogen (preferably F) or OH groups, C(O)—N$(H)_2$ or C(O)—O—$C_{1-3}$alkyl For example, $R^{1C}$ is OH. For example, $R^{1C}$ is —$C_{1-3}$alkyl optionally substituted with 1, 2 or 3 (preferably 1) halogen (preferably F). For example, $R^{1C}$ is C(O)—N$(H)_2$. For example, $R^{1C}$ is C(O)—O—$C_{1-3}$alkyl.

In one especially preferred embodiment, $R^{1C}$ is hydrogen; —OH or $C_{1-3}$alkyl optionally substituted with 1, 2 or 3 (preferably 1) halogen (preferably F) or OH groups (for example $CH_2OH$).

In embodiments where $R^{1A}$ and $R^{1B}$ are present (i.e. embodiments wherein Z is

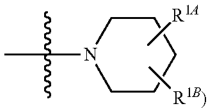

$R^{1A}$ and $R^{1B}$ may be the same group, or may be different groups. In certain embodiments, $R^{1A}$ and $R^{1B}$ are the same group, for example both $R^{1A}$ and $R^{1B}$ are —OH, or both $R^{1A}$ and $R^{1B}$ are $C_{1-3}$alkyl optionally substituted with 1, 2 or 3 (preferably 1) halogen (preferably F) or OH groups (for example $CH_2OH$). In certain embodiments, $R^{1A}$ and $R^{1B}$ are the different groups, for example $R^{1A}$ is OH and $R^{1B}$ is $C_{1-3}$alkyl optionally substituted with 1, 2 or 3 (preferably 1) halogen (preferably F) or OH groups (for example $CH_2OH$); or $R^{1B}$ is OH and $R^{1A}$ is $C_{1-3}$alkyl optionally substituted with 1, 2 or 3 (preferably 1) halogen (preferably F) or OH groups (for example $CH_2OH$).

In an especially preferred embodiment where $R^{1A}$ and $R^{1B}$ are present (i.e. embodiments wherein Z is

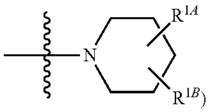

preferably $R^{1A}$ is selected from the group consisting of —$C_1$-6alkyl (for example —$C_{1-3}$alkyl) optionally substituted with 1, 2 or 3 (preferably 1) halogen (preferably F) or OH groups; C(O)—N$(H)_2$ or C(O)—O—$C_{1-3}$alkyl (preferably OH; or —$C_{1-3}$alkyl optionally substituted with 1, 2 or 3 (preferably 1) halogen (preferably F) or OH groups); and $R^{1B}$ is selected from the group consisting of —$C_{1-6}$alkyl (for example —$C_{1-3}$alkyl) optionally substituted with 1, 2 or 3 (preferably 1) halogen (preferably F) or OH groups; C(O)—N$(H)_2$ or C(O)—O—$C_{1-3}$alkyl (preferably OH; or —$C_{1-3}$alkyl optionally substituted with 1, 2 or 3 (preferably 1) halogen (preferably F) or OH groups).

In embodiments where $R^{1A}$ and $R^{1C}$ are present (i.e. embodiments wherein Z is selected from the group consisting of

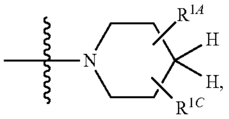

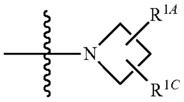

, and

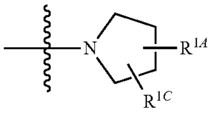

)

$R^{1A}$ and $R^{1C}$ may be the same group, or may be different groups. In certain embodiments, $R^{1A}$ and $R^{1C}$ are the same group, for example both $R^{1A}$ and $R^{1C}$ are —OH, or both $R^{1A}$ and $R^{1C}$ are $C_{1-3}$alkyl optionally substituted with 1, 2 or 3 (preferably 1) halogen (preferably F) or OH groups (for example $CH_2OH$). In certain embodiments, $R^{1A}$ and $R^{1C}$ are the different groups, for example $R^{1A}$ is OH and $R^{1C}$ is $C_{1-3}$alkyl optionally substituted with 1, 2 or 3 (preferably 1) halogen (preferably F) or OH groups (for example $CH_2OH$); $R^{1C}$ is OH and $R^{1C}$ is $C_{1-3}$alkyl optionally substituted with 1, 2 or 3 (preferably 1) halogen (preferably F) or OH groups (for example $CH_2OH$); $R^{1A}$ is OH and $R^{1C}$ is hydrogen; or $R^{1C}$ is hydrogen and $R^{1C}$ is $C_{1-3}$alkyl optionally substituted with 1, 2 or 3 (preferably 1) halogen (preferably F) or OH groups (for example $CH_2OH$).

In an especially preferred embodiment where $R^{1A}$ and $R^{1C}$ are present (i.e. embodiments wherein Z is selected from the group consisting of

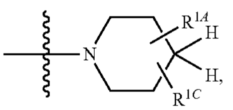

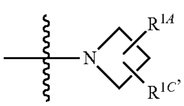

and

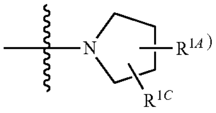

preferably $R^{1A}$ is selected from the group consisting of —$C_{1-6}$alkyl (for example —$C_{1-3}$alkyl) optionally substituted with 1, 2 or 3 (preferably 1) halogen (preferably F) or OH groups; C(O)—N(H)$_2$ or C(O)—O—$C_{1-3}$alkyl (preferably OH; or —$C_{1-3}$alkyl optionally substituted with 1, 2 or 3 (preferably 1) halogen (preferably F) or OH groups); and $R^{1C}$ is selected from the group consisting of hydrogen; —$C_{1-6}$alkyl (for example —$C_{1-3}$alkyl) optionally substituted with 1, 2 or 3 (preferably 1) halogen (preferably F) or OH groups; C(O)—N(H)$_2$ or C(O)—O—$C_{1-3}$alkyl (preferably hydrogen; OH; or —$C_{1-3}$alkyl optionally substituted with 1, 2 or 3 (preferably 1) halogen (preferably F) or OH groups).

In one preferred embodiment, Z is selected from the group consisting of:

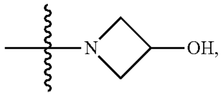 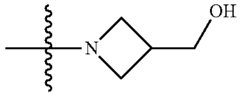 ,

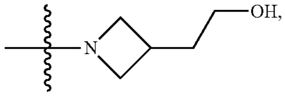 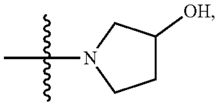

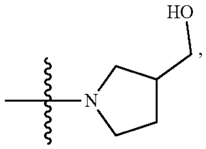 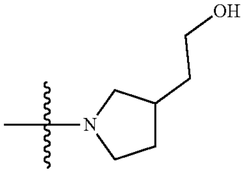 ,

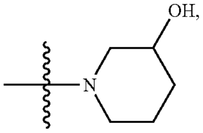 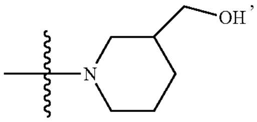

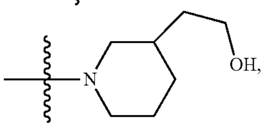 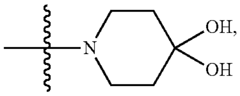

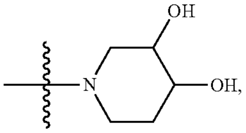 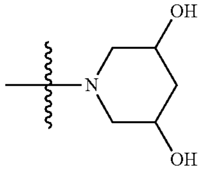 ,

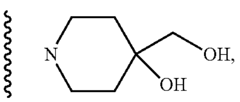 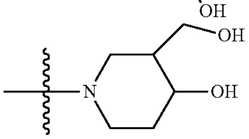 ,

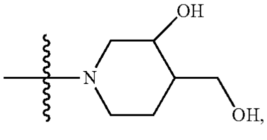 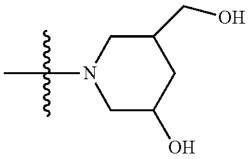 ,

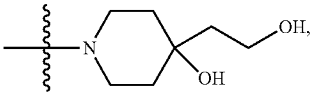

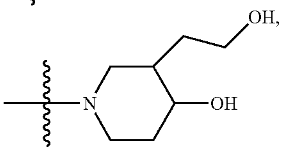

-continued

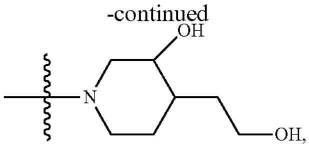

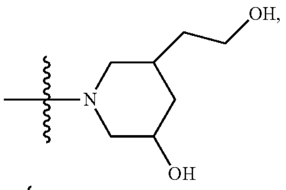

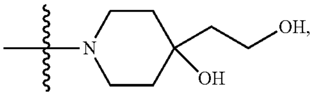

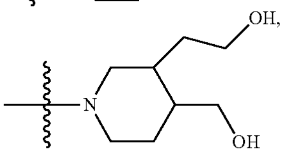

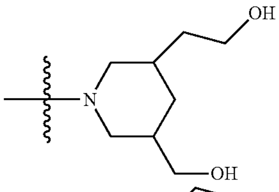 and

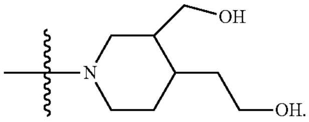

In one preferred embodiment, Z is selected from the group consisting of:

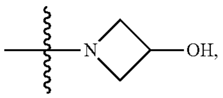 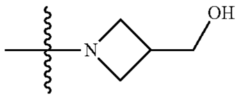 ,

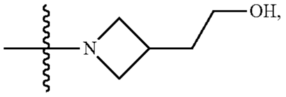

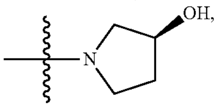 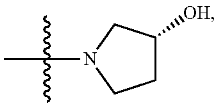

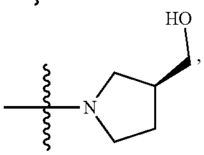 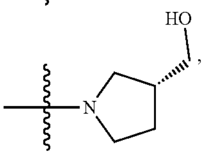

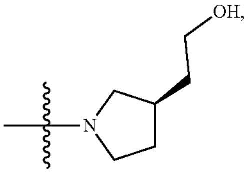 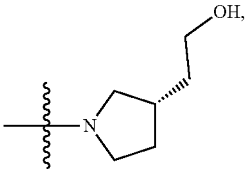

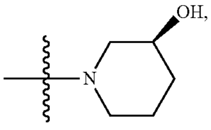 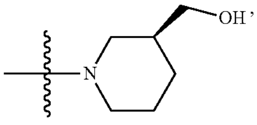

-continued
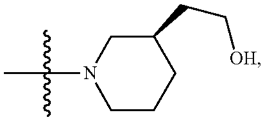
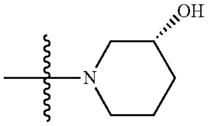
,
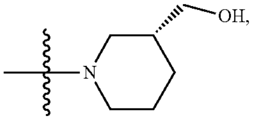
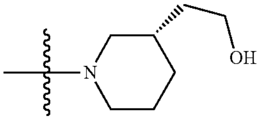
,
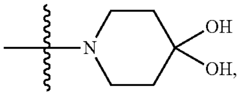
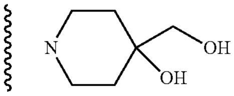
,
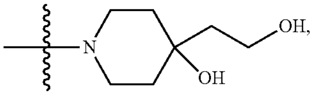
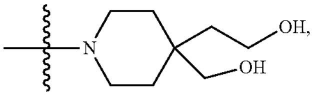
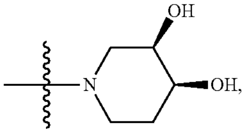
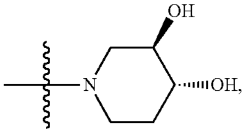
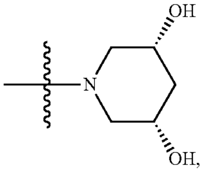
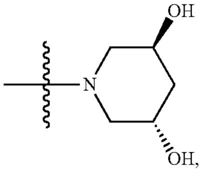
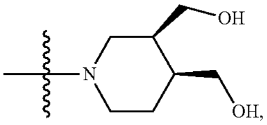
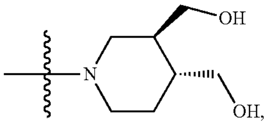
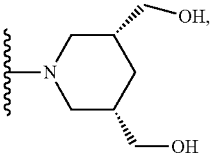
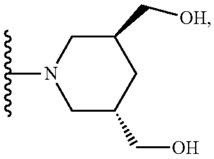
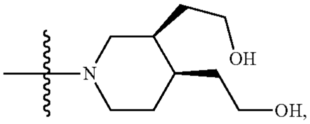
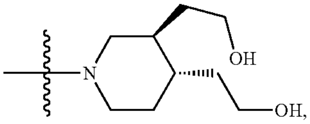
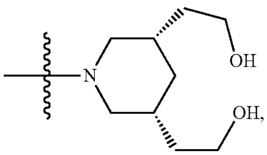
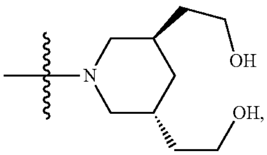
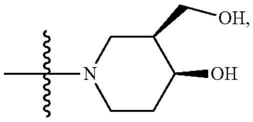
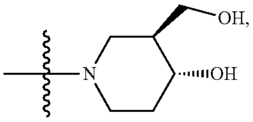
-continued
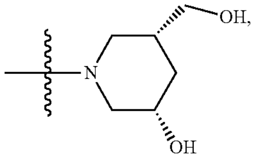
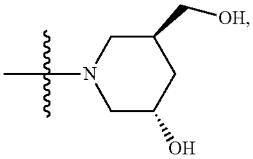
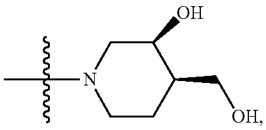
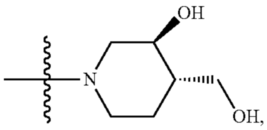
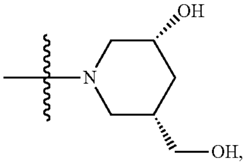
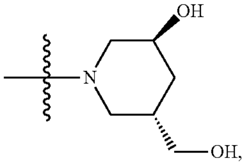
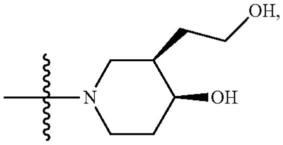
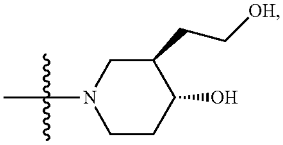
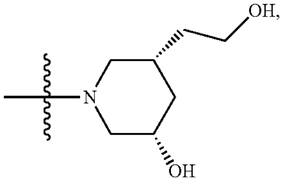
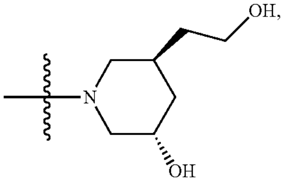
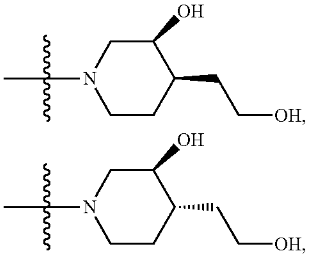
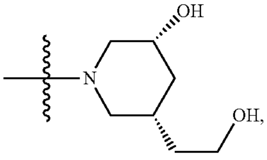
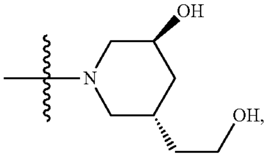
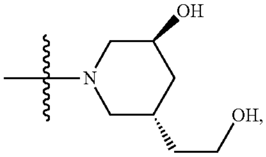
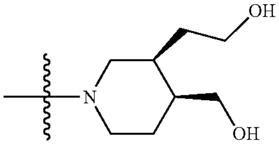
,
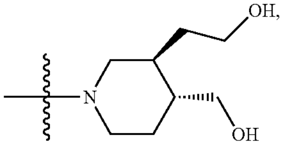
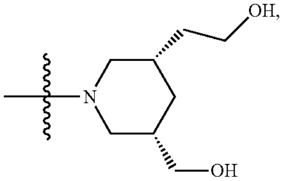
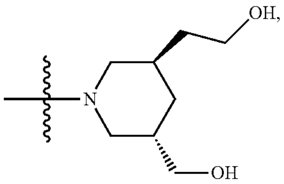

-continued

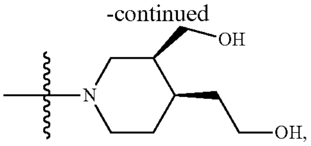

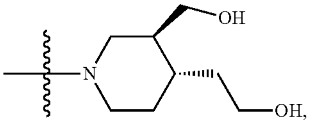

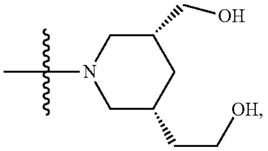

and

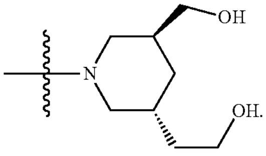

In one very preferred embodiment, Z is selected from the group consisting of:

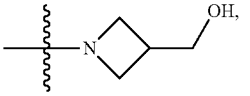 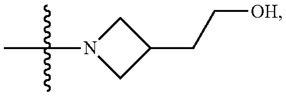

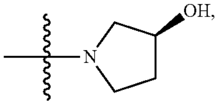 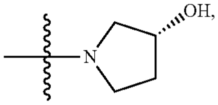

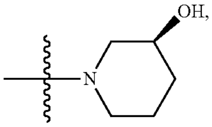 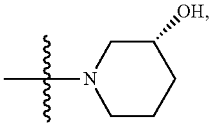

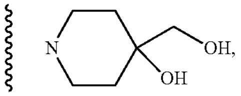 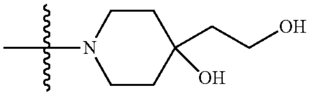 ,

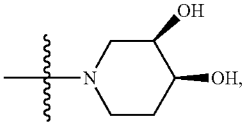 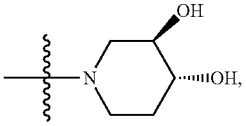

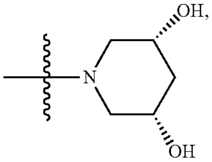 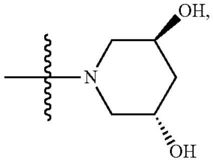

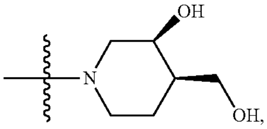

and

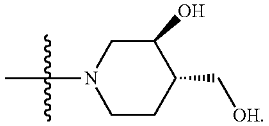

When present, each $R^2$ may be independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS—; $C_{1-6}$alkylS(═O); $C_{1-6}$alkylS($O_2$)—; $NO_2$; —N($R^a$)$_2$; —$C_{1-6}$alkylN($R^a$)$_2$; —N($R^a$)C(O)H; —N($R^a$)C(O)$C_{1-6}$alkyl optionally substituted with 1, 2 or 3 halogen; $CO_2H$; C(O)N($R^g$)$_2$; —$C_{1-6}$alkyl$CO_2H$; —$C_{1-6}$alkylC(O)N($R^g$)$_2$; and —($OCH_2CH_2$)$_p$—$R^f$ (for example —($OCH_2CH_2$)$_3$—F);

Preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS—; $C_{1-6}$alkylS(═O); $C_{1-6}$alkylS($O_2$)—; $NO_2$; —N($R^a$)$_2$; —$C_{1-6}$alkylN($R^a$)$_2$; —N($R^a$)C(O)H; —N($R^a$)C(O)$C_{1-6}$alkyl optionally substituted with 1, 2 or 3 halogen; C(O)N($R^g$)$_2$; —$C_{1-6}$alkylC(O)N($R^g$)$_2$; and —($OCH_2CH_2$)$_p$—$R^f$ (for example —($OCH_2CH_2$)$_3$—F);

Preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; —N($R^a$)C(O)H; —N($R^a$)C(O)$C_{1-6}$alkyl optionally substituted with 1, 2 or 3 halogen; $CO_2H$; C(O)N($R^g$)$_2$; —$C_{1-6}$alkyl$CO_2H$; —$C_{1-6}$alkylC(O)N($R^g$)$_2$; and —($OCH_2CH_2$)$_3$—$R^f$ (for example —($OCH_2CH_2$)$_3$—F);

More preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; $CO_2H$; C(O)N($R^g$)$_2$; —$C_{1-6}$alkyl$CO_2H$; and —$C_{1-6}$alkylC(O)N($R^g$)$_2$. Even more preferably, when present, each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; C(O)N($R^g$)$_2$; and —($OCH_2CH_2$)$_3$—F;

In one preferred embodiment, when present, each $R^2$ is independently selected from the group consisting of halogen; OH; CN; O—$C_{1-6}$alkyl optionally substituted with 1, 2 or 3 halogen or OH groups; C(O)—O—$C_{1-6}$alkyl optionally substituted with 1, 2 or 3 halogen; and C(O)N($R^g$)$_2$.

More preferably, when present, each $R^2$ is independently selected from the group consisting of halogen; OH; CN; O—$C_{1-3}$alkyl optionally substituted with 1, 2 or 3 halogen or OH groups; C(O)—O—$C_{1-3}$alkyl optionally substituted with 1, 2 or 3 halogen; C(O)N($R^g$)$_2$; and —($OCH_2CH_2$)$_3$—F. In such embodiments, when present, preferably $R^1$ is independently selected from the group consisting of H and $C_{1-6}$alkyl optionally substituted with 1 halogen, and more preferably $R^1$ is H; or, when present, $R^g$ is independently selected from the group consisting of H, $C_{1-6}$alkyl, and $C_{1-6}$alkyl substituted with 1 halogen (preferably F).

In an especially preferred embodiment, when present, each $R^2$ is independently selected from the group consisting of OH; O—$C_{1-6}$alkyl optionally substituted with 1, 2 or 3 halogen or OH groups; and C(O)N(H)$_2$. Even more preferably, each $R^2$ is independently selected from the group consisting of OH; O—$C_{1-3}$alkyl optionally substituted with 1 halogen; and C(O)N(H)$_2$. For example, each $R^2$ is independently selected from the group consisting of OH; O—$C_{1-3}$alkyl (preferably O-methyl); and C(O)N(H)$_2$.

In an especially preferred embodiment, when present, each $R^2$ is independently selected from the group consisting of OH and O—$C_{1-6}$alkyl optionally substituted with 1, 2 or 3 halogen (for example fluorine) or OH groups, and more preferably selected from the group consisting of OH and O—$C_{1-3}$alkyl optionally substituted with 1 halogen (for example fluorine) or OH group.

When present $R^3$ may be selected from the group consisting of halogen (e.g. F, Br, Cl, or I); OH; $C_{1-6}$alkyl optionally substituted with 1, 2 or 3 halogen (preferably 1, 2 or 3 fluorine); and —$OC_{1-6}$alkyl optionally substituted with 1, 2 or 3 halogen (preferably 1, 2 or 3 fluorine). Preferably, $R^3$ is selected from the group consisting of halogen (e.g. F, Br, Cl, or I); OH; $C_{1-3}$alkyl optionally substituted with 1, 2 or 3 halogen (preferably 1, 2 or 3 fluorine). More preferably, $R^3$ is selected from the group consisting of halogen (e.g. F, Br, Cl, or I); $C_{1-3}$alkyl optionally substituted with 1, 2 or 3 halogen (preferably 1, 2 or 3 fluorine) (for example $CH_2F$, $CHF_2$ or $CF_3$) and O—$C_{1-3}$alkyl optionally substituted with 1, 2 or 3 halogen (preferably 1, 2 or 3 fluorine) (for example $PCH_2F$, $PCHF_2$ or $PCF_3$). Even more preferably, $R^3$ is selected from the group consisting of halogen and —$OC_{1-6}$alkyl optionally substituted with 1 halogen (for example —$OCH_3$ or —$OCH_2F$). Most preferably, $R^3$ is halogen, and especially F.

When present $R^a$, $R^b$, $R^c$ and $R^d$ may each independently be selected from the group consisting of H and $C_{1-6}$alkyl optionally substituted with 1, 2 or 3 halogen. Preferably, $R^a$, $R^b$, $R^c$ and $R^d$ are each independently selected from the group consisting of H and $C_{1-3}$alkyl optionally substituted with 1, 2 or 3 halogen (preferably F). In one embodiment, $R^a$, $R^b$, $R^c$ and $R^d$ may each independently be selected from the group consisting of H and $C_{1-3}$alkyl (i.e. unsubstituted $C_{1-3}$alkyl). In another embodiments, $R^a$, $R^b$, $R^c$ and $R^d$ are each independently selected from the group consisting of H and $C_{1-3}$alkyl optionally substituted with 1 halogen (preferably F).

In one preferred embodiment, when present, $R^1$ is preferably H or $C_{1-3}$alkyl, and more preferably $R^1$ is H.

In one preferred embodiment, when present each $R^d$ is independently selected from the group consisting of H and $C_{1-3}$alkyl optionally substituted with 1 halogen (preferably F), and more preferably each $R^d$ is H.

When present, $R^e$ is selected from the group consisting of H and $C_{1-6}$alkyl optionally substituted with 1, 2 or 3 halogens. Preferably, $R^e$ is selected from the group consisting of H and $C_{1-3}$alkyl optionally substituted with 1, 2 or 3 halogens. More preferably, $R^e$ is selected from the group consisting of H and $C_{1-3}$alkyl optionally substituted with 1 halogen (preferably F).

When present, $R^f$ may be selected from the group consisting of H; halogen; —$CH_2$(halogen), —CH(halogen)$_2$, —C(halogen)$_3$ and OH. Preferably, $R^f$ is selected from the group consisting of H; halogen and OH. More preferably, $R^f$ is selected from the group consisting of H and halogen (preferably F).

When present, each $R^g$ may be independently selected from the group consisting of H, $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with 1 —$OS(O)_2CH_3$ group; and $C_{1-6}$alkyl substituted with 1 —$S(O)_2OCH_3$ group. Preferably, when present, each $R^g$ may be independently selected from the group consisting of H, $C_{1-6}$alkyl, $C_{1-6}$alkyl substituted with 1 halogen (preferably F); $C_{1-6}$alkyl substituted with 1 OH group; $C_{1-6}$alkyl substituted with 1 —$OC_{1-3}$alkyl group; $C_{1-6}$alkyl substituted with a —$OS(O)_2CH_3$ group; and $C_{1-6}$alkyl substituted with a —$S(O)_2OCH_3$ group. For example, when present, each $R^g$ may be independently selected from the group consisting of H, $C_{1-6}$alkyl, and $C_{1-6}$alkyl substituted with 1 halogen (preferably F); or selected from the group consisting of H, and $C_{1-6}$alkyl.

In one preferred embodiment, when present, one $R^g$ is H, and the second $R^g$ is selected from the group consisting of $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group. In another preferred embodiment, when present, one $R^g$ is $C_{1-6}$alkyl, and the second $R^g$ is selected from the group consisting of H, $C_{1-6}$alkyl, $C_{1-6}$alkyl substituted with 1, 2 or 3 halogen (preferably F); $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group. For example, when present one $R^g$ is H, and the second $R^g$ is selected from the group consisting of $C_{1-6}$alkyl, $C_{1-6}$alkyl substituted with 1, 2 or 3 halogen (preferably F); and $C_{1-6}$alkyl substituted with 1, 2 or 3 OH groups. Or, for example, when present, both $R^g$ groups (i.e. both groups of an "$(R^g)_2$") are $C_{1-6}$alkyl, or both are $C_{1-6}$alkyl substituted with 1, 2 or 3 halogen (preferably F); or both are $C_{1-6}$alkyl substituted with 1, 2 or 3 OH groups.

p may be 2, 3, 4, 5, 6, 7 or 8. Alternatively, in certain embodiments, p may be 1, 2, 3, 4, 5, 6, 7 or 8. Preferably, p is 3, 4, 5 or 6, and more preferably p is 3, 4 or 5. In certain preferred embodiments, p is 3.

In certain preferred embodiments, the compound of formula (I) has the formula (Ia)

(Ia)

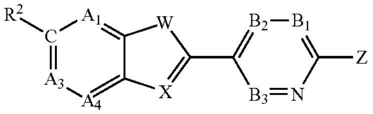

In such embodiments, preferably $A_1$, $A_3$, and $A_4$ are independently selected from the group consisting of N and CH, and at least one of $A_1$, $A_3$, and $A_4$ is CH (and preferably wherein each of $A_1$ and $A_4$ is CH, and $A_3$ is N or CH). In certain preferred embodiments, each of $A_1$, $A_3$, and $A_4$ is CH. In certain preferred embodiments, $A_1$ is N and $A_4$ is CH, and $A_3$ is N or CH; and even more preferably $A_1$ is N and $A_4$ is CH, and $A_3$ is N.

In embodiments wherein the compound of formula (I) is a compound of formula (Ia), especially preferably, W is S and X is N. Also preferably in embodiments wherein the compound of formula (I) is a compound of formula (Ia), W is NH and X is CH.

In embodiments wherein the compound of formula (I) is a compound of formula (Ia), preferably $R^2$ is selected from the group consisting of OH; O—$C_{1-6}$alkyl optionally substituted with 1, 2 or 3 halogen or OH groups; $C(O)N(R^g)_2$ (for example $C(O)N(H)_2$); and —$(OCH_2CH_2)_p$—$R^f$ (for example —$(OCH_2CH_2)_3$—F). More preferably, $R^2$ is selected from the group consisting of OH; O—$C_{1-3}$alkyl optionally substituted with 1 halogen (for example fluorine) or OH group); $C(O)N(H)_2$; and —$(OCH_2CH_2)_3$—F. Even more preferably $R^2$ is selected from the group consisting of OH and $C(O)N(H)_2$; or $R^2$ is independently selected from the group consisting of OH and O—$C_{1-3}$alkyl optionally substituted with 1 halogen (for example fluorine) or OH group).

In another preferred embodiment wherein the compound of formula (I) is a compound of formula (Ia), $A_1$, $A_3$, and $A_4$ are each CH. Especially preferably $R^2$ is H or O—$C_{1-6}$alkyl optionally substituted with 1, 2 or 3 halogen or OH groups. Also preferably, W is S and X is N. Also preferably, $B_1$, $B_2$ and $B_3$ are each CH.

In another preferred embodiment wherein the compound of formula (I) is a compound of formula (Ia), $A_1$ is N, $A_4$ is CH, and $A_3$ is N or CH; and even more preferably where $A_1$ is N, $A_4$ is CH, and $A_3$ is N. Especially preferably $R^2$ is H or O—$C_{1-6}$alkyl optionally substituted with 1, 2 or 3 halogen or OH groups. Also preferably, W is S and X is N, or W is NH and X is CH, and even more preferably W is NH and X is CH. Also preferably, $B_1$, $B_2$ and $B_3$ are each CH; or $B_1$ and $B_2$ are CH and $B_3$ is $CR^3$ (and more preferably or $B_1$ and $B_2$ are CH and $B_3$ is $CR^3$).

In certain preferred embodiments, the compound of formula (I) has the formula (Ib)

(Ib)

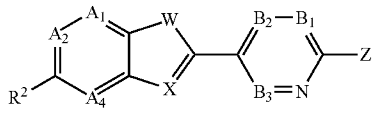

In such embodiments, preferably $A_1$, $A_2$, and $A_4$ are independently selected from the group consisting of N and CH, and at least one of $A_1$, $A_2$, and $A_4$ is CH (and preferably wherein each of $A_1$ and $A_4$ is CH, and $A_2$ is N or CH). In certain preferred embodiments, each of $A_1$, $A_2$, and $A_4$ is CH.

In embodiments wherein the compound of formula (I) is a compound of formula (Ib), especially preferably, W is S and X is N. Also preferably in embodiments wherein the compound of formula (I) is a compound of formula (Ib), W is NH and X is CH.

In embodiments wherein the compound of formula (I) is a compound of formula (Ib), preferably $R^2$ is OH; O—$C_{1-6}$alkyl optionally substituted with 1, 2 or 3 halogen or OH groups; or $C(O)N(R^g)_2$ (for example $C(O)N(H)_2$). More preferably, $R^2$ is selected from the group consisting of OH; O—$C_{1-3}$alkyl optionally substituted with 1 halogen; and $C(O)N(H)_2$. Even more preferably each $R^2$ is independently selected from the group consisting of OH and 0-$C_{1-3}$alkyl (preferably O-methyl). Also very preferably each $R^2$ is independently selected from the group consisting of OH and O—$C_{1-3}$alkyl optionally substituted with 1 halogen (for example fluorine).

In another preferred embodiment wherein the compound of formula (I) is a compound of formula (Ib), and each of $A_1$, $A_2$, and $A_4$ is CH. Especially preferably $R^2$ is selected from the group consisting of OH and O—$C_{1-3}$alkyl optionally substituted with 1 halogen. Also preferably, W is S and X is N or W is NH and X is CH, and even more preferably W is NH and X is CH. Also preferably, $B_1$, $B_2$ and $B_3$ are each CH; or $B_1$ and $B_2$ are CH and $B_3$ is $CR^3$; or $B_1$ is N and $B_2$ and $B_3$ are each CH (and more preferably or $B_1$ and $B_2$ are CH and $B_3$ is $CR^3$ or $B_1$ is N and $B_2$ and $B_3$ are each CH).

The present invention also provides compounds of formula (X):

(X)

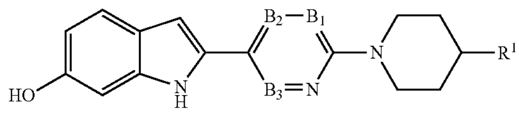

Aspects and embodiments, including preferred embodiments, described above for formula (I) in respect of the following groups are equally applicable as aspects and embodiments, including preferred embodiments, for compounds of formula (X): $B_1$, $B_2$, $B_3$, $R^3$, $R^b$, $R^c$ and $R^d$, $R^e$, $R^f$, and p.

In compounds of formula (X), $R^1$ may be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^1$ may also be selected from the group consisting of hydrogen; halogen; —OH; —CN; —$C_{1-6}$alkyl optionally substituted with 1, 2 or 3 halogen or OH groups; —O —$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

More preferably, $R^1$ is selected from the group consisting of hydrogen; halogen; —OH; —CN; —$C_{1-6}$alkyl optionally substituted with 1, 2 or 3 halogen or OH groups; —O —$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; C(O)—O—$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$.

$R^1$ may also be selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-C(O)—$N(R^d)_2$; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$.

Even more preferably, $R^1$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen.

Also preferably, $R^1$ is selected from the group consisting of OH; —$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

In especially preferred embodiments, $R^1$ is selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; C(O)—$N(R^d)_2$; and C(O)—O—$C_{1-6}$alkyl optionally substituted with 1, 2 or 3 halogen. $R^1$ may also be selected from the group consisting of OH; —$C_{1-6}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; and —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen.

Even more preferably, $R^1$ is selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F); C(O)—$N(H)_2$; and C(O)—O—$C_{1-3}$alkyl optionally substituted with 1, 2 or 3 halogen (preferably F). $R^1$ may also be selected from the group consisting of —$C_{1-3}$alkyl optionally substituted with 1, 2 or 3 halogen (preferably F) or OH groups; —$C_{1-3}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen (preferably F); and —$C_{1-3}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen (preferably F).

In certain very preferred embodiments, $R^1$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and more preferably wherein $R^1$ is selected from the group consisting of $C_{1-3}$alkyl optionally substituted with 1 OH group; C(O)—$N(H)_2$; and C(O)—O—$C_{1-3}$alkyl.

In another preferred embodiment, $R^1$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^1$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^1$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F); C(O)—$N(R^d)_2$; and C(O)—O—$C_{1-6}$alkyl optionally substituted with 1 halogen (preferably F).

In another preferred embodiment, $R^1$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); and —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F). For example, $R^1$ is selected from the group consisting of OH; —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group; or, for example, $R^1$ is selected from the group consisting of —$C_{1-2}$alkyl optionally substituted with 1 halogen (preferably F) or OH group; and —$C_{1-2}$alkyl-O—$S(O)_2$-phenyl wherein said phenyl is optionally substituted with 1 $C_1$alkyl group and said $C_1$alkyl optionally substituted with 1 halogen (preferably F).

In another preferred embodiment, $R^1$ is selected from the group consisting of halogen (preferably F); —OH; —$C_{1-6}$alkyl optionally substituted with 1, 2 or 3 (preferably 1) halogen (preferably F) or OH groups; —O—$C_{1-6}$alkyl optionally substituted with 1, 2 or 3 (preferably 1) halogen (preferably F) or OH groups; C(O)—$N(R^d)_2$; and C(O)—O—$C_{1-6}$alkyl optionally substituted with 1, 2 or 3 (preferably 1) halogen (preferably F).

In another preferred embodiment, $R^1$ is selected from the group consisting of halogen (preferably F); —OH; —$C_{1-6}$alkyl optionally substituted with 1, 2 or 3 (preferably 1) halogen (preferably F) or OH groups; and —O —$C_{1-6}$alkyl optionally substituted with 1, 2 or 3 (preferably 1) halogen (preferably F) or OH groups.

In a further preferred embodiment, $R^1$ is —$C_{1-3}$alkyl optionally substituted with 1, 2 or 3 (preferably 1) halogen (preferably F) or OH groups, C(O)—$N(H)_2$ or C(O)—O—$C_{1-3}$alkyl.

In a further preferred embodiment, $R^1$ is —$C_{1-3}$alkyl optionally substituted with 1, 2 or 3 (preferably 1) halogen (preferably F) or OH. In a further preferred embodiment, $R^1$ is C(O)—$N(H)_2$. In a further preferred embodiment, $R^1$ is C(O)—O—$C_{1-3}$alkyl.

In an especially preferred embodiment, $R^1$ is —$CH_2OH$

Preferred compounds of the invention are Example Compounds 1 to 22 and 23 to 34 (for example, Example Compounds 1 to 8, 11, 12, 14, 18 and 21 to 34), described in the Examples section below.

In the compounds of the invention, one or more of the atoms may be an isotope. In the compounds of the invention, one or more of the atoms may be a radiolabeled atom (which may also be referred to as a radioisotope), for example one, two or three of the atoms may be a radiolabeled atom. In particular, one or more of the atoms of $R^1$, $R^2$, $R^3$ and/or $R^e$ may be a radiolabeled atom. A radiolabeled atom may be selected from the group consisting of $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^3H$, $^{11}C$, $^{14}C$, $^{13}N$, $^{15}O$, $^{18}F$, $^{19}F$, $^{120}I$, $^{123}I$ and $^{125}I$, more preferably $^3H$, $^{11}C$, $^{13}N$, $^{15}O$, $^{18}F$, $^{120}I$, $I^{123}$, and $^{125}I$, even more preferably $^{11}C$, $^{13}N$, $^{15}O$, and $^{18}F$, and most preferably $^{18}F$ and $^{11}C$.

Depending upon the substituents present in compounds of the invention, the compounds may form esters, amides, carbamates and/or salts. Salts of compounds of the invention which are suitable for use in medicine are those wherein a counter-ion is pharmaceutically acceptable. However, salts having non-pharmaceutically acceptable counter-ions are within the scope of the present invention, for example, for use as intermediates in the preparation of the compounds of the invention and their pharmaceutically acceptable salts, and physiologically functional derivatives. By the term "physiologically functional derivative" is meant a chemical derivative of a compound of the invention having the same physiological function as the free compound of the invention, for example, by being convertible in the body thereto. Esters, amides and carbamates are examples of physiologically functional derivatives.

Suitable salts according to the invention include those formed with organic or inorganic acids or bases. In particular, suitable salts formed with acids include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, hydroiodic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine. Other acids such as oxalic, while not in themselves pharmaceutically acceptable, may be useful as intermediates in obtaining the compounds of the invention and their pharmaceutical acceptable acid addition salts.

Compounds of the invention may have an appropriate group converted to an ester, an amide or a carbamate. Typical ester and amide groups formed from an acid group in the compound of the invention include —$COOR^h$, —$CONR^h_2$, —$SO_2OR^h$, or —$SO_2N(R^h)_2$, while typical ester and amide and carbamate groups formed from an —OH or a basic nitrogen of an aromatic heterocycle in the compound of the invention include —$OC(O)R^h$, —$NC(O)R^h$, —$NCO_2R^h$, —$OSO_2R^h$, and —$NSO_2R^h$, where $R^h$ is selected from the group consisting of $C_{1-8}$alkyl, $C_{2-8}$alkenyl, $C_{2-8}$alkynyl, $C_{3-8}$cycloalkyl and $C_{3-8}$cycloalkyl$C_{1-8}$alkyl, halo$C_{1-8}$alkyl, dihalo$C_{1-8}$alkyl, trihalo$C_{1-8}$alkyl, phenyl and phenyl$C_{1-3}$alkyl; more preferably $R^h$ is selected from the group consisting of $C_{1-6}$alkyl, $C_{2-6}$alkenyl, $C_{2-6}$alkynyl, $C_{3-8}$cycloalkyl and $C_{3-8}$cycloalkyl$C_{1-6}$alkyl.

Those skilled in the art of organic chemistry will appreciate that many organic compounds can form complexes with solvents in which they are reacted or from which they are precipitated or crystallized. These complexes are known as "solvates". For example, a complex with water is known as a hydrate. Solvates, such as hydrates, exist when the drug substance incorporates solvent, such as water, in the crystal lattice in either stoichiometric or non-stoichiometric amounts. Drug substances are routinely screened for the existence of hydrates since these may be encountered at any stage of the drug manufacturing process or upon storage of the drug substance or dosage form. Solvates are described in S. Byrn et al, Pharmaceutical Research 12(7), 1995, 954-954, and Water-Insoluble Drug Formulation, $2^{nd}$ ed. R. Liu, CRC Press, page 553, which are incorporated herein by reference. Accordingly, it will be understood by the skilled person that the compounds of the invention, as well as esters, amides, carbamates and/or salts thereof may therefore be present in the form of solvates. Solvates of compounds of the invention which are suitable for use in medicine are those wherein the associated solvent is pharmaceutically acceptable. For example, a hydrate is an example of a pharmaceutically acceptable solvate. However, solvates having non-pharmaceutically acceptable associated solvents may find use as intermediates in the preparation of the compounds of the invention and their pharmaceutically acceptable esters, amides, carbamates and/or salts thereof.

A compound which, upon administration to the recipient, is capable of being converted into a compound of the invention as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

The following definitions apply to the terms as used throughout this specification, unless otherwise limited in specific instances.

As used herein, the term "alkyl" means both straight and branched chain saturated hydrocarbon groups. Examples of alkyl groups include methyl, ethyl, n-propyl, iso-propyl, n-butyl, t-butyl, i-butyl, sec-butyl, pentyl and hexyl groups. Among unbranched alkyl groups, these are preferably methyl, ethyl, n-propyl, n-butyl groups. Among branched alkyl groups, there may be mentioned isopropyl, tertbutyl, isobutyl, 1-ethylpropyl and 1-ethylbutyl groups.

As used herein, the term "halogen" or "halo" means fluorine (F), chlorine (Cl), bromine (Br), or iodine (I).

Labeled Compounds of the Invention

Compounds of the invention may be labeled. A "label" (which may be a radiolabel or other detectable label, or a tag, marker, detectable marker, tracer, radiotracer or equivalent) is any atom or group suitable for imaging and/or assaying (for example, identifying, imaging, diagnosing, evaluating, detecting and/or quantitating) in vivo or in vitro, and in particular imaging and diagnosing. Suitable labels include, for example, radioisotopes (which may also be referred to as "radiolabeled atoms"), radionuclides, isotopes, positron emitters, gamma emitters, fluorescent groups, luminescent groups, chromogenic groups, biotin (in conjunction with streptavidin complexation) or photoaffinity groups. The type of label chosen will depend on the desired detection method. The position at which the label is integrated or attached to the compounds of the present invention is not particularly limited.

Examples of isotopes (such as radioisotopes, radionuclides, positron emitters and gamma emitters) which may be used to label compounds of the invention, include but are not limited to: $^{2}H$, $^{3}H$, $^{11}C$, $^{13}C$, $^{14}C$, $^{13}N$, $^{15}O$, $^{18}F$, $^{19}F$, $^{75}Br$, $^{76}Br$, $^{77}Br$, $^{120}I$, $^{123}I$, $^{124}I$, $^{125}I$ and $^{131}I$; preferably $^{2}H$, $^{3}H$, $^{11}C$, $^{13}N$, $^{15}O$, $^{18}F$, $I^{120}$, $I^{123}$ and $I^{125}$; more preferably $^{11}C$, $^{13}N$, $^{15}O$, $^{18}F$, $I^{120}$, and $I^{123}$; and even more preferably $^{18}F$.

Isotopic form (which also may be referred to as "isotopic variants") of the compounds of the invention can generally be prepared by conventional procedures such as by the methods described in the Examples section using appropriate isotopic variations of suitable reagents that are commercially available or prepared by known synthetic techniques. Radioisotopes, radionuclides, positron emitters and gamma emitters can be included into the compounds of the present invention by methods which are routine in the field of organic chemistry. For example, they may be introduced by using a correspondingly labeled starting material when the desired compound of the present invention is prepared. Illustrative methods of introducing detectable labels are described, for instance, in US 2012/0302755.

In certain preferred embodiments, compounds of the invention are labeled. In the compounds of the invention, one or more H, one or more C, one or more N, one or more O, one or more F, one or more Br, and/or one or I may be replaced with a $^{3}H$; $^{11}C$, $^{13}C$ or $^{14}C$; $^{13}N$; $^{15}O$; $^{18}F$ or $^{19}F$; $^{75}Br$ or $^{76}Br$; $^{120}I$, $^{123}I$, $^{125}I$ or $^{131}I$, respectively. Preferably one or more C, one or more N, one or more O, one or more F, and/or one or I may be replaced with a $^{11}C$ or $^{14}C$; $^{13}N$; $^{15}O$; $^{18}F$ or $^{19}F$; $^{120}I$, $^{123}I$ or $^{125}I$, respectively; and more preferably $^{11}C$, $^{13}N$, $^{15}O$, $^{8}F$ and $^{120}I$ respectively.

$^{11}C$, $^{13}N$, $^{15}O$, $^{18}F$ and $^{120}I$ are radioactive isotopes. They decay mainly by positron emission. Therefore, the inclusion of such atoms in a compound of the invention makes the compound detectable by positron emission tomography. As such, compounds of the invention comprising one or more $^{11}C$, $^{13}N$, $^{15}O$, $^{18}F$ or $^{120}I$ are especially useful as a radioactive tracers, also referred to as a radioactive ligands, for positron emission tomography (PET).

In the compounds of the invention, one or more I may be replaced with an $^{123}I$ radioactive isotope. The inclusion of such an atom in a compound of the invention makes the compound detectable by single-photon emission computed tomography (SPECT). As such compounds of the invention comprising one or more $^{123}I$ are especially useful as a radioactive tracers for SPECT.

In the compounds of the invention, one or more H may be replaced with an $^{3}H$ radioactive isotope. The inclusion of such an atom in a compound of the invention makes the compound detectable by autoradiography or liquid scintillation counting. Compounds of the invention comprising one or more $^{3}H$ are especially useful as a radioactive tracers for in vitro studies.

In the compounds of the invention, one or more I may be replaced with an $^{125}I$ radioactive isotope. The inclusion of such an atom in a compound of the invention makes the compound detectable by autoradiography, gamma-counter crystal detectors, scintigraphy, gamma imaging, and SPECT. Compounds of the invention comprising one or more $^{125}I$ are especially useful as a radioactive tracers for in vitro studies and in vitro SPECT.

In certain preferred embodiments, labeled compounds of the invention may be labeled so that they may be detected in vivo using in vivo magnetic resonance spectroscopy (MRS), magnetic resonance imaging, PET, single-photon SPECT and combinations thereof. For example, a compound of the invention may be labeled with $^{19}F$ or $^{13}C$ for MRS/MRI; may be radiolabeled with $C^{11}$, $N^{13}$, $O^{15}$, $F^{18}$ or $I^{120}$ for PET imaging; or may be radiolabeled with $^{1123}$ or $^{1125}$ for SPECT. Preferably the compounds of the invention comprise one or more radioisotopes selected from $C^{11}$, $N^{13}$, $O^{15}$, $F^{18}$ and $I^{120}$.

The compounds of the invention comprise a number of C atoms. One or more C in a compound of the invention may be replaced with a $^{11}C$. For example, one C is replaced with one $^{11}C$; or two C are replaced with two $^{11}C$; or three C are replaced with three $^{11}C$. Preferably, one C is replaced with one $^{11}C$.

The compounds of the invention comprise one or more N. One or more N in a compound of the invention may be replaced with a $^{13}N$. For example, one N is replaced with a $^{13}N$; or (if present) two N are replaced with two $^{13}N$; or (if present) three N are replaced with three $^{13}N$. Preferably, if one at least one N is present in the compound of the invention, one N is replaced with a $^{13}N$.

For compounds of the invention comprising one or more O, one or more O in the compound may be replaced with an $^{15}O$. For example, (if present) one O is replaced with an $^{15}O$; or (if present) two O are replaced with two $^{15}O$; or (if present) three O are replaced with three $^{15}O$. Preferably, if one at least one O is present in the compound of the invention, one O is replaced with an $^{15}O$.

For compounds of the invention comprising one or more F, one or more F in the compound may be replaced with a $^{18}F$. For example, (if present) one F is replaced with a $^{18}F$; or (if present) two F are replaced with two $^{18}F$; or (if present) three F are replaced with three $^{18}F$. Preferably, if at least one F is present in the compound of the invention, one F is replaced with a $^{18}F$. Preferably one F is replaced with one $^{18}F$.

For compounds of the invention comprising one or more 1, one or more I in the compound may be replaced with an $^{120}I$. For example, (if present) one I is replaced with an $^{120}I$; or (if present) two I are replaced with two $^{120}I$; or (if present) three I are replaced with three $^{120}I$. Preferably, if at least one I is present in the compound of the invention, one I is replaced with an $^{120}I$.

Alternatively, or additionally, for compounds of the invention comprising one or more I, one or more I in the compound may alternatively be replaced with an $^{123}I$ or $^{125}I$. For example, (if present) one I is replaced with an $^{123}I$ or $^{125}I$; or (if present) two I are replaced with two $^{123}I$ or two $^{125}I$; or (if present) three I are replaced with three $^{123}I$ or three $^{125}I$. Preferably, if at least one I is present in the compound of the invention, one I is replaced with an $^{123}I$ or $^{125}I$.

The compounds of the invention comprise a number of H atoms. One or more H in a compound of the invention may be replaced with a $^{3}H$. For example, one H is replaced with one $^{3}H$; or two H are replaced with two $^{3}H$; or three H are replaced with three $^{3}H$, or at least three H are replaced with at least three $^{3}H$. Preferably one H is replaced with one $^{3}H$.

Uses of Compounds of the Invention

The present invention provides compounds that are selective tau deposit/aggregate ligands. The terms "tau deposit ligand" and "tau aggregate ligand" as used herein are intended to cover any moiety which binds to a tau deposit (a tau deposit may also be referred to as a tau aggregate). For example, the compounds of the present invention may bind to one or more of: pathologically aggregated tau, hyperphosphorylated tau, neurofibrillary tangles, paired helical filaments, straight filaments, neurotoxic soluble oligomers, polymers and fibrils. The compounds of the present invention are particularly suitable for binding to various types of tau deposits (i.e. tau aggregates). In particular, the compounds of the invention are suitable for binding to tau deposits comprising 4R isomer forms of tau (i.e. tau aggregates comprising 4R isomer forms of tau).

Preferred compounds of the present invention have excellent binding affinity for tau deposits. For example, preferably compounds of the invention have an $IC_{50}$ value for tau deposits in a competitive binding assay that is less than 100 nM, preferably less than 70 nM, preferably less than 60 nM, more preferably less than 55 nM, more preferably less than 50 nM, more preferably less than 40 nM, more preferably less than 30 nM, more preferably less than 25 nM, more preferably less than 20 nM, and even more preferably less than 15 nM, for example less than 13 nM, less than 10 nM, less than 8 nM, less than 6 nM, less than 5 nM, less than 4 nM, less than 3 nM, or less than 2 nM. In one preferred embodiment, compounds of the invention have an $IC_{50}$ value for tau deposits of less than 70 nM in a competitive binding assay. In another preferred embodiment, compounds of the invention have an $IC_{50}$ value for tau deposits of less than 50 nM in a competitive binding assay. In another preferred embodiment, compounds of the invention have an $IC_{50}$ value for tau deposits of less than 30 nM in a competitive binding assay. In another preferred embodiment, compounds of the invention have an $IC_{50}$ value for tau deposits of less than 20 nM in a competitive binding assay. In another preferred embodiment, compounds of the invention have an $IC_{50}$ value for tau deposits of less than 15 nM in a competitive binding assay. In another preferred embodiment, compounds of the invention have an $IC_{50}$ value for tau deposits of less than 10 nM in a competitive binding assay. In another preferred embodiment, compounds of the invention have an $IC_{50}$ value for tau deposits of less than 5 nM in a competitive binding assay. In another preferred embodiment, compounds of the invention have an $IC_{50}$ value for tau deposits of less than 3 nM in a competitive binding assay. It is especially preferred that compounds of the invention have an $IC_{50}$ value for tau deposits of less than 10 nM in a competitive binding assay Preferred compounds of the present invention, as well as having excellent binding affinity for tau deposits (for example binding for tau at a level described above in a competitive binding assay), are selective tau deposit ligands. "Selective", in this context, means any tau deposit ligand that binds to a tau deposit in preference to an Aβ deposit. For example, preferably compounds of the invention have a binding affinity for tau is at least 1.2 times that for Aβ, and more preferably at least 1.5 times, more preferably at least 2 times, more preferably at least 3 times, more preferably at least 5 times, more preferably at least 8 times, more preferably at least 10 times, more preferably at least 12 times, and even more preferably at least 15 times, for example at least 18 times, at least 20 times, at least 22 times, at least 25 times, at least 30 times, at least 40 times, at least 50 times, at least 100 times or at least 150 times. In one preferred embodiment, compounds of the invention have a binding affinity for tau that is at least 2 times that for Aβ. In one preferred embodiment, compounds of the invention have a binding affinity for tau that is at least 3 times that for Aβ. In another preferred embodiment, compounds of the invention have a binding affinity for tau that is at least 5 times that for Aβ. In another preferred embodiment, compounds of the invention have a binding affinity for tau that is at least 10 times that for Aβ. In another preferred embodiment, compounds of the invention have a binding affinity for tau that is at least 15 times that for Aβ. In another preferred embodiment, compounds of the invention have a binding affinity for tau that is at least 20 times that for Aβ. In another preferred embodiment, compounds of the invention have a binding affinity for tau that is at least 30 times that for Aβ. In an especially preferred embodiment, compounds of the invention have a binding affinity for tau that is at least 3 times that for Aβ.

In certain very preferred embodiments, compounds of the invention have a binding affinity for tau that is at least 3 times that for Aβ, and have an $IC_{50}$ value for tau deposits of less than 30 nM in a competitive binding assay (and more preferably less than 20 nM, and most preferably less than 10 nM).

It is also preferred that the compounds of the invention have a C Log P that is less than 7.0, preferably less than 6.5, preferably less than 5.0, more preferably less than 4.5, more preferably less than 4.0, more preferably less than 3.5, and more preferably less than 3.0, for example less than 2.8, less than 2.5, less than 2.3, less than 2.0, or less than 1.8.

The compounds of the present invention find utility in the diagnosis and/or the treatment or prophylaxis of conditions associated with tau deposits. For example, the compounds of the present invention find utility in the diagnosis and/or treatment or prophylaxis of tauopathies, for example: Alzheimer's disease, corticobasal degeneration (CBD), Pick's disease, progressive supranuclear palsy (PSP), Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion—body myositis, chronic traumatic encephalopathy, Down's syndrome, Gerstman-Sträussler-Scheinker syndrome, British dementia, familial Danish dementia, dementia pugilistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.Ile383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, and white matter tauopathy with globular glial inclusions. The compounds of the present invention are especially useful in the diagnosis and/or treatment (in particular the diagnosis) of Alzheimer's disease, corticobasal degeneration, Pick's disease, Parkinson's disease, chronic traumatic encephalopathy and progressive supranuclear palsy; and even more especially Alzheimer's disease and corticobasal degeneration.

The compound of the invention may be for use as a therapeutic agent (or medicament) in the treatment of a disease or disorder associated with tau deposits (i.e. tauopathies), such as the tauopathies listed above.

The invention also provides a method for the treatment or prophylaxis of a condition associated with a disease or disorder associated with tau deposits (i.e. tauopathies) in a mammal (in particular in a human), which comprises administering to the mammal a therapeutically effective amount of a compound according to the invention, or a composition comprising a compound according to the invention together with a pharmaceutically acceptable carrier. Clinical conditions mediated by tau deposits that may be treated by the method of the invention are tauopathies, for example the tauopathies listed above.

The invention also provides the use of a compound according to the invention, for the manufacture of a medicament for the treatment or prophylaxis of a condition associated with a disease or disorder associated with tau deposits (i.e. tauopathies), for example the tauopathies listed above.

The compound of the invention may also be used as a diagnostic agents (for in vivo and/or in vitro diagnostic use) for the detection of tau deposits, and preferably for the selective detection of tau deposits.

The compounds of the invention may be used for diagnostic purposes because they have the ability to target a particular pathology (tau deposits) and can be detected at the desired site. The compounds of the invention are especially useful because they selectively bind to tau deposits over Aβ deposits. This makes the compounds of the invention especially useful for diagnosis of tauopathies, such as the tauopathies listed above, and in particular Alzheimer's disease and corticobasal degeneration. For example, compounds of the invention are able to detect the presence and the level of tau deposits in a patient with or suspected of having a disease or disorder associated with tau deposits (i.e. tauopathies), such as the tauopathies listed above. The compounds of the invention are also especially useful for diagnosis of tauopathies because the compounds of the invention do not show off-target MAO binding or inhibitory activity. As MAO are present in the brain in areas that overlap with tau pathology in certain tauopathies, such off-target effects are undesirable in tau deposit ligands.

The compounds of the invention can bind tau deposits both in vivo and in vitro. The compound of the invention may be for use as a diagnostic agent (for in vivo and/or in vitro diagnostic use) in the diagnosis of disease or disorder associated with tau deposits (i.e. tauopathies), such as the tauopathies listed above.

When used as a diagnostic agent, the compounds of the invention may optionally be in labeled form, as described above. Thus the present invention also provides the use of a compound of the invention in a labeled form for use as a diagnostic agent for the diagnosis of conditions associated with a disease or disorder associated with tau deposits (i.e. a tauopathy). In such embodiments, preferably the compound of the invention in labeled form comprises one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^{3}H$, $^{11}C$, $^{14}C$, $^{13}N$, $^{15}O$, $^{18}F$, $^{19}F$, $^{120}I$, $^{123}I$ and $^{125}I$, and more preferably $^{3}H$, $^{11}C$, $^{13}N$, $^{15}O$, $^{18}F$, $^{120}I$, $^{123}I$, and $^{125}I$. When used as a diagnostic agent (especially for in vivo use), and the compound is radioactively labeled, for example with $^{11}C$, $^{13}N$, $^{15}O$, $^{18}F$ or $^{120}I$ (preferably $^{18}F$), the compounds of the invention may be detected by positron emission topography. When used as a diagnostic agent (especially for in vivo use), and the compound is radioactively labeled, for example with $^{123}I$ or $^{125}I$, the compounds of the invention may be detected by SPECT. When used as a diagnostic agent (especially for in vitro use), and the compound is radioactively labeled, for example with $^{3}H$ or $^{125}I$, the compounds of the invention may be detected by autoradiography.

As mentioned above, the compounds of the invention may be used for diagnostic purposes because they have the ability to target a particular pathology (tau deposits) and can be detected at the desired site. As such, the compounds of the invention when used as diagnostic agents are especially useful as imaging agents. Imaging agents are compounds that allow the imaging of specific organs, tissues, diseases and physiological functions. Such imaging allows for diagnosing disease, monitoring disease progression, and tracking therapeutic response.

A compound of the invention when used as a diagnostic agent, and in particular as an imaging agent, may be detected via radioscintigraphy, assays, chemilumensence, electrochemiluminescence, near infrared luminescence, fluorescence, spectroscopy, autoradiography, liquid scintillation counting, gamma imaging, magnetic resonance imaging (MRI), magnetic resonance spectroscopy (MRS), scintigraphy, single-photon emission computed tomography (SPECT), computed tomography (CT scan), and/or positron emission tomography (PET).

In embodiments of the invention wherein the compound of the invention is for use as a diagnostic agent, and in particular as an imaging agent, the type of detection instrument available is a major factor in selecting if a label is required, and what label to choose. For example, where imaging requires an isotope to be detected, the type of detection instrument used will guide if a label is needed (i.e. is the isotope naturally occurring or not, and at what abundance is it present in when it occurs naturally), and, if so, what isotope to use. In one aspect, the compound of the invention is labeled, and the form of labeling chosen must have a type of decay detectable by a given type of instrument. Moreover, other considerations such as the half-life of the radioisotopes are taken into account when selecting an isotope label for in vivo imaging.

The compounds of the invention for use as diagnostic agents for in vivo imaging (in particular imaging of tau deposits and/or quantification of tau deposits) are preferably used in conjunction with non-invasive neuroimaging techniques such as in vivo MRS, MRI, PET, SPECT and combinations thereof. A compound of the invention may be labeled with $^{11}C$, $^{13}N$, $^{15}O$, $^{18}F$ or $^{120}I$, for PET imaging; or may be radiolabeled with $^{123}I$ (or $^{125}I$) for SPECT imaging. No labeling may be required for in vivo MRS or MRI, or a compound may be labeled with $^{13}C$ for MRS or MRI.

The present invention also provides a method of diagnosing a patient or monitoring disease progression in a patient comprising administering a compound of the invention to the patient. The method may further comprise detecting the compound of the invention in vivo at the site of interest in a patient (e.g. the brain) using PET or SPECT, or detecting the compound in a sample from the patient. Preferably in such embodiments the compound of the invention comprises one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^{3}H$, $^{11}C$, $^{14}C$, $^{13}N$, $^{15}O$, $^{18}F$, $^{19}F$, $^{120}I$, $^{123}I$ and $^{125}I$, and more preferably $^{11}C$, $^{13}N$, $^{15}O$, $^{8}F$ or $^{120}I$. The present invention also provides method of diagnosing a patient or monitoring disease progression in a patient comprising contacting a compound of the invention with a sample taken from the patient.

The method may further comprise detecting the compound of the invention using radioscintigraphy, assays, chemilumensence, electrochemiluminescence, autoradiography, near infrared luminescence, fluorescence, spectroscopy, liquid scintillation counting, gamma imaging, scintigraphy, magnetic resonance imaging (MRI), magnetic resonance spectroscopy (MRS), single-photon emission computed tomography (SPECT), or computed tomography (CT scan).

In the methods of diagnosing a disease or disorder associated with tau deposits as described herein, the method may comprise:

i) administering to the subject a diagnostically effective amount of a compound of the invention;

ii) allowing the compound of the invention to distribute into the tissue of interest (such as brain or body fluids such as cerebrospinal fluid (CSF)): and iii) imaging the tissue of interest, wherein an increase in binding of the compound of the invention to the tissue of interest compared to a normal or control level of binding indicates that the subject is suffering from or is at risk of developing a disorder associated with tau deposits.

The compounds of the invention can be used for imaging tau deposits in any sample or a specific body part or body area of a patient which suspected to contain tau deposits. The compounds of the invention are particularly suitable for imaging of tau deposits in the brain, as well as in body fluids such as cerebrospinal fluid (CSF).

Diagnosis of a disease or disorder associated with tau deposits in a patient may be achieved by detecting the specific binding of a compound according to the invention to the tau deposits in a sample or in situ, which includes:

(a) bringing the sample or a specific body part or body area suspected to contain the tau deposits (e.g. the brain and/or CSF) into contact with a compound of the invention which binds the tau deposits.

(b) allowing the compound of the invention to bind to the tau deposits to form a compound/tau deposits complex, (c) detecting the formation of the compound/tau deposits complex, (d) optionally correlating the presence or absence of the compound/tau deposits complex with the presence or absence of tau deposits in the sample or specific body part or area, and (e) optionally comparing the amount of the compound/tau deposits complex to a normal or control value, wherein an increase in the amount of the compound/tau deposits complex compared to a normal control value may indicate that the patient is suffering from or is at risk of developing a tau-associated disorder.

After the sample or a specific body part or body area has been brought into contact with the compound of the invention (e.g. the brain and/or CSF), the compound is allowed to bind to the tau deposits. The amount of time required for binding will depend on the type of test (e.g. in vitro or in vivo) and can be determined by a person skilled in the art by routine experiments.

The presence or absence of the compound/tau deposits is then optionally correlated with the presence or absence of tau deposits in the sample or specific body part or area. The amount of the compound/tau deposits complex can be compared to a normal or control value which has been determined in a sample or a specific body part or body area of a healthy subject, wherein an increase in the amount of the compound/tau deposits complex compared to a normal or control value may indicate that the patient is suffering from or is at risk of developing a disease or disorder associated with tau deposits (i.e. a tauopathy).

The present invention also relates to a method of determining the amount of tau deposits in a tissue and/or a body fluid. This method comprises the steps of:

(1) providing a sample representative of the tissue and/or body fluid under Investigation (e.g. the brain and/or CSF);

(2) testing the sample for the presence of tau deposits with a compound of the present invention;

(3) determining the amount of compound bound to the tau deposits; and (4) calculating the amount of tau deposits in the tissue and/or body fluid.

The sample can be tested for the presence of tau deposits with a compound of the invention by bringing the sample into contact with a compound of the invention, allowing the compound of the invention to bind to the tau deposits to form a compound/tau deposit complex and detecting the formation of the compound/tau deposit as explained above.

Monitoring minimal residual disorder in a patient suffering from a disorder associated with tau deposits who has been treated with a therapeutic agent useful in the prevention or treatment of a disorder associated with tau deposits (for example a therapeutic agent useful in the prevention or treatment of one or more or the tauopathies listed above) may be achieved by:

carrying out steps (a) to (d) above; and (e) optionally comparing the amount of the compound/tau deposit complex to a normal or control value, wherein an increase in the amount of the complex compared to a normal or control value may indicate that the patient may still suffer from a minimal residual disease.

How steps (a) to (e) can be conducted has already been explained above.

Predicting responsiveness of a patient suffering from a disorder associated with tau deposits and being treated with a therapeutic agent useful in the prevention or treatment of a disorder associated with tau deposits can be achieved by carrying out steps (a) to (d) above; and (e) optionally comparing the amount of the compound/tau deposit complex to a normal or control value.

How steps (a) to (e) can be conducted has already been explained above.

In the method for predicting responsiveness the amount of the compound/tau deposits complex can be optionally compared at various points of time during the treatment, for instance, before and after onset of the treatment or at various points of time after the onset of the treatment. A change, especially a decrease, in the amount of the compound/tau deposits complex may indicate that the patient has a high potential of being responsive to the respective treatment.

A compound according to the present invention can also be incorporated into a test kit for detecting tau deposits. The test kit typically comprises a container holding one or more compounds according to the present Invention and instructions for using the compound for the purpose of binding to tau deposits to form a compound/tau deposit complex and detecting the formation of the compound/tau deposit complex such that presence or absence of the compound/tau deposit complex correlates with the presence or absence of the tau deposits.

Dosing

The amount of compound of the invention which is required to achieve a diagnostic or therapeutic effect will, of course, vary with the particular compound, the route of administration, the subject under treatment, including the type, species, age, weight, sex, and medical condition of the subject and the renal and hepatic function of the subject, and the particular disorder or disease being treated, diagnosed or monitored, as well as its severity. An ordinarily skilled physician, veterinarian or clinician can readily determine and prescribe the effective amount of the drug required to prevent, counter or arrest the progress of the condition or be used to diagnose a condition or the progression of a condition.

Oral dosages of the present invention, when used for as a diagnostic or therapeutic agent, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day, for adult humans. For oral administration, the compositions are preferably provided in the form of tablets or other forms of presentation provided in discrete units containing 0.01, 0.05, 0.1, 0.5, 1.0, 2.5, 5.0, 10.0, 15.0, 25.0, 50.0, 100, and 500 milligrams of the compound of the invention for the symptomatic adjustment of the dosage to the patient to be treated. A medicament typically contains from about 0.01 mg to about 500 mg of the compound of the invention, preferably from about 1 mg to about 100 mg of compound of the invention. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. For diagnostic use, preferably the compounds of the present invention may be administered in a single daily dose. Furthermore, preferred compounds for the present invention can be administered in intranasal form via topical use of suitable intranasal vehicles, or via transdermal routes, using those forms of transdermal skin patches well known to those of ordinary skill in the art.

While it is possible for the compound of the invention to be administered alone, it is preferable for it to be present in a pharmaceutical formulation or composition. Accordingly, the invention provides a pharmaceutical formulation or composition comprising a compound according to the invention, and a pharmaceutically acceptable diluent, excipient or carrier. Pharmaceutical compositions of the invention may take the form of a pharmaceutical formulation as described below.

Formulations

"Pharmaceutical" as used here does not necessarily mean therapeutic, for example, a pharmaceutical formulation may be used as a diagnostic agent, such as an imaging agent. The pharmaceutical formulations according to the invention include those suitable for oral, parenteral (including subcutaneous, intradermal, intramuscular, intravenous [bolus or infusion], and intraarticular), inhalation (including fine particle dusts or mists which may be generated by means of various types of metered dose pressurized aerosols), nebulizers or insufflators, rectal, intraperitoneal and topical (including dermal, buccal, sublingual, and intraocular) administration, although the most suitable route may depend upon, for example, the condition and disorder of the recipient to be treated or diagnosed.

The formulations may conveniently be presented in unit dosage form and may be prepared by any of the methods well known in the art of pharmacy. All methods include the step of bringing the compound of the invention into association with the carrier which constitutes one or more accessory ingredients. In general the formulations are prepared by uniformly and intimately bringing into association the compound of the invention with liquid carriers or finely divided solid carriers or both and then, if necessary, shaping the product into the desired formulation.

Formulations of the present invention suitable for oral administration may be presented as discrete units such as capsules, cachets, pills or tablets each containing a predetermined amount of the compound of the invention; as a powder or granules; as a solution or a suspension in an aqueous liquid or a non-aqueous liquid, for example as elixirs, tinctures, suspensions or syrups; or as an oil-in-water liquid emulsion or a water-in-oil liquid emulsion. The compound of the invention may also be presented as a bolus, electuary or paste.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Formulations for topical administration in the mouth, for example buccally or sublingually, include lozenges comprising the compound of the invention in a flavoured basis such as sucrose and acacia or tragacanth, and pastilles comprising the compound of the invention in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the compound of the invention.

It should be understood that in addition to the ingredients particularly mentioned above, the formulations of this invention may include other agents conventional in the art having regard to the type of formulation in question, for example those suitable for oral administration may include flavouring agents.

Whilst a compound of the invention may be used as the sole active ingredient (i.e. sole therapeutic agent or sole diagnostic agent) in a medicament, it is also possible for the compound to be used in combination with one or more further active ingredient. For example, a compound of the invention may be used as the sole diagnostic agent in a diagnostic composition, or it is also possible for the compound to be used in combination with one or more further diagnostic agents and/or one or more therapeutic agents. Alternatively, a compound of the invention may be used as the sole diagnostic agents and/or therapeutic agent in a medicament, or it is also possible for the compound to be used in combination with one or more further therapeutic agents and/or one or more diagnostic agents.

Thus, the invention also provides a compound according to the invention together with a further diagnostic agent, for simultaneous, sequential or separate administration. Such further diagnostic agents may be further compounds according to the invention, or they may be different diagnostic agents. The further diagnostic agent may be an agent useful in the diagnosis of tauopathies (for example the tauopathies listed above).

In certain preferred embodiments, the further diagnostic agent may be an agent that is selective for Aβ deposits useful in diagnosis of Alzheimer's disease. The further diagnostic agent may be detectable by radioscintigraphy, magnetic resonance imaging (MRI), assays, chemilumensence, near infrared luminescence, fluorescence, autoradiography, liquid scintillation counting, gamma imaging, scintigraphy, magnetic resonance imaging, magnetic resonance spectroscopy, SPECT, computed tomography (CT scan) and/or positron emission tomography (PET). Preferably, the further diagnostic agent is detectable by positron emission tomography. For example, the further agent may be a PET ligand.

For example, the compounds of the invention may be effectively administered in combination with (or may be used in vitro for in vitro diagnosis with) effective amounts of one or more other diagnostic agents such as luminescent conjugated oligothiophenes (e.g. q-FTAA-CN, p-FTAA-CN, h-FTAA-CN), Pittsburgh compound B (PiB), fludeoxyglucose F 18 (FDG), florbetapir, flutemetamol, NAV4694, PBB3, AT-100, 4G8, Congo red, Thioflavin S, Thioflavin T, m-l-stilbene, chrysamine G, BF-277, TZDM, FDDNP, MeO-X-04, IMPY, NIAD-4 $^3$H-X-34, luminescent conjugated polythiophenes (e.g. polythiophene acetic acid (PTAA), tPTAA, POWT, tPOWT, POMT, tPOMY) and GTP1 (Genentech Tau Probe 1).

The invention further provides a compound according to the invention together with a further therapeutic agent, for simultaneous, sequential or separate administration. Such further therapeutic agents may be further compounds according to the invention, or they may be different therapeutic agents, for example an agent useful in the prevention or treatment of one or more or the tauopathies listed above. For example, the compounds of the invention may be effectively administered in combination with effective amounts of other agents such as antibodies (for example active immunisation (e.g. ACI-35 (AC Immune/Janssen), and AADvac1 (Axon Neuroscience)), passive immunization (e.g. tau antibodies, such as BMS-986168 (IPN007, Bristol-Myers Squibb Company), C2N-8E12 (C2N/AbbVie), and RG6100 (R07105705, AC Immune/Genentech; aducanumab; solanezumab; gantenerumab; and crenezumab), RG7345 (R06926496, MAb86, F. Hoffmann-La Roche), PHF1, 4E6G7, 6B2G12), MK-8719 (Merck & Co.), TPI-287 (Cortice Biosciences), methylene blue (for example TRx 0327 and Rember), dopaminergic treatments (for example levodopa, caridopa, dopamine agonists (e.g. bromocriptine, perfolide, pramipexole, ropinirole)), cholinesterase inhibitors (e.g. tacrine, donepezil, rivastigmine, galantamine), monoamine oxidase inhibitors (e.g. selegiline), antocholinerginc agents (e.g. trihexyphenidyl, benztropine mesylate, biperiden, procyclidine), antihistamine (e.g. diphenhydramine), antipsychotic drugs, analgesic drugs, anti-inflammatories, riluzole, non-steroidal anti-inflammatory drugs, caffein A2A receptor antagonists, CERE-120 (adeno-associated virus serotype 2-neurturin), amantadine, tolcapone, entacapone, ethosuximide, trazodone, and dibenzoylmethane.

The above other diagnostic and therapeutic agents, when employed in combination with the compounds of the present invention, may be used, for example, in those amounts indicated in the Physicians' Desk Reference (PDR) or as otherwise determined by one of ordinary skill in the art.

The compounds of the invention as described above, optionally in labeled form, also find use as a reference compound in methods of identifying ligands for the tau deposits. Thus, the invention provides a method of identifying a ligand for tau deposits which comprises use of a compound of the invention or a compound of the invention in labeled form, as a reference compound. For example, such a method may involve a competitive binding experiment in which binding of a compound of the invention to the tau deposits is reduced by the presence of a further compound which has tau deposits-binding characteristics, for example stronger tau deposits-binding characteristics than the compound of the invention in question.

EXPERIMENTAL

Synthesis of Compounds of the Invention

General Information

All reagents and solvents used were analytical grade and commercially available. Anhydrous reactions were routinely used for reactions. Reactions were typically run under inert atmosphere of nitrogen ($N_2$).

[1]H Spectra were recorded on a Bruker 500 NMR spectrometer. Mass spectra were recorded on a Waters Acquity system (LC) and a single quadruple 3100 mass spectrometer. The mass spectrometer was equipped with an electrospray ion source (ES) operating in a positive or negative mode. The capillary voltage was 3.5 kV and the cone voltage was 30 V. The mass spectrometer was scanned between m/z 100-850 with a scan time of 0.5 s. The column temperature was set to 50° C. with a linear gradient starting at 95% A (A: 10 mM $NH_4HCO_3$) and ending in 100% B (B: MeCN). The column used was an Acquity UPLC™ BEH $C_{18}$ 1.7 μm, 2.1×50 mm run at 0.4 ml/min.

The HPLC used was an Agilent 1100 coupled to an Agilent 1290 Infinity DAD. The column used was an XBridge $C_{18}$ 3.5 μm, 3.0×50 mm run at 0.8 ml/min. The column temperature was set to 50° C. with a linear gradient starting at 98-2% A over 3.5 min (A: 10 mM $NH_4HCO_3$) then holding 98% B (B: MeCN) for 1.5 min.

The semi-prep was a Gilson with a 322 pump. The column used was a Kromasil $C_8$ 7 μm, 20×250 mm.

Microwave heating was performed in a Biotage Initiator 2.0.

Chromatography separations were performed using Silica gel 60 (0.040-0.063 mm) in a filter funnel or by using a Teledyne ISCO CombiFlash Rf with varying sizes (4-120 g) of RediSep Rf Silica columns. TLC plates were Merck Silica gel 60 $F_{254}$.

The term room temperature (rt) means, unless otherwise specified, a temperature between 16 and 25° C. The term reflux means, unless otherwise stated, in reference to an employed solvent using a temperature at or slightly above the boiling point of the named solvent.

General Procedures

General procedure 1 (GP1)

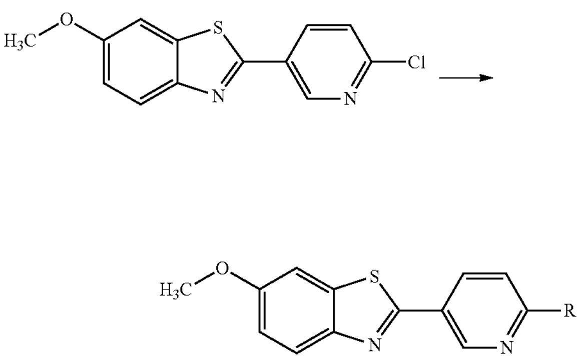

2-(6-Chloropyridin-3-yl)-6-methoxy-1,3-benzothiazole (100 μmol) and an optionally substituted azetidine, pyrrolidine or piperidine (1-10 eq) wherein the N of the azetidine, pyrrolidine or piperidine is unsubstituted (i.e. it is an N—H group, or $NH_2^+$ group if the azetidine, pyrrolidine or piperidine is in the form of a salt), are dissolved or slurried in methanol (1.5 ml) and subjected to the microwave at 150° C. for 90 min. If the azetidine, pyrrolidine or piperidine is in the form of a salt (for example a hydrochloride salt) then an excess of Hunig's base is added. Generally, the product precipitates upon cooling and is filtered and washed with cold methanol. If a further purification step is required this is described in the experimental section for that compound.

General procedure 2 (GP2)

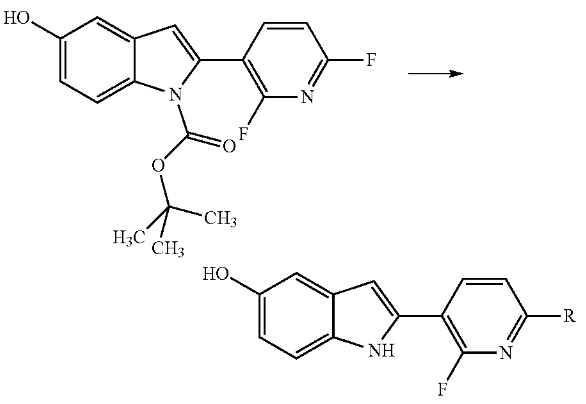

tert-Butyl 2-(2,6-difluoropyridin-3-yl)-5-hydroxy-1H-indole-1-carboxylate (intermediate 5, 100 μmol), an optionally substituted azetidine, pyrrolidine or piperidine (1 eq) wherein the N of the azetidine, pyrrolidine or piperidine is unsubstituted (i.e. it is an N—H group, or $NH_2^+$ group if the azetidine, pyrrolidine or piperidine is in the form of a salt), and an excess of Hunig's base are dissolved or slurried in methanol (1.5 ml) and subjected to the microwave at 150° C. for 60 min. Generally the product precipitates upon cooling and is filtered and washed with cold methanol. If a further purification step is required this is described in the experimental section for that compound.

General procedure 3-1 (GP3-1)

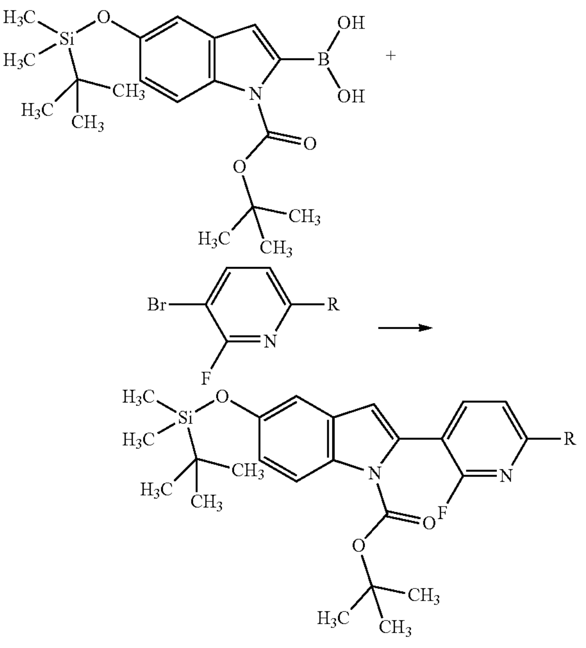

{1-[(tert-Butoxy)carbonyl]-5-[(tert-butyldimethylsilyl)oxy]-1H-indol-2-yl}boronic acid (410 mg, 1.1 eq) and a bromo amine having the structure shown above and wherein R is an optionally substituted azetidine, pyrrolidine or piperidine (for example intermediate 1-4, 1 mmol) were dissolved in dioxane (6 ml/mmol) in a 20 ml microwave vial. The solution was bubbled with $N_2$ for 3 min, then Pd(dppf)

$Cl_2$ DCM 1:1 complex (41 mg, 5 mol %) was added followed by 2 M $K_2CO_3$ (1.5 ml, 3 eq). The solution was again bubbled with $N_2$ for 5 min then capped. The reaction was run in a preheated oil bath at 90° C. for 45 h.

The aqueous layer was removed from the cooled reaction mixture, and the mixture was diluted with ethyl acetate, dried ($MgSO_4$), then filtered to give the crude product. The crude product was purified by using the ISCO as described in the experimental section below.

General procedure 3-2 (GP3-2)

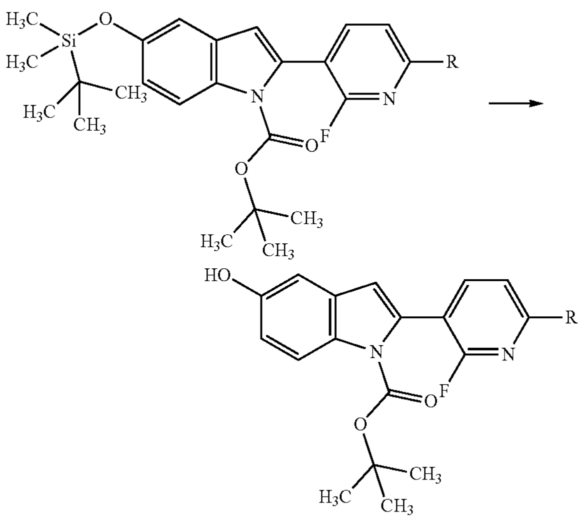

The silyl protecting group was removed by dissolving the starting material in THF (15 ml/mmol), cooling with an ice-bath and adding a 1 M TBAF in THF (1.1 eq) solution. The reaction was monitored using an HPLC and was generally complete after 20 min at 0° C. After a standard work-up (ethyl acetate, washing with water, brine, drying) the crude was purified using the ISCO as described in the experimental section below.

General procedure 3-3 (GP3-3)

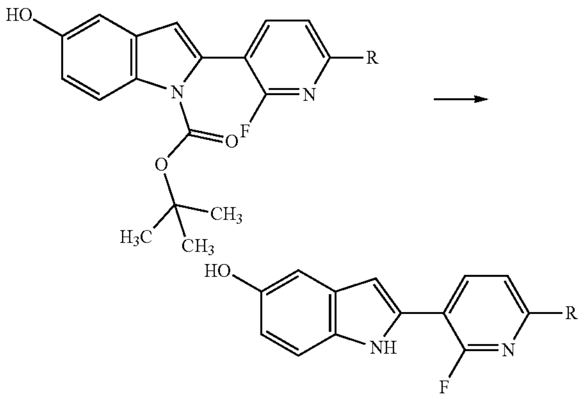

The BOC group was removed by dissolving the starting material in DCM (15 ml/mmol), cooling on an ice-bath and adding an equal volume of TFA. The reaction was monitored using HPLC and we generally complete after 1-4 h at rt.

The solvent was removed by $N_2$ and the remains were suspended or dissolved in methanol (15 ml/mmol). Lithium hydroxide hydrate (10 eq) was added followed by water (3 mol/mmol). The reaction was stirred for 30 min then was quenched with a saturated ammonium chloride solution. The product was isolated by filtration or by using the centrifuge. In cases where the product was impure, purification was done using the semi-prep or the ISCO as described in the experimental section below.

SYNTHESIS OF INTERMEDIATE COMPOUNDS

Intermediate 1: 1-(5-Bromo-6-fluoropyridin-2-yl)azetidin-3-yl]methanol

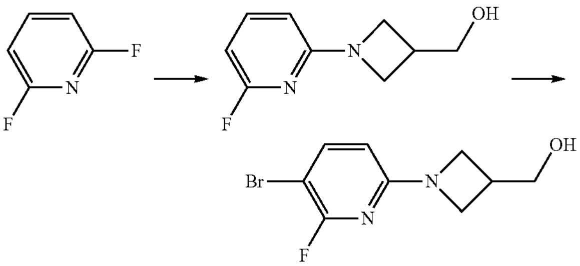

Azetidin-3-ylmethanol HCl (1.0 g, 8.1 mmol) was slurried in dioxane (10 ml), and 2,6-difluoropyridine (0.75 ml, 1 eq) was added followed by Hunig's base (3.5 ml, 2.5 eq). The reaction was heated to 100° C. overnight.

The reaction mixture was diluted with ethyl acetate, washed with water, treated with brine, dried with $MgSO_4$, filtered and the solvent was removed in vacuo to give the crude product.

The crude product was purified on the ISCO (25 g silica, applied with DCM, eluted with 30-60% ethyl acetate/hexane over 5 min) to give 1-(6-fluoropyridin-2-yl)azetidin-3-yl]methanol (0.75 g oil, 51% yield, HPLC Rf 1.83 min, MS m/z (M+1) 183.1, TLC 50% ethyl acetate/hexane Rf 0.17).

1-(6-Fluoropyridin-2-yl)azetidin-3-yl]methanol (0.75 g, 4.1 mmol) was dissolved in acetonitrile (20 ml), cooled with an ice-bath and N-Bromosuccinimide (NBS, 0.73 g, 1 eq) was added in 2 portions. The reaction was allowed to stir at rt for 30 min.

The reaction mixture was diluted with ethyl acetate, washed with water, treated with brine, dried with $MgSO_4$, filtered and the solvent was removed in vacuo to give the crude product.

The crude product was purified on the ISCO (25 g silica, applied with DCM, eluted with 30-60% ethyl acetate/hexane over 5 min) to give [1-(5-bromo-6-fluoropyridin-2-yl)azetidin-3-yl]methanol (0.92 g oil, 86% yield, HPLC Rf 2.62 min, MS m/z (M+1) 261.1, 263.0, (M−1) 259.1, 261.1, TLC: 50% ethyl acetate/hexane Rf 0.18).

Intermediate 2: 2-[1-(5-Bromo-6-fluoropyridin-2-yl)azetidin-3-yl]ethan-1-ol

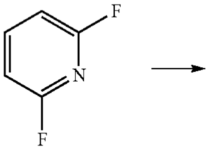

-continued

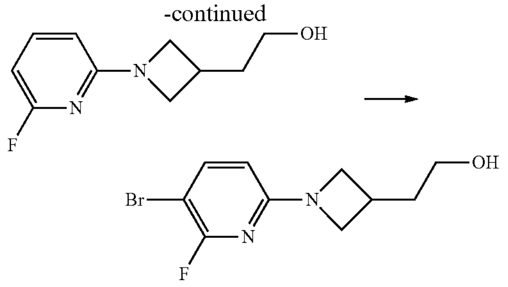

2-(Azetidin-3-yl)ethanol HCl (1.0 g, 7.26 mmol) was slurried in dioxane (10 ml), and 2,6-difluoropyridine (1.0 ml, 1.5 eq) was added followed by pyridine (3 ml, 5 eq). The reaction was heated to 100° C. overnight.

The reaction mixture was diluted with ethyl acetate, washed with water, treated with brine, dried with $MgSO_4$, and filtered, and then the solvent was removed in vacuo to give the crude product.

The crude product was purified on the ISCO (25 g silica, applied with DCM, eluted with 30-60% ethyl acetate/hexane over 6 min) to give 2-[1-(6-fluoropyridin-2-yl)azetidin-3-yl]ethan-1-ol (0.17 g oil, 12% yield, HPLC Rf 2.22 min, MS m/z (M+1) 197.2, TLC 50% ethyl acetate/hexane Rf 0.18).

2-[1-(6-Fluoropyridin-2-yl)azetidin-3-yl]ethan-1-ol (0.17 g, 0.88 mmol) was dissolved in acetonitrile (5 ml), cooled with an ice-bath and NBS (150 mg, 0.95 eq) was added in 2 portions. The reaction was allowed to stir at rt for 30 min.

The reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 30-50% ethyl acetate/hexane over 4 min) to give [1-(5-bromo-6-fluoropyridin-2-yl)azetidin-3-yl]methanol (210 mg oil, 86% yield, HPLC Rf 2.78 min, MS m/z (M+1) 275.0, 277.1, (M−1) 273.1, 275.1, TLC: 50% ethyl acetate/hexane Rf 0.18).

Intermediate 3: (3R)-1-(5-Bromo-6-fluoropyridin-2-yl)piperidin-3-ol

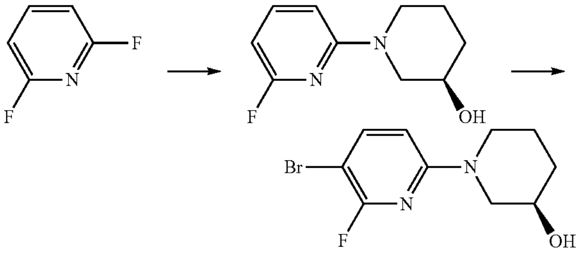

(R)-3-Hydroxypiperidine HCl (1.12 g, 8.1 mmol) was slurried in dioxane (10 ml), and 2,6-difluoropyridine (0.75 ml, 1 eq) was added followed by Hunig's base (3.5 ml, 2.5 eq). The reaction was heated to 100° C. overnight.

The reaction mixture was diluted with ethyl acetate, washed with water, treated with brine, dried with $MgSO_4$, filtered and the solvent was removed in vacuo to give the crude intermediate product.

The crude intermediate product was purified on the ISCO (40 g silica, applied with DCM, eluted with 20-50% ethyl acetate/hexane over 6 min) to give (3R)-1-(6-fluoropyridin-2-yl)piperidin-3-ol (1.11 g oil, 76% yield, HPLC Rf 2.37 min, MS m/z (M+1) 197.2, TLC 50% ethyl acetate/hexane Rf 0.32).

(3R)-1-(6-Fluoropyridin-2-yl)piperidin-3-ol (1.11 g, 5.7 mmol) was dissolved in acetonitrile (25 ml), cooled with an ice-bath and NBS (1.0 g, 1 eq) was added in 2 portions. The reaction was allowed to stir at rt for 30 min.

The reaction mixture was diluted with ethyl acetate, washed with water, treated with brine, dried with $MgSO_4$, and filtered, and then the solvent was removed in vacuo to give the crude product.

The crude product was purified on the ISCO (40 g silica, applied with DCM, eluted with 20-40% ethyl acetate/hexane over 5 min) to give (3R)-1-(5-bromo-6-fluoropyridin-2-yl)piperidin-3-ol (1.3 g oil, 84% yield, HPLC Rf 2.92 min, MS m/z (M+1) 275.1, 277.1, (M−1) 273.1, 275.1, TLC: 50% ethyl acetate/hexane Rf 0.32).

Intermediate 4: (3S)-1-(5-Bromo-6-fluoropyridin-2-yl)piperidin-3-ol

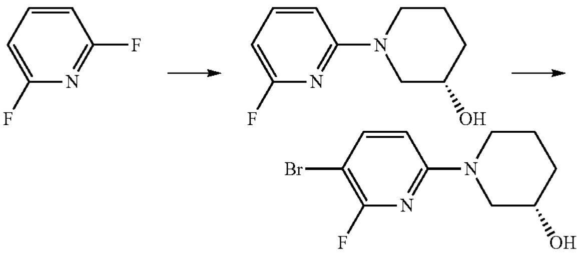

(S)-3-Hydroxypiperidine HCl (1.12 g, 8.1 mmol) was slurried in dioxane (10 ml), and 2,6-difluoropyridine (0.75 ml, 1 eq) was added followed by Hunig's base (3.5 ml, 2.5 eq). The reaction was heated to 100° C. overnight.

The reaction mixture was diluted with ethyl acetate, washed with water, treated with brine, dried with $MgSO_4$, and filtered, and then the solvent was removed in vacuo to give the crude intermediate product.

The crude intermediate product was purified on the ISCO (40 g silica, applied with DCM, eluted with 20-50% ethyl acetate/hexane over 6 min) to give (3R)-1-(6-fluoropyridin-2-yl)piperidin-3-ol (1.11 g oil, 76% yield, HPLC Rf 2.40 min, MS m/z (M+1) 197.2, TLC 50% ethyl acetate/hexane Rf 0.32).

(3S)-1-(6-Fluoropyridin-2-yl)piperidin-3-ol (1.11 g, 5.7 mmol) was dissolved in acetonitrile (25 ml), cooled with an ice-bath and NBS (1.0 g, 1 eq) was added in 2 portions. The reaction was allowed to stir at rt for 30 min.

The reaction mixture was diluted with ethyl acetate, washed with water, treated with brine, dried with $MgSO_4$, and filtered, and then the solvent was removed in vacuo to give the crude product.

The crude product was purified on the ISCO (40 g silica, applied with DCM, eluted with 20-40% ethyl acetate/hexane over 5 min) to give (3S)-1-(5-bromo-6-fluoropyridin-2-yl)piperidin-3-ol (1.41 g oil, 91% yield, HPLC Rf 2.92 min, MS m/z (M+1) 275.1, 277.1, (M−1) 273.1, 275.1, TLC: 50% ethyl acetate/hexane Rf 0.32).

Intermediate 5: 2-(6-Chloropyridin-3-yl)-6-methoxy-1,3-benzothiazole

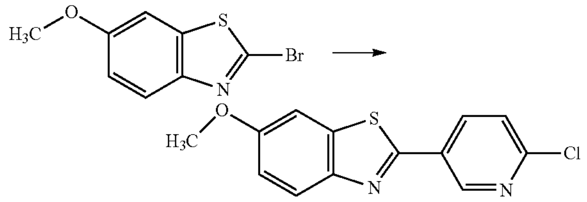

2-Bromo-6-methoxy-1,3-benzothiazole (0.73 g, 3.0 mmol) and (6-chloro-3-pyridyl)boronic acid (0.61 g, 1.3 eq) were weighed into a 20 ml microwave vial and dissolved in DMF (8 ml). $N_2$ was bubbled through the mixture. Tetrakis (0.21 g, 6 mol %) was then added followed by 2 M potassium carbonate (3 ml, 2 eq). $N_2$ was again bubbled through the mixture for 1 min and the vial was capped. The reaction mixture was subjected to the microwave at 75° C. for 4 h.

The reaction mixture was diluted with ethyl acetate, treated with brine, dried over anhydrous $MgSO_4$ and the solvent was removed in vacuo.

The crude product was purified on the ISCO (40 g silica column, applied with DCM, eluted with 10-40% ethyl acetate/hexane over 14 min) to give 2-(6-chloropyridin-3-yl)-6-methoxy-1,3-benzothiazole (240 mg solid, 37% yield). 1H-NMR (DMSO-d6) δ 9.04 (dd, 1H), 8.43 (dd, 1H), 7.99 (d, 1H), 7.77 (d, 1H), 7.70 (dd, 1H), 7.17 (dd, 1H), 3.86 (s, 3H).

Intermediate 6: [1-(5-Bromo-6-fluoropyridin-2-yl) piperidin-4-yl]methanol

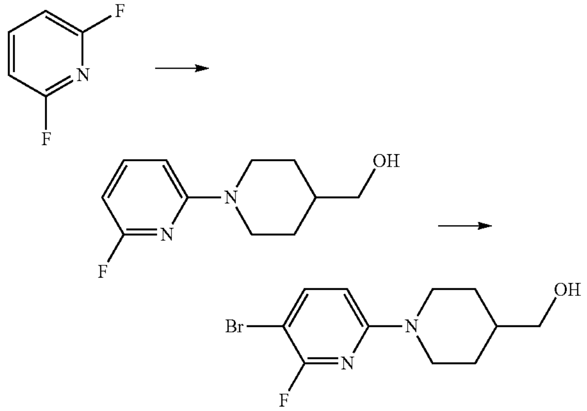

Difluoropyridine (1.6 ml, 17.4 mmol) was dissolved in dioxane (15 ml) and 4-piperidinemethanol (2.0 g, 1 eq) was added followed by Hunig's base (4.5 ml, 1.5 eq). The reaction was heated to reflux for 1 h.

The reaction mixture was diluted with ethyl acetate, washed with water, treated with brine, dried with $MgSO_4$, filtered and the solvent was removed in vacuo to give the crude product.

The crude product was purified on the ISCO (40 g silica, applied with DCM, eluted with 25-40% ethyl acetate/hexane over 5 min) to give 1.94 g oil (53% yield, MS m/z (M+1) 211).

The oil (1.94 g, 9.2 mmol) was dissolved in acetonitrile (50 ml), cooled with an ice-bath and NBS (1.8 g, 1.1 eq) was added. The reaction was allowed to stir at rt for 1 h. The reaction mixture was poured onto ice and was allowed to stir overnight.

The reaction mixture was diluted with ethyl acetate, washed with water, treated with brine, dried with $MgSO_4$, filtered and the solvent was removed in vacuo to give the crude product.

The crude product was purified on the ISCO (40 g silica, applied with DCM, eluted with 25-50% ethyl acetate/hexane over 10 min) to give [1-(5-bromo-6-fluoropyridin-2-yl)piperidin-4-yl]methanol (1.78 g solid, 67% yield, MS m/z (M+1) 289, 291). TLC: 50% ethyl acetate Rf 0.18.

Intermediate 7: tert-Butyl 5-[(tert-butyldimethylsilyl)oxy]-2-(2,6-difluoropyridin-3-yl)-1H-indole-1-carboxylate

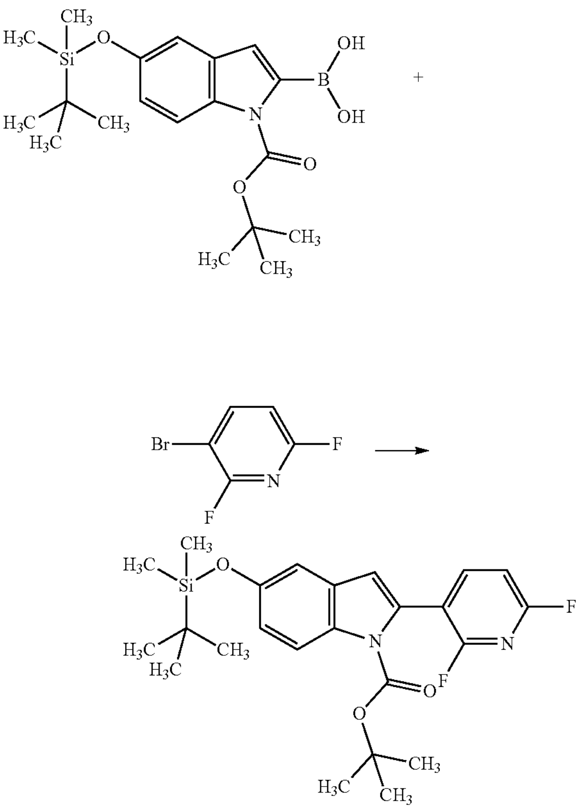

Using the general method 'GP3-1', {1-[(tert-butoxy)carbonyl]-5-[(tert-butyldimethylsilyl)oxy]-1H-indol-2-yl}boronic acid and 3-bromo-2,6-difluoropyridine were reacted on a 2 mmol scale.

The crude intermediate was purified on the ISCO (40 g silica, applied with hexane/DCM (1:1), eluted with 0-15% ethyl acetate/hexane over 6 min) to give tert-butyl 5-[(tert-butyldimethyl silyl)oxy]-2-(2,6-difluoropyridin-3-yl)-1H-indole-1-carboxylate (860 mg foam, 93% yield, HPLC Rf 4.65 min, MS m/z (M+1) 461.3, TLC 5% ethyl acetate/hexane Rf 0.19).

Intermediate 8: tert-Butyl 2-(2,6-difluoropyridin-3-yl)-5-hydroxy-1H-indole-1-carboxylate

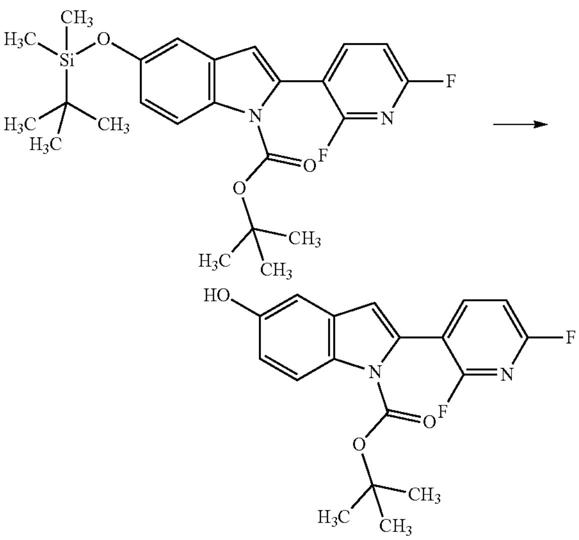

Using the general method 'GP3-2', tert-butyl 5-[(tert-butyldimethylsilyl)oxy]-2-(2,6-difluoropyridin-3-yl)-1H-indole-1-carboxylate (860 mg, 1.9 mmol) was reacted to remove the silyl protecting group.

The crude intermediate was purified on the ISCO (25 g silica, applied with DCM, eluted with 10-25% ethyl acetate/hexane over 7 min) to give tert-butyl 2-(2,6-difluoropyridin-3-yl)-5-hydroxy-1H-indole-1-carboxylate (570 mg oil, 89% yield, HPLC Rf 3.40 min, MS m/z (M−1) 345.2, TLC 25% ethyl acetate/hexane Rf 0.18).

Intermediate 9: 1-(5-Bromo-6-fluoropyridin-2-yl)-4-(hydroxymethyl)piperidin-4-ol

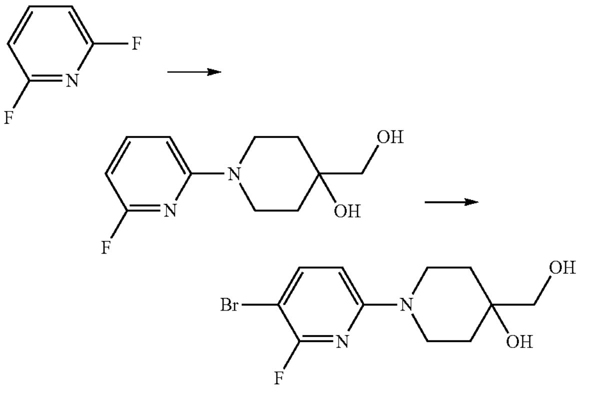

Difluoropyridine (0.78 ml, 1.5 eq) and 4-(hydroxymethyl)piperidin-4-ol HCl (0.96 g, 5.7 mmol) were slurried in dioxane (10 ml) followed by Hunig's base (2.5 ml, 2.5 eq). The reaction was heated at 100° C. overnight.

The reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 80-95% ethyl acetate/hexane over 3.5 min) to give 1-(6-fluoropyridin-2-yl)-4-(hydroxymethyl)piperidin-4-ol (93 mg oil, 7% yield, HPLC Rf 1.95 min, MS m/z (M+1) 227.1, (M−1) 225.1, TLC ethyl acetate Rf 0.25).

1-(6-Fluoropyridin-2-yl)-4-(hydroxymethyl)piperidin-4-ol (93 mg, 0.41 mmol) was dissolved in acetonitrile (5 ml), cooled with an ice-bath and NBS (73 g, 1 eq) was added. The reaction was allowed to stir at rt for 20 min.

The reaction mixture was diluted with ethyl acetate, washed with water, treated with brine, dried with $MgSO_4$, filtered and the solvent was removed in vacuo to give the crude product.

The crude product was purified on the ISCO (12 g silica, applied with DCM, eluted with 80% ethyl acetate/hexane) to give 1-(5-bromo-6-fluoropyridin-2-yl)-4-(hydroxymethyl)piperidin-4-ol (100 mg oil, 81% yield, HPLC Rf 2.63 min, MS m/z (M+1) 305.0, 307.1, (M−1), 303.1, 305.0, TLC: ethyl acetate Rf 0.23).

Intermediate 10: (3R)-1-(5-Bromopyridin-2-yl)piperidin-3-ol

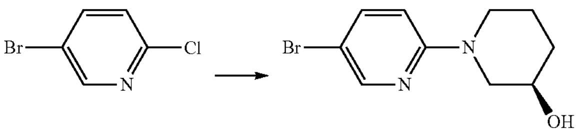 [SMILES: Clc1ccc(Br)cn1 ; O[C@@H]1CCCN(c2ccc(Br)cn2)C1]

In a 20 ml microwave vial, 5-bromo-2-chloropyridine (0.77 g, 4.0 mmol) and (R)-3-hydroxypiperidine HCl (1.65 g, 3 eq) were dissolved in methanol (10 ml) followed by Hunig's base (2.5 ml, 4.5 eq). The reaction was subjected to the microwave at 150° C. for 3 h.

The reaction mixture was diluted with ethyl acetate, washed with water, treated with brine, dried with $MgSO_4$, filtered and the solvent was removed in vacuo to give the crude product.

The crude product was purified on the ISCO (25 g silica, applied with DCM, eluted with 25-45% ethyl acetate/hexane over 6 min) to give (3R)-1-(5-bromopyridin-2-yl)piperidin-3-ol (0.35 g oil, 35% yield, HPLC Rf 2.68 min, MS m/z (M+1) 257.0, 259.0, TLC 50% ethyl acetate/hexane Rf 0.23).

Intermediate 11: tert-Butyl 5-hydroxy-2-{6-[(3R)-3-hydroxypiperidin-1-yl]pyridin-3-yl}-1H-indole-1-carboxylate

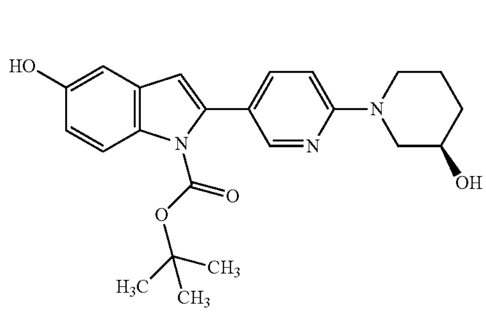 [SMILES: CC(C)(C)OC(=O)n1c(-c2ccc(N3CCC[C@@H](O)C3)nc2)cc2cc(O)ccc21]

Step (i):

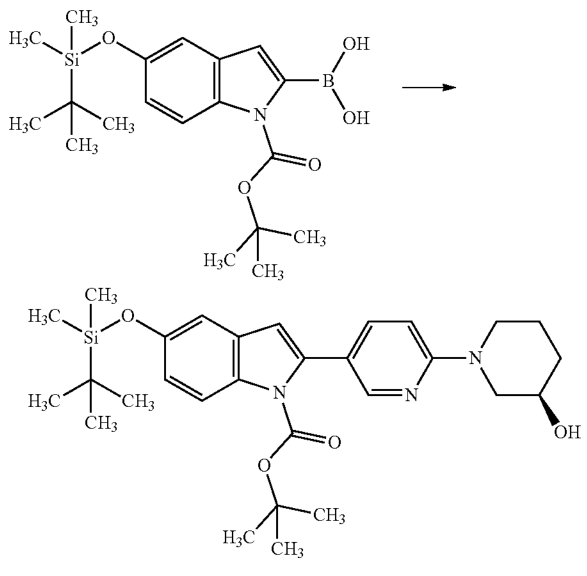

Using the general method 'GP3-1', {1-[(tert-butoxy)carbonyl]-5-[(tert-butyldimethylsilyl)oxy]-1H-indol-2-yl}boronic acid and (3R)-1-(5-bromopyridin-2-yl)piperidin-3-ol (Intermediate 10) were reacted on a 1.4 mmol scale.

The crude intermediate was purified on the ISCO (25 g silica, applied with DCM, eluted with 10-40% ethyl acetate/hexane over 7 min) to give tert-butyl 5-[(tert-butyldimethylsilyl)oxy]-2-{6-[(3R)-3-hydroxypiperidin-1-yl]pyridin-3-yl}-1H-indole-1-carboxylate (590 mg foam, 82% yield, HPLC Rf 4.57 min, MS m/z (M+1) 524.4, TLC 50% ethyl acetate/hexane Rf 0.39).

Step (ii):

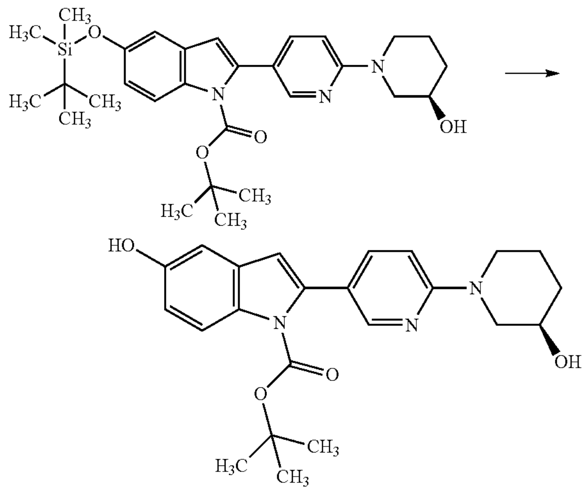

Using the general method 'GP3-2', tert-butyl 5-[(tert-butyldimethylsilyl)oxy]-2-{6-[(3R)-3-hydroxypiperidin-1-yl]pyridin-3-yl}-1H-indole-1-carboxylate (580 mg, 1.1 mmol) was reacted to remove the silyl protecting group.

The crude intermediate was purified on the ISCO (12 g silica, applied with DCM, eluted with 30-60% ethyl acetate/hexane over 4 min) to give tert-butyl 5-hydroxy-2-{6-[(3R)-3-hydroxypiperidin-1-yl]pyridin-3-yl}-1H-indole-1-carboxylate (0.44 g foam, 99% yield, HPLC Rf 3.04 min, MS m/z (M+1) 410.3, (M−1) 408.3, TLC 50% ethyl acetate/hexane Rf 0.14).

Intermediate 12: (3R)-1-(5-Bromopyrimidin-2-yl)piperidin-3-ol

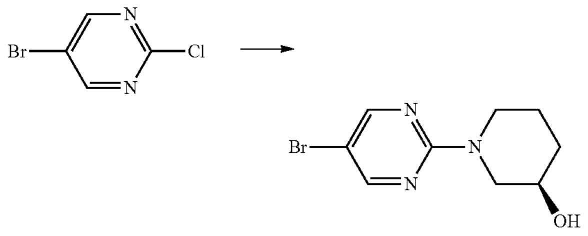

In a 20 ml microwave vial, 5-bromo-2-chloropyridine (0.77 g, 4.0 mmol) and (R)-3-hydroxypiperidine HCl (1.65 g, 3 eq) were dissolved in methanol (10 ml) followed by Hunig's base (2.5 ml, 4.5 eq). The reaction was subjected to the microwave at 80° C. for 1 h.

The reaction mixture was diluted with ethyl acetate, washed with water, treated with brine, dried with $MgSO_4$, filtered and the solvent was removed in vacuo to give the crude product.

The crude product was purified on the ISCO (25 g silica, applied with DCM, eluted with 20-40% ethyl acetate/hexane over 4 min) to give (3R)-1-(5-bromopyrimidin-2-yl)piperidin-3-ol (0.95 g solid, 92% yield, HPLC Rf 2.60 min, MS m/z (M+1) 258.0, 260.0, TLC 50% ethyl acetate/hexane Rf 0.30).

Intermediate 13: tert-Butyl 5-hydroxy-2-{2-[(3R)-3-hydroxypiperidin-1-yl]pyrimidin-5-yl}-1H-indole-1-carboxylate

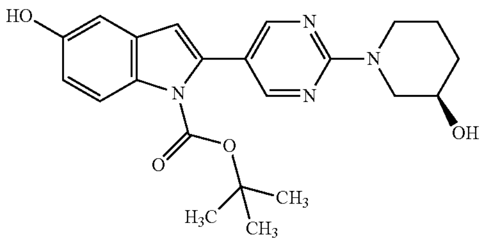 [SMILES: CC(C)(C)OC(=O)n1c(-c2cnc(N3CCC[C@@H](O)C3)nc2)cc2cc(O)ccc21]

Step (i):

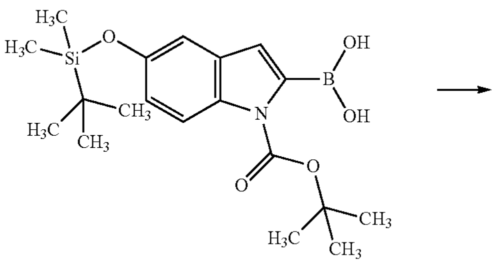

-continued

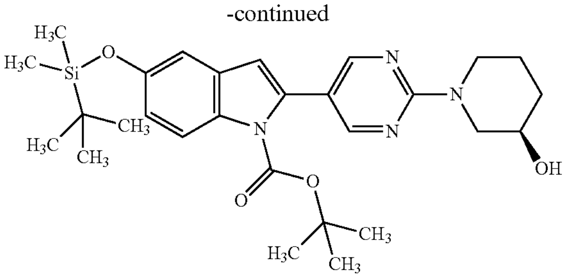

Using the general method 'GP3-1', {1-[(tert-butoxy)carbonyl]-5-[(tert-butyldimethylsilyl)oxy]-1H-indol-2-yl}boronic acid and (3R)-1-(5-bromopyrimidin-2-yl)piperidin-3-ol (Intermediate 12) were reacted on a 1.0 mmol scale.

The crude intermediate was purified on the ISCO (25 g silica, applied with DCM, eluted with 20-40% ethyl acetate/hexane over 4.5 min) to give tert-butyl 5-[(tert-butyldimethylsilyl)oxy]-2-{2-[(3R)-3-hydroxypiperidin-1-yl]pyrimidin-5-yl}-1H-indole-1-carboxylate (0.45 g foam, 86% yield, HPLC Rf 4.57 min, MS m/z (M+1) 525.3, TLC 50% ethyl acetate/hexane Rf 0.31).

Step (ii):

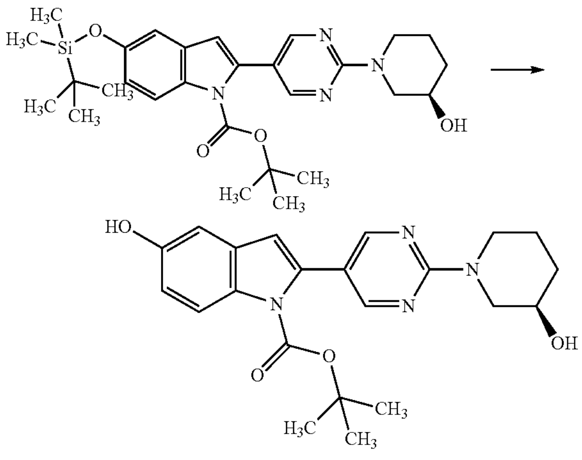

Using the general method 'GP3-2', tert-butyl 5-[(tert-butyldimethylsilyl)oxy]-2-{2-[(3R)-3-hydroxypiperidin-1-yl]pyrimidin-5-yl}-1H-indole-1-carboxylate (0.44 g, 0.85 mmol) was reacted to remove the silyl protecting group.

The crude intermediate was purified on the ISCO (12 g silica, applied with DCM, eluted with 30-60% ethyl acetate/hexane over 4 min) to give tert-butyl 5-hydroxy-2-{2-[(3R)-3-hydroxypiperidin-1-yl]pyrimidin-5-yl}-1H-indole-1-carboxylate (0.33 g foam, 95% yield, HPLC Rf 3.02 min, MS m/z (M+1) 411.3, (M−1) 409.2, TLC 70% ethyl acetate/hexane Rf 0.33).

Intermediate 14: Methyl 1-(5-bromo-6-fluoropyridin-2-yl)azetidine-3-carboxylate

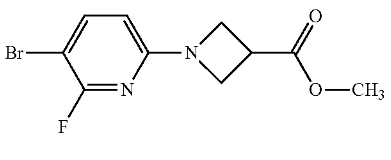 [SMILES: COC(=O)C1CN(c2ccc(Br)c(F)n2)C1]

Step (i):

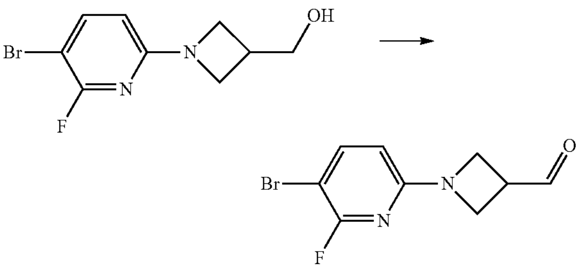

Oxalyl chloride (210 µl, 1.2 eq) was dissolved in DCM (10 ml) and cooled to −78° C. To the reaction was DMSO (290 µl, 2 eq), dissolved in DCM (5 ml), added under 5 min. The reaction was stirred for 5 min then 1-(6-fluoropyridin-2-yl)azetidin-3-yl]methanol (Intermediate 1, 0.50 g. 2.0 mmol), dissolved in DCM (5 ml), was added under 5 min. After 15 min TEA (1.4 ml, 5 eq) added dropwise and, after 10 min, the reaction was allowed to come to rt.

The reaction was quenched with a bicarb solution, extracted with DCM, dried with $MgSO_4$, filtered and the solvent was removed in vacuo to give 1-(5-bromo-6-fluoropyridin-2-yl)azetidine-3-carbaldehyde used as is in the next reaction (0.52 g oil, 100% yield, HPLC Rf 2.65 min, MS m/z (M+1) 259.0, 261.0, (M−1) 257.0, 259.0, TLC 50% ethyl acetate/hexane Rf 0.25).

Step (ii):

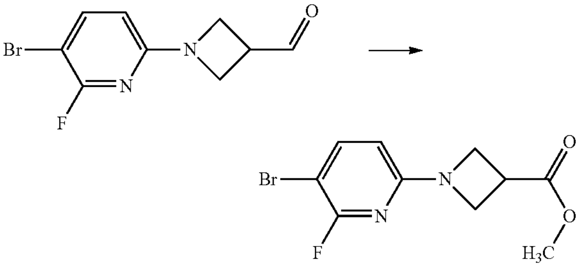

1-(5-Bromo-6-fluoropyridin-2-yl)azetidine-3-carbaldehyde (0.50 g, 2.0 mmol) was dissolved in a t-butanol/water (10:2) solution, sodium phosphate dihydrate (640 mg, 2 eq) and 2-methyl-2-butene were added. The solution was cooled then sodium chlorite (370 mg, 2 eq) was added. The reaction stirred for 1 h at rt.

The reaction mixture was diluted with ethyl acetate, washed with water, treated with brine, dried with $MgSO_4$, filtered and the solvent was removed in vacuo to give the crude product used as is in the next reaction.

The crude intermediate was dissolved in methanol (10 ml), trimethyl orthoformate (1 ml, excess) was added followed by sulfuric acid (100 µl). The reaction stirred at 50° C. for 30 min.

The reaction mixture was diluted with ethyl acetate, washed with water, treated with brine, dried with $MgSO_4$, filtered and the solvent was removed in vacuo to give the crude product.

The crude intermediate was purified on the ISCO (25 g silica, applied with DCM, eluted with 10-20% ethyl acetate/hexane over 4 min) to give methyl 1-(5-bromo-6-fluoropyridin-2-yl)azetidine-3-carboxylate (308 mg oil, 53% yield, HPLC Rf 3.13 min, MS m/z (M+1) 289.0, 291.0, TLC 20% ethyl acetate/hexane Rf 0.23).

Intermediate 15: 1-(5-{1-[(tert-Butoxy)carbonyl]-5-[(tert-butyldimethylsilyl)oxy]-1H-indol-2-yl}-6-fluoropyridin-2-yl)azetidine-3-carboxylic acid

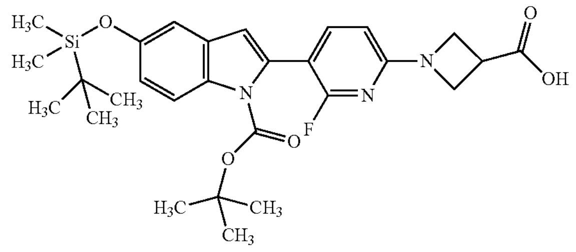 [SMILES: CC(C)(C)OC(=O)n1c(-c2ccc(N3CC(C(=O)O)C3)nc2F)cc2cc(O[Si](C)(C)C(C)(C)C)ccc21]

Step (i):

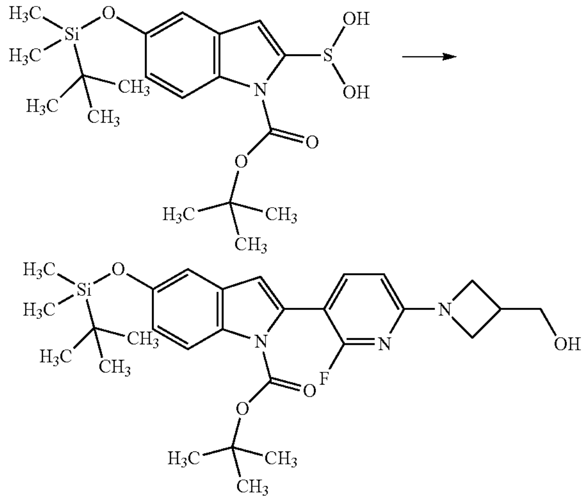

Using the general method 'GP3-1', {1-[(tert-butoxy)carbonyl]-5-[(tert-butyldimethylsilyl)oxy]-1H-indol-2-yl}boronic acid and 1-(5-bromo-6-fluoropyridin-2-yl)azetidin-3-yl]methanol (Intermediate 1) were reacted on a 2.0 mmol scale.

The crude intermediate was purified on the ISCO (25 g silica, applied with DCM, eluted with 30-60% ethyl acetate/hexane over 6 min) to give tert-butyl 5-[(tert-butyldimethylsilyl)oxy]-2-{2-fluoro-6-[3-(hydroxymethyl)azetidin-1-yl]pyridin-3-yl}-1H-indole-1-carboxylate (0.91 g foam, 86% yield, HPLC Rf 4.65 min, MS m/z (M+1) 528.4, TLC 50% ethyl acetate/hexane Rf 0.18).

Step (ii):

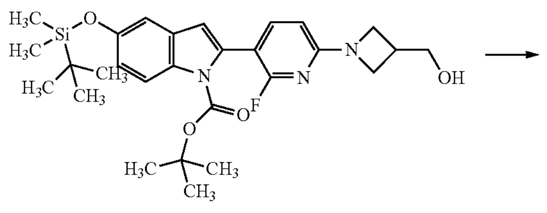

-continued

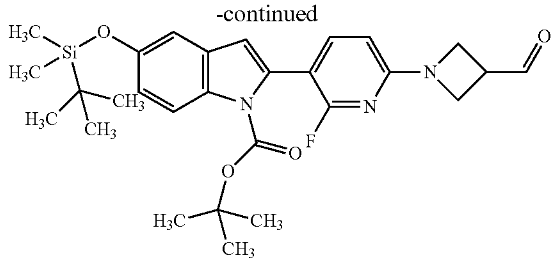

Oxalyl chloride (215 µl, 1.2 eq) was dissolved in DCM (20 ml) and cooled to −78° C. To the reaction was DMSO (300 µl, 2 eq), dissolved in DCM (5 ml), added under 5 min. The reaction was stirred for 5 min then tert-butyl 5-[(tert-butyldimethylsilyl)oxy]-2-{2-fluoro-6-[3-(hydroxymethyl) azetidin-1-yl]pyridin-3-yl}-1H-indole-1-carboxylate (Intermediate 14 Step(i), 1.1 g. 2.1 mmol), dissolved in DCM (5 ml), was added under 5 min. After 15 min TEA (1.5 ml, 5 eq) added dropwise and, after 10 min, the reaction was allowed to come to rt.

The reaction was quenched with a bicarb solution, extracted with DCM, dried with $MgSO_4$, filtered and the solvent was removed in vacuo to give the crude product.

The crude intermediate was purified on the ISCO (25 g silica, applied with DCM, eluted with 35% ethyl acetate/hexane over 4 min) to give tert-butyl 5-[(tert-butyldimethylsilyl)oxy]-2-[2-fluoro-6-(3-formylazetidin-1-yl)pyridin-3-yl]-1H-indole-1-carboxylate (0.87 g foam, 79% yield, HPLC Rf 4.80 min, MS m/z (M+1) 526.4, (M−1) 524.4, TLC 40% ethyl acetate/hexane Rf 0.22).

Step (iii):

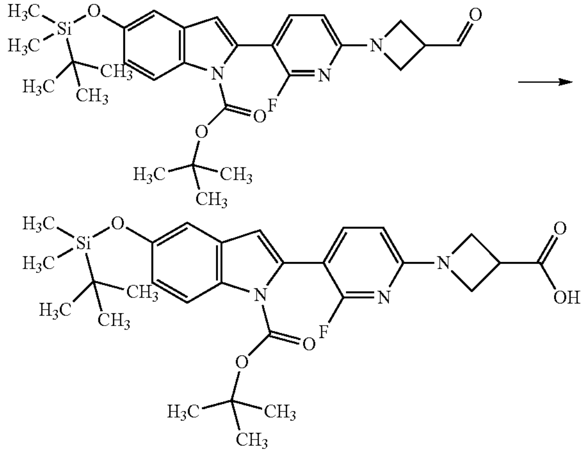

tert-Butyl 5-[(tert-butyldimethylsilyl)oxy]-2-[2-fluoro-6-(3-formylazetidin-1-yl)pyridin-3-yl]-1H-indole-1-carboxylate (106 mg, 0.20 mmol) was dissolved in DCMt-butanol (3 ml) and water (0.6 ml) and to the reaction was dihydrogen phosphate hydrate (55 mg, 2 eq) was added. After stirring for 10 min, 2-methyl.2-butene (640 µl, 30 eq) was added and the reaction was cooled on an ice-bath. Sodium chloride (22 mg, 1.2 eq), dissolved in water (400 µl) was added dropwise. After 5 min the ice-bath was removed and the reaction stirred for 15 min at rt.

The reaction was cooled on an ice-bath, quenched with a 10% sodium thiosulfate solution (1 ml), then taken into ethyl acetate, washed with water, treated with brine, dried with $MgSO_4$, filtered and the solvent was removed in vacuo to give the crude product.

The crude intermediate was purified on the ISCO (4 g silica, applied with DCM, eluted with ethyl acetate/hexane) to give 1-(5-{1-[(tert-butoxy)carbonyl]-5-[(tert-butyldimethylsilyl)oxy]-1H-indol-2-yl}-6-fluoropyridin-2-yl)azetidine-3-carboxylic acid (83 mg solid, 77% yield, HPLC Rf 3.94 min, MS m/z (M+1) 542.5, (M−1) 540.4, TLC ethyl acetate $R^f$ 0.16).

Example Compounds

Example Compound 1: 1-[5-(6-Methoxy-1,3-benzothiazol-2-yl)pyridin-2-yl]piperidin-3-ol

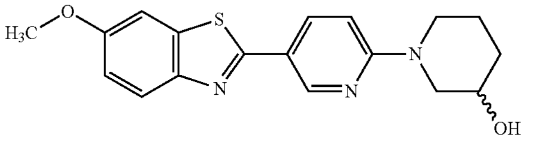 [SMILES: COc1ccc2nc(-c3ccc(N4CCCC(O)C4)nc3)sc2c1]

Using the general method 'GP1', Intermediate 5 (2-(6-chloropyridin-3-yl)-6-methoxy-1,3-benzothiazole) and 3-hydroxypiperidine were reacted to give 1-[5-(6-methoxy-1,3-benzothiazol-2-yl)pyridin-2-yl]piperidin-3-ol (25 mg solid, 71% yield, HPLC Rf 3.00 min, MS m/z (M+1) 342.2, (M−1) 340.2).

Example Compound 2: (3R)-1-[5-(6-Methoxy-1,3-benzothiazol-2-yl)pyridin-2-yl]pyrrolidin-3-ol

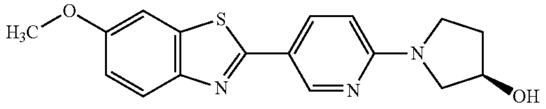 [SMILES: COc1ccc2nc(-c3ccc(N4CC[C@@H](O)C4)nc3)sc2c1]

Using the general method 'GP1', 2-(6-chloropyridin-3-yl)-6-methoxy-1,3-benzothiazole (intermediate 5) and (R)-3-hydroxypyrrolidine were reacted to give (3R)-1-[5-(6-methoxy-1,3-benzothiazol-2-yl)pyridin-2-yl]pyrrolidin-3-ol) (12 mg solid, 39% yield, HPLC Rf 2.79 min, MS m/z (M+1) 328.2, (M−1) 326.3).

Example Compound 3: (3S)-1-[5-(6-Methoxy-1,3-benzothiazol-2-yl)pyridin-2-yl]pyrrolidin-3-ol

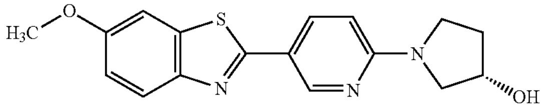

Using the general method 'GP1', 2-(6-chloropyridin-3-yl)-6-methoxy-1,3-benzothiazole (intermediate 5) and (S)-3-hydroxypyrrolidine were reacted to give (3R)-1-[5-(6-methoxy-1,3-benzothiazol-2-yl)pyridin-2-yl]pyrrolidin-3-ol) (15 mg solid, 50% yield, HPLC Rf 2.78 min, MS m/z (M+1) 328.2, (M−1) 326.1).

Example Compounds of Structure 1

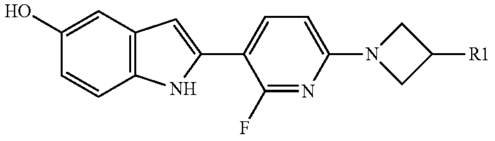

Example Compound 4: 2-{2-Fluoro-6-[3-(hydroxymethyl)azetidin-1-yl]pyridin-3-yl}-1H-indol-5-ol (R1=$CH_2OH$)

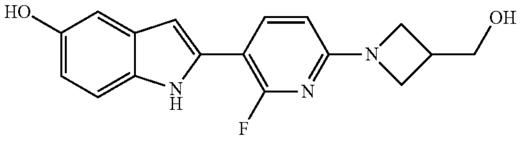 [SMILES: OCC1CN(c2ccc(-c3cc4cc(O)ccc4[nH]3)c(F)n2)C1]

Step (i)

Using the general method 'GP3-1', {1-[(tert-butoxy)carbonyl]-5-[(tert-butyldimethylsilyl)oxy]-1H-indol-2-yl}boronic acid and [1-(5-bromo-6-fluoropyridin-2-yl)azetidin-3-yl]methanol (intermediate 1) were reacted on a 1 mmol scale.

The crude intermediate was purified on the ISCO (25 g silica, applied with DCM, eluted with 20-60% ethyl acetate/hexane over 6 min) to give tert-butyl 5-[(tert-butyldimethylsilyl)oxy]-2-{2-fluoro-6-[3-(hydroxymethyl)azetidin-1-yl]pyridin-3-yl}-1H-indole-1-carboxylate (470 mg foam, 84% yield, HPLC Rf 4.45 min, MS m/z (M+1) 528.4, TLC 50% ethyl acetate/hexane Rf 0.18).

Step (ii)

Using the general method 'GP3-2', tert-butyl 5-[(tert-butyldimethylsilyl)oxy]-2-{2-fluoro-6-[3-(hydroxymethyl)azetidin-1-yl]pyridin-3-yl}-1H-indole-1-carboxylate (100 mg, 0.19 mmol) was reacted to remove the silyl protecting group.

The crude intermediate was purified on the ISCO (12 g silica, applied with DCM, eluted with 40-70% ethyl acetate/hexane over 6 min) to give tert-butyl 2-{2-fluoro-6-[3-(hydroxymethyl)azetidin-1-yl]pyridin-3-yl}-5-hydroxy-1H-indole-1-carboxylate (34 mg solid, 44% yield, HPLC Rf 2.89 min, MS m/z (M+1) 414.3, (M−1) 412.2, TLC 70% ethyl acetate/hexane Rf 0.20).

Step (iii)

Using the general method 'GP3-3', tert-butyl 2-{2-fluoro-6-[3-(hydroxymethyl)azetidin-1-yl]pyridin-3-yl}-5-hydroxy-1H-indole-1-carboxylate was reacted to remove the BOC group to give 2-{2-fluoro-6-[3-(hydroxymethyl)azetidin-1-yl]pyridin-3-yl}-1H-indol-5-ol (20 mg solid, 77% yield, HPLC Rf 2.19 min, MS m/z (M+1) 314.2, (M−1) 312.2).

Example Compound 5: 2-{2-Fluoro-6-[3-(hydroxyethyl)azetidin-1-yl]pyridin-3-yl}-1H-indol-5-ol ($R1=CH_2CH_2OH$)

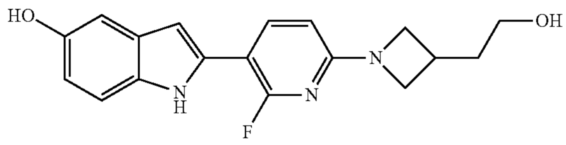 [SMILES: OCCC1CN(c2ccc(-c3cc4cc(O)ccc4[nH]3)c(F)n2)C1]

Step (i)

Using the general method 'GP3-1', {1-[(tert-butoxy)carbonyl]-5-[(tert-butyldimethylsilyl)oxy]-1H-indol-2-yl}boronic acid and [1-(5-bromo-6-fluoropyridin-2-yl)azetidin-3-yl]ethanol (intermediate 2) were reacted on a 0.76 mmol scale.

The crude intermediate was purified on the ISCO (12 g silica, applied with DCM, eluted with 20-50% ethyl acetate/hexane over 4 min) to give tert-butyl 5-[(tert-butyldimethylsilyl)oxy]-2-{2-fluoro-6-[3-(hydroxyethyl)azetidin-1-yl]pyridin-3-yl}-1H-indole-1-carboxylate (350 mg foam, 86% yield, HPLC Rf 4.50 min, MS m/z (M+1) 542.4, TLC 50% ethyl acetate/hexane Rf 0.20).

Step (ii)

Using the general method 'GP3-2', tert-butyl 5-[(tert-butyldimethylsilyl)oxy]-2-{2-fluoro-6-[3-(hydroxyethyl)azetidin-1-yl]pyridin-3-yl}-1H-indole-1-carboxylate (150 mg, 0.28 mmol) was reacted to remove the silyl protecting group.

The crude intermediate was purified on the ISCO (12 g silica, applied with DCM, eluted with 40-70% ethyl acetate/hexane over 4 min) to give tert-butyl 2-{2-fluoro-6-[3-(hydroxyethyl)azetidin-1-yl]pyridin-3-yl}-5-hydroxy-1H-indole-1-carboxylate (84 mg foam, 71% yield, HPLC Rf 2.99 min, MS m/z (M+1) 428.3, (M−1) 426.4, TLC 70% ethyl acetate/hexane Rf 0.24).).

Step (iii)

Using the general method 'GP3-3', tert-butyl 2-{2-fluoro-6-[3-(hydroxyethyl)azetidin-1-yl]pyridin-3-yl}-5-hydroxy-1H-indole-1-carboxylate was reacted to remove the BOC group to give the crude product. Purification of the crude product was carried out on the semi-prep to give 2-{2-fluoro-6-[3-(hydroxyethyl)azetidin-1-yl]pyridin-3-yl}-1H-indol-5-ol (13 mg solid, 20% yield, HPLC Rf 2.33 min, MS m/z (M+1) 328.2, (M−1) 326.2).

Example Compound 6: 2-{2-Fluoro-6-[(3R)-3-hydroxypiperidin-1-yl]pyridin-3-yl}-1H-indol-5-ol

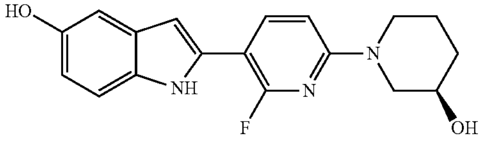 [SMILES: Oc1ccc2[nH]c(-c3ccc(N4CCC[C@@H](O)C4)nc3F)cc2c1]

Step (i)

Using the general method 'GP3-1', {1-[(tert-butoxy)carbonyl]-5-[(tert-butyldimethylsilyl)oxy]-1H-indol-2-yl}boronic acid and [(3R)-1-(5-bromo-6-fluoropyridin-2-yl)piperidin-3-ol (intermediate 3) were reacted on a 1 mmol scale.

The crude intermediate was purified on the ISCO (25 g silica, applied with DCM, eluted with 15-35% ethyl acetate/hexane over 6 min) to give tert-butyl 5-[(tert-butyldimethylsilyl)oxy]-2-{2-fluoro-6-[(3R)-3-hydroxypiperidin-1-yl]pyridin-3-yl}-1H-indole-1-carboxylate (490 mg foam, 90% yield, HPLC Rf 4.56 min, MS m/z (M+1) 542.5, TLC 50% ethyl acetate/hexane Rf 0.49).

Step (ii)

Using the general method 'GP3-2', tert-butyl 5-[(tert-butyldimethylsilyl)oxy]-2-{2-fluoro-6-[(3R)-3-hydroxypiperidin-1-yl]pyridin-3-yl}-1H-indole-1-carboxylate (144 mg, 0.27 mmol) was reacted to remove the silyl protecting group.

The crude intermediate was purified on the ISCO (12 g silica, applied with DCM, eluted with 30-55% ethyl acetate/hexane over 6 min) to give tert-butyl 2-{2-fluoro-6-[(3R)-3-hydroxypiperidin-1-yl]pyridin-3-yl}-5-hydroxy-1H-indole-1-carboxylate (108 mg foam, 95% yield, HPLC Rf 3.15 min, MS m/z (M+1) 428.3, (M−1) 426.2, TLC 50% ethyl acetate/hexane Rf 0.25).).

Step (iii)

Using the general method 'GP3-3', tert-butyl 2-{2-fluoro-6-[(3R)-3-hydroxypiperidin-1-yl]pyridin-3-yl}-5-hydroxy-1H-indole-1-carboxylate was reacted to remove the BOC group to give the crude product. Purification of the crude product was carried on the ISCO (4 g silica, applied with DCM, eluted with 50-100% ethyl acetate/hexane) to give 2-{2-fluoro-6-[(3R)-3-hydroxypiperidin-1-yl]pyridin-3-yl}-1H-indol-5-ol (55 mg solid, 66% yield, HPLC Rf 2.52 min, MS m/z (M+1) 328.2, (M−1) 326.2, TLC ethyl acetate Rf 0.48).

Example Compound 7: 2-{2-Fluoro-6-[(3S)-3-hydroxypiperidin-1-yl]pyridin-3-yl}-1H-indol-5-ol

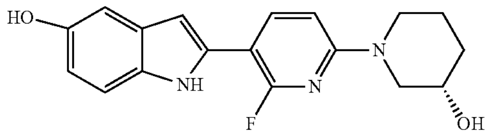 [SMILES: Oc1ccc2[nH]c(-c3ccc(N4CCC[C@H](O)C4)nc3F)cc2c1]

Step (i)

Using the general method 'GP3-1', {1-[(tert-butoxy)carbonyl]-5-[(tert-butyldimethylsilyl)oxy]-1H-indol-2-yl}boronic acid and [(3S)-1-(5-bromo-6-fluoropyridin-2-yl)piperidin-3-ol (intermediate 4) were reacted on a 1 mmol scale.

The crude intermediate was purified on the ISCO (25 g silica, applied with DCM, eluted with 15-35% ethyl acetate/hexane over 5 min) to give tert-butyl 5-[(tert-butyldimethylsilyl)oxy]-2-{2-fluoro-6-[(3S)-3-hydroxypiperidin-1-yl]pyridin-3-yl}-1H-indole-1-carboxylate (433 mg foam, 80% yield, HPLC Rf 4.60 min, MS m/z (M+1) 542.4, TLC 50% ethyl acetate/hexane Rf 0.49).

Step (ii)

Using the general method 'GP3-2', tert-butyl 5-[(tert-butyldimethylsilyl)oxy]-2-{2-fluoro-6-[(3S)-3-hydroxypiperidin-1-yl]pyridin-3-yl}-1H-indole-1-carboxylate (144 mg, 0.27 mmol) was reacted to remove the silyl protecting group.

The crude intermediate was purified on the ISCO (12 g silica, applied with DCM, eluted with 30-55% ethyl acetate/hexane over 5 min) to give tert-butyl 2-{2-fluoro-6-[(3S)-3-hydroxypiperidin-1-yl]pyridin-3-yl}-5-hydroxy-1H-indole-1-carboxylate (108 mg foam, 95% yield, HPLC Rf 3.15 min, MS m/z (M+1) 428.3, (M−1) 426.3, TLC 50% ethyl acetate/hexane Rf 0.25).

Step (iii)

Using the general method 'GP3-3', tert-butyl 2-{2-fluoro-6-[(3R)-3-hydroxypiperidin-1-yl]pyridin-3-yl}-5-hydroxy-1H-indole-1-carboxylate was reacted to remove the BOC group to give the crude product. Purification of the crude product was carried out using the centrifuge (×4) with water (solution removed each time), then with methanol (loss of compound) and finally with ether to give 2-{2-fluoro-6-[(3S)-3-hydroxypiperidin-1-yl]pyridin-3-yl}-1H-indol-5-ol (25 mg solid, 30% yield, HPLC Rf 2.53 min, MS m/z (M+1) 328.2, (M−1) 326.2).

Example Compound 8: (3R,4R)-1-[5-(6-Methoxy-1,3-benzothiazol-2-yl)pyridin-2-yl]piperidine-3,4-diol

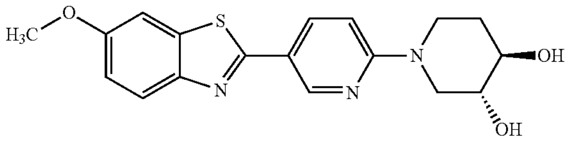 [SMILES: COc1ccc2nc(-c3ccc(N4CC[C@@H](O)[C@H](O)C4)nc3)sc2c1]

Using the general method 'GP1', 2-(6-chloropyridin-3-yl)-6-methoxy-1,3-benzothiazole (Intermediate 5) and (3R,4R)-piperidine-3,4-diol were reacted on the microwave for 8 h at 150° C. to give (3R,4R)-1-[5-(6-methoxy-1,3-benzothiazol-2-yl)pyridin-2-yl]piperidine-3,4-diol (30 mg solid, 75% yield, HPLC Rf 2.67 min, MS m/z (M+1) 358.2, (M−1) 356.1).

Example Compound 9: (3R,4S)-1-[5-(6-Methoxy-1,3-benzothiazol-2-yl)pyridin-2-yl]piperidine-3,4-diol

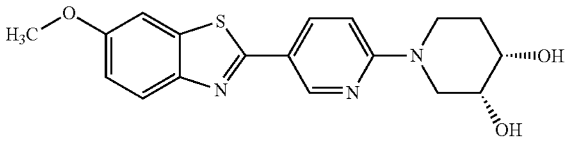 [SMILES: COc1ccc2nc(-c3ccc(N4CC[C@H](O)[C@H](O)C4)nc3)sc2c1]

Using the general method 'GP1', (3R,4S)-1-[5-(6-methoxy-1,3-benzothiazol-2-yl)pyridin-2-yl]piperidine-3,4-diol is made.

Example Compound 10: (3S,4R)-4-(Hydroxymethyl)-1-[5-(6-methoxy-1,3-benzothiazol-2-yl)pyridin-2-yl]piperidin-3-ol

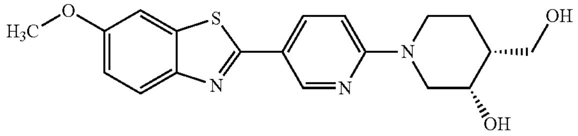 [SMILES: COc1ccc2nc(-c3ccc(N4CC[C@H](CO)[C@H](O)C4)nc3)sc2c1]

Using the general method 'GP1', ((3S,4R)-4-(hydroxymethyl)-1-[5-(6-methoxy-1,3-benzothiazol-2-yl)pyridin-2-yl]piperidin-3-ol is made.

Example Compound 11: (3S,4S)-4-(Hydroxymethyl)-1-[5-(6-methoxy-1,3-benzothiazol-2-yl)pyridin-2-yl]piperidin-3-ol

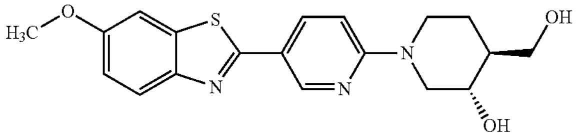 [SMILES: COc1ccc2nc(-c3ccc(N4CC[C@@H](CO)[C@H](O)C4)nc3)sc2c1]

Using the general method 'GP1', 2-(6-chloropyridin-3-yl)-6-methoxy-1,3-benzothiazole (intermediate 5) and (3S,4S)-4-(hydroxymethyl)piperidin-3-ol HCl were reacted on the microwave for 8 h at 150° C. to give: (3S,4S)-4-(hydroxymethyl)-1-[5-(6-methoxy-1,3-benzothiazol-2-yl)pyridin-2-yl]piperidin-3-ol (31 mg solid, 78% yield, HPLC Rf 2.76 min, MS m/z (M+1) 372.2, (M−1) 370.0).

Example Compound 12: (3R,5S)-1-[5-(6-Methoxy-1,3-benzothiazol-2-yl)pyridin-2-yl]piperidine-3,5-diol

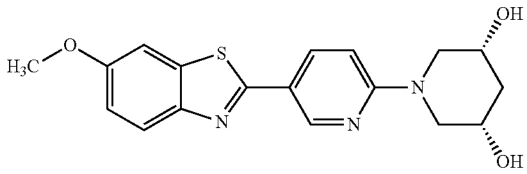 [SMILES: COc1ccc2nc(-c3ccc(N4C[C@H](O)C[C@H](O)C4)nc3)sc2c1]

Using the general method 'GP1', 2-(6-chloropyridin-3-yl)-6-methoxy-1,3-benzothiazole (Intermediate 5, done on 72 μmol in 1 ml methanol) and (3R,5S)-piperidine-3,5-diol were reacted on the microwave for 8 h at 150° C. to (3R,5S)-1-[5-(6-methoxy-1,3-benzothiazol-2-yl)pyridin-2-yl]piperidine-3,5-diol (11 mg solid, 42% yield, HPLC Rf 2.65 min, MS m/z (M+1) 358.2, (M−1) 356.2).

Example Compound 13: (3S,5S)-1-[5-(6-Methoxy-1,3-benzothiazol-2-yl)pyridin-2-yl]piperidine-3,5-diol

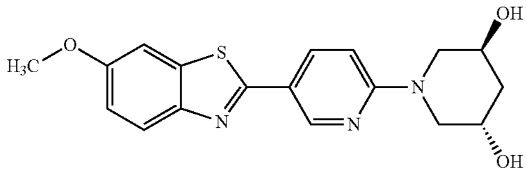 [SMILES: COc1ccc2nc(-c3ccc(N4C[C@@H](O)C[C@H](O)C4)nc3)sc2c1]

Using the general method 'GP1', (3S,5S)-1-[5-(6-methoxy-1,3-benzothiazol-2-yl)pyridin-2-yl]piperidine-3,5-diol is made.

Example Compound 14: 4-(Hydroxymethyl)-1-[5-(6-methoxy-1,3-benzothiazol-2-yl)pyridin-2-yl]piperidin-4-ol

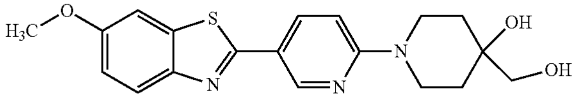 [SMILES: COc1ccc2nc(-c3ccc(N4CCC(O)(CO)CC4)nc3)sc2c1]

Using the general method 'GP1', 2-(6-chloropyridin-3-yl)-6-methoxy-1,3-benzothiazole (Intermediate 5) and 4-(hydroxymethyl)piperidin-4-ol HCl were reacted on the microwave for 8 h at 150° C. to give 4-(hydroxymethyl)-1-[5-(6-methoxy-1,3-benzothiazol-2-yl)pyridin-2-yl]piperidin-4-ol (7 mg solid, 18% yield, HPLC Rf 2.7 min, MS m/z (M+1) 372.2, (M−1) 370.2).

Example Compound 15: (3R,4R)-1-[6-Fluoro-5-(5-hydroxy-1H-indol-2-yl)pyridin-2-yl]piperidine-3,4-diol

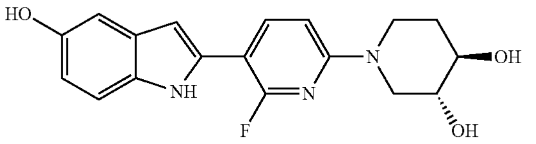 [SMILES: Oc1ccc2[nH]c(-c3ccc(N4CC[C@@H](O)[C@H](O)C4)nc3F)cc2c1]

Using the general method 'GP2' or 'GP3', (3R,4R)-1-[6-fluoro-5-(5-hydroxy-1H-indol-2-yl)pyridin-2-yl]piperidine-3,4-diol is made.

Example Compound 16: (3R,4S)-1-[6-Fluoro-5-(5-hydroxy-1H-indol-2-yl)pyridin-2-yl]piperidine-3,4-diol

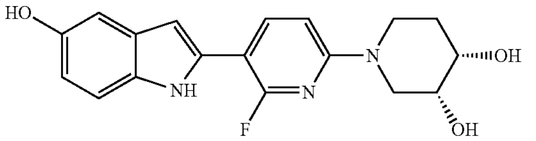 [SMILES: Oc1ccc2[nH]c(-c3ccc(N4CC[C@H](O)[C@H](O)C4)nc3F)cc2c1]

Using the general method 'GP2' or 'GP3', (3R,4S)-1-[6-fluoro-5-(5-hydroxy-1H-indol-2-yl)pyridin-2-yl]piperidine-3,4-diol is made.

Example Compound 17: 2-{2-Fluoro-6-[(3S,4R)-3-hydroxy-4-(hydroxymethyl)piperidin-1-yl]pyridin-3-yl}-1H-indol-5-ol

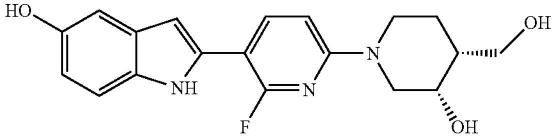 [SMILES: OC[C@H]1CCN(c2ccc(-c3cc4cc(O)ccc4[nH]3)c(F)n2)C[C@H]1O]

Using the general method 'GP2' or 'GP3', 2-{2-fluoro-6-[(3S,4R)-3-hydroxy-4-(hydroxymethyl)piperidin-1-yl]pyridin-3-yl}-1H-indol-5-ol is made.

Example Compound 18: 2-{2-Fluoro-6-[(3S,4S)-3-hydroxy-4-(hydroxymethyl)piperidin-1-yl]pyridin-3-yl}-1H-indol-5-ol

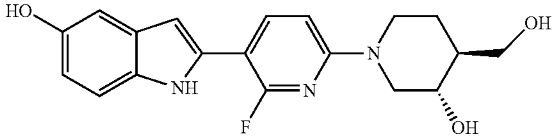 [SMILES: OC[C@@H]1CCN(c2ccc(-c3cc4cc(O)ccc4[nH]3)c(F)n2)C[C@H]1O]

Using the general method 'GP2', tert-butyl 2-(2,6-difluoropyridin-3-yl)-5-hydroxy-1H-indole-1-carboxylate (Intermediate 8) and (3S,4S)-4-(hydroxymethyl)piperidin-3-ol HCl were reacted in acetonitrile to give 2-{2-fluoro-6-[(3R,4S)-3-hydroxy-4-(hydroxymethyl)piperidin-1-yl]pyridin-3-yl}-1H-indol-5-ol (11 mg solid, 33% yield, HPLC Rf 2.24 min, MS m/z (M+1) 358.2, (M−1) 356.2).

Example Compound 19: (3S,5S)-1-[6-Fluoro-5-(5-hydroxy-1H-indol-2-yl)pyridin-2-yl]piperidine-3,5-diol

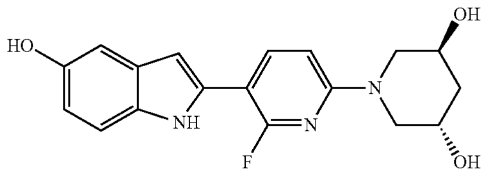 [SMILES: Oc1ccc2[nH]c(-c3ccc(N4C[C@@H](O)C[C@H](O)C4)nc3F)cc2c1]

Using the general method 'GP2' or 'GP3', (3S,5S)-1-[6-fluoro-5-(5-hydroxy-1H-indol-2-yl)pyridin-2-yl]piperidine-3,5-diol is made.

Example Compound 20: (3R,5S)-1-[6-Fluoro-5-(5-hydroxy-1H-indol-2-yl)pyridin-2-yl]piperidine-3,5-diol

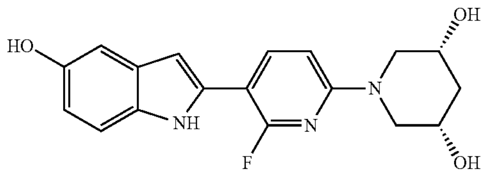

Using the general method 'GP2' or 'GP3', (3R,5S)-1-[6-fluoro-5-(5-hydroxy-1H-indol-2-yl)pyridin-2-yl]piperidine-3,5-diol is made.

Example Compound 21: 2-{2-Fluoro-6-[4-hydroxy-4-(hydroxymethyl)piperidin-1-yl]pyridin-3-yl}-1H-indol-5-ol

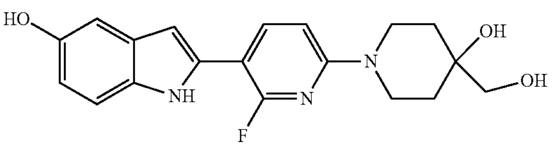 [SMILES: OCC1(O)CCN(c2ccc(-c3cc4cc(O)ccc4[nH]3)c(F)n2)CC1]

Step (i):

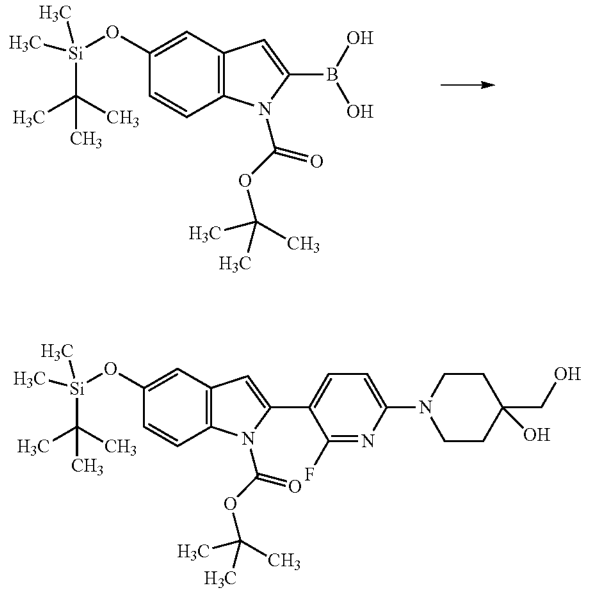

Using the general method 'GP3-1', {1-[(tert-butoxy)carbonyl]-5-[(tert-butyldimethylsilyl)oxy]-1H-indol-2-yl}boronic acid and 1-(5-bromo-6-fluoropyridin-2-yl)-4-(hydroxymethyl)piperidin-4-ol (Intermediate 9) were reacted on a 0.33 mmol scale.

The crude intermediate was purified on the ISCO (12 g silica, applied with DCM, eluted with 60-80% ethyl acetate/hexane over 5 min) to give tert-butyl 5-[(tert-butyldimethylsilyl)oxy]-2-{2-fluoro-6-[4-hydroxy-4-(hydroxymethyl)piperidin-1-yl]pyridin-3-yl}-1H-indole-1-carboxylate (147 mg oil, 78% yield, HPLC Rf 4.43 min, MS m/z (M+1) 572.4, (M−1) 570.4, TLC ethyl acetate Rf 0.31).

Step (ii):

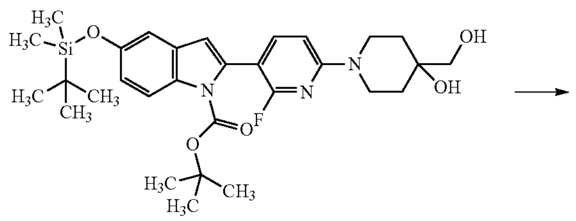

-continued

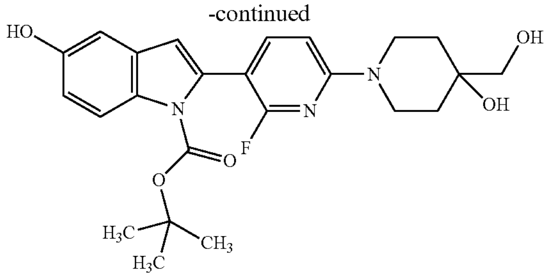

Using the general method 'GP3-2', tert-butyl 5-[(tert-butyldimethylsilyl)oxy]-2-{2-fluoro-6-[4-hydroxy-4-(hydroxymethyl)piperidin-1-yl]pyridin-3-yl}-1H-indole-1-carboxylate (147 mg, 0.26 mmol) was reacted to remove the silyl protecting group.

The crude intermediate was purified on the ISCO (12 g silica, applied with DCM, eluted with 70-90% ethyl acetate/hexane over 5 min) to give tert-butyl 2-{2-fluoro-6-[4-hydroxy-4-(hydroxymethyl)piperidin-1-yl]pyridin-3-yl}-5-hydroxy-1H-indole-1-carboxylate (91 mg oil, 77% yield, HPLC Rf 2.82 min, MS m/z (M+1) 458.3, (M−1) 456.2, TLC ethyl acetate Rf 0.25).

Step (iii):

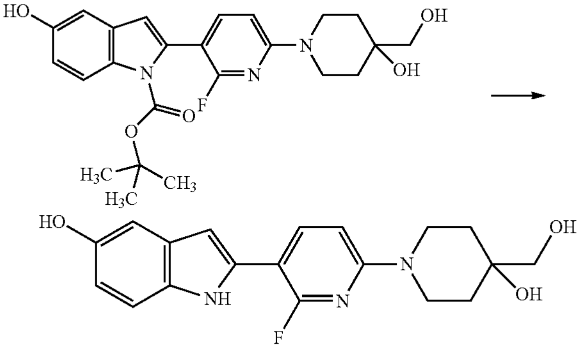

Using a new method, tert-butyl 2-{2-fluoro-6-[4-hydroxy-4-(hydroxymethyl)piperidin-1-yl]pyridin-3-yl}-5-hydroxy-1H-indole-1-carboxylate (90 mg, 0.20 mmol) was dissolved in methanol (4 ml) and subjected to the microwave for 60 min at 150° C.

The reaction mixture was cooled, the solid was filtered and washed with cold methanol to give 2-{2-fluoro-6-[4-hydroxy-4-(hydroxymethyl)piperidin-1-yl]pyridin-3-yl}-1H-indol-5-ol (46 mg solid, 66% yield, HPLC Rf 2.17 min, MS m/z (M+1) 358.3, (M−1) 356.2).

Example Compound 22: 2-{2-Fluoro-6-[4-(hydroxymethyl)piperidin-1-yl]pyridin-3-yl}-1H-indol-6-ol

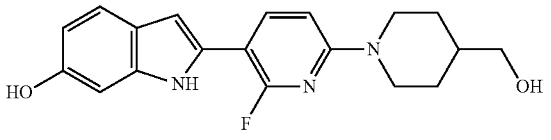 [SMILES: OCC1CCN(c2ccc(-c3cc4ccc(O)cc4[nH]3)c(F)n2)CC1]

Step 1):

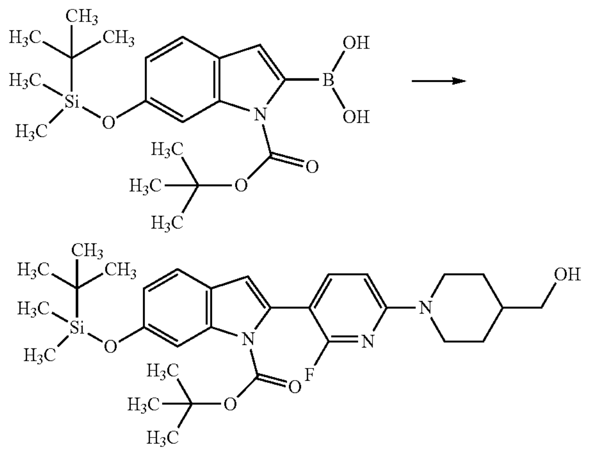

Using the general method 'GP3-1', {1-[(tert-butoxy)carbonyl]-6-[(tert-butyldimethylsilyl)oxy]-1H-indol-2-yl}boronic acid and [1-(5-bromo-6-fluoropyridin-2-yl)piperidin-4-yl]methanol (Intermediate 6) were reacted on a 0.5 mmol scale.

The crude intermediate was purified on the ISCO (25 g silica, applied with DCM, eluted with 15-40% ethyl acetate/hexane over 6 min) to give tert-butyl 6-[(tert-butyldimethylsilyl)oxy]-2-{2-fluoro-6-[4-(hydroxymethyl)piperidin-1-yl]pyridin-3-yl}-1H-indole-1-carboxylate (265 mg oil, 84% yield, HPLC Rf 4.62 min, MS m/z (M+1) 556.4, (M−1) TLC 50% ethyl acetate/hexane Rf 0.24).

Step-2):

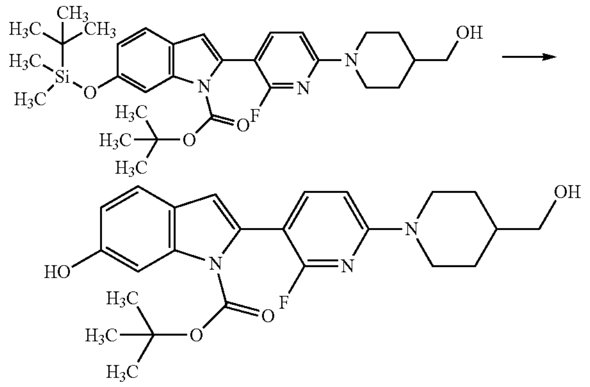

Using the general method 'GP3-2', tert-butyl 6-[(tert-butyldimethylsilyl)oxy]-2-{2-fluoro-6-[4-(hydroxymethyl) piperidin-1-yl]pyridin-3-yl}-1H-indole-1-carboxylate (265 mg, 0.48 mmol) was reacted to remove the silyl protecting group.

The crude intermediate was purified on the ISCO (12 g silica, applied with DCM, eluted with 30-55% ethyl acetate/hexane over 8 min) to give tert-butyl 2-{2-fluoro-6-[4-(hydroxymethyl)piperidin-1-yl]pyridin-3-yl}-6-hydroxy-1H-indole-1-carboxylate (127 mg foam, 60% yield, HPLC Rf 3.20 min, MS m/z (M+1) 442.3, (M−1) 440.2, TLC 50% ethyl acetate/hexane Rf 0.19).

Step 3):

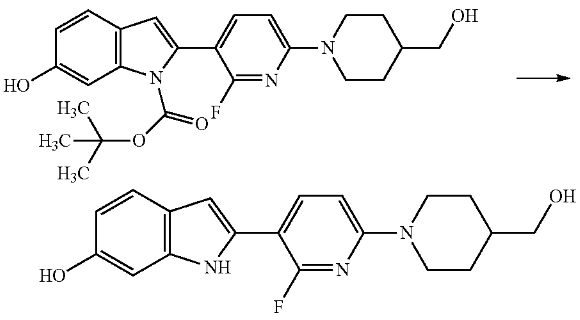

Using a new method, tert-butyl 2-{2-fluoro-6-[4-(hydroxymethyl)piperidin-1-yl]pyridin-3-yl}-6-hydroxy-1H-indole-1-carboxylate (127 mg, 0.29 mmol) was dissolved in methanol (4 ml) and subjected to the microwave for 60 min at 150° C.

The solid was filtered and washed with cold methanol to give 2-{2-fluoro-6-[4-(hydroxymethyl)piperidin-1-yl]pyridin-3-yl}-1H-indol-6-ol (57 mg solid, 60% yield, HPLC Rf 2.55 min, MS m/z (M+1) 342.2, (M−1) 340.1).

Example Compound 23: (3S,4R)-1-[5-(6-Methoxy-1,3-benzothiazol-2-yl)pyridin-2-yl]piperidine-3,4-diol

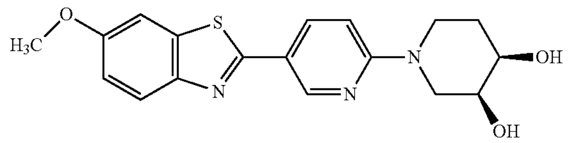 [SMILES: COc1ccc2nc(-c3ccc(N4CC[C@@H](O)[C@@H](O)C4)nc3)sc2c1]

Using the general method 'GP1', 2-(6-chloropyridin-3-yl)-6-methoxy-1,3-benzothiazole (Intermediate 5) and (3S,4R)-piperidine-3,4-diol were reacted on the microwave for 8 h at 150° C. to give (3S,4R)-1-[5-(6-methoxy-1,3-benzothiazol-2-yl)pyridin-2-yl]piperidine-3,4-diol (22 mg solid, 55% yield, HPLC Rf 2.68 min, MS m/z (M+1) 358.2, (M−1) 356.3).

Example Compound 24: (3R,4S)-4-(Hydroxymethyl)-1-[5-(6-methoxy-1,3-benzothiazol-2-yl)pyridin-2-yl]piperidin-3-ol

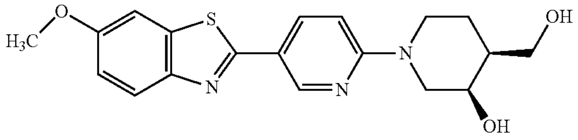 [SMILES: COc1ccc2nc(-c3ccc(N4CC[C@@H](CO)[C@@H](O)C4)nc3)sc2c1]

Using the general method 'GP1', 2-(6-chloropyridin-3-yl)-6-methoxy-1,3-benzothiazole (intermediate 5) and (3R,4S)-4-(hydroxymethyl)piperidin-3-ol HCl were reacted on the microwave for 8 h at 150° C. to give (3R,4S)-4-(hydroxymethyl)-1-[5-(6-methoxy-1,3-benzothiazol-2-yl) pyridin-2-yl]piperidin-3-ol (27 mg solid, 68% yield, HPLC Rf 2.74 min, MS m/z (M+1) 372.2, (M−1) 370.1).

Example Compound 25: (3R,5R)-1-[5-(6-Methoxy-1,3-benzothiazol-2-yl)pyridin-2-yl]piperidine-3,5-diol

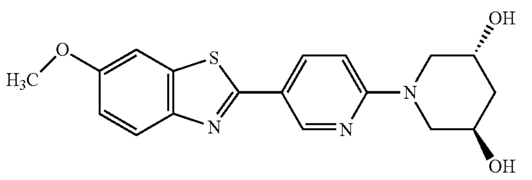 [SMILES: COc1ccc2nc(-c3ccc(N4C[C@H](O)C[C@@H](O)C4)nc3)sc2c1]

Using the general method 'GP1', 2-(6-chloropyridin-3-yl)-6-methoxy-1,3-benzothiazole (Intermediate 5, done on 72 μmol in 1 ml methanol) and (3R,5S)-piperidine-3,5-diol were reacted on the microwave for 8 h at 150° C. to (3R,5R)-1-[5-(6-methoxy-1,3-benzothiazol-2-yl)pyridin-2-yl]piperidine-3,5-diol (15 mg solid, 58% yield, HPLC Rf 2.60 min, MS m/z (M+1) 358.2, (M−1) 356.2).

Example Compound 26: 2-{2-Fluoro-6-[(3R,4S)-3-hydroxy-4-(hydroxymethyl)piperidin-1-yl]pyridin-3-yl}-1H-indol-5-ol

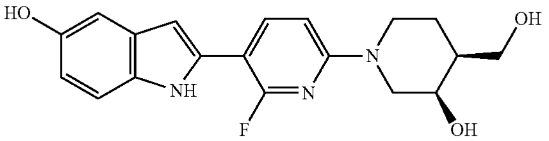 [SMILES: OC[C@@H]1CCN(c2ccc(-c3cc4cc(O)ccc4[nH]3)c(F)n2)C[C@@H]1O]

Using the general method 'GP2', tert-butyl 2-(2,6-difluoropyridin-3-yl)-5-hydroxy-1H-indole-1-carboxylate (Intermediate 8) and (3R,4S)-4-(hydroxymethyl)piperidin-3-ol HCl were reacted in acetonitrile to give 2-{2-fluoro-6-[(3R,4S)-3-hydroxy-4-(hydroxymethyl)piperidin-1-yl]pyridin-3-yl}-1H-indol-5-ol (11 mg solid, 33% yield, HPLC Rf 2.18 min, MS m/z (M+1) 358.2, (M−1) 356.2).

Example Compound 27: 2-{6-[(3R)-3-Hydroxypiperidin-1-yl]pyridin-3-yl}-1H-indol-5-ol

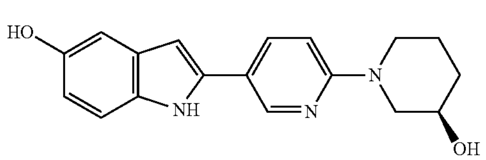

Using a new method, tert-butyl 5-hydroxy-2-{6-[(3R)-3-hydroxypiperidin-1-yl]pyridin-3-yl}-1H-indole-1-carboxylate (Intermediate 11, 39 mg, 95 μmol) was dissolved in methanol (1.5 ml) and subjected to the microwave for 60 min at 150° C.

The solid was filtered and washed with cold methanol to give 2-{6-[(3R)-3-hydroxypiperidin-1-yl]pyridin-3-yl}-1H-indol-5-ol (11 mg solid, 38% yield, HPLC Rf 2.32 min, MS m/z (M+1) 310.2, (M−1) 308.2).

Example Compound 28: (3R)-1-{5-[5-(2-Fluoroethoxy)-1H-indol-2-yl]pyridin-2-yl}piperidin-3-ol

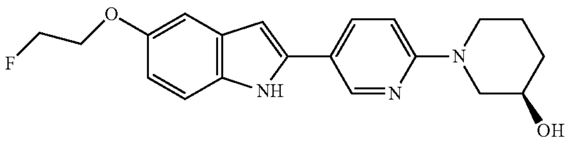 [SMILES: O[C@@H]1CCCN(c2ccc(-c3cc4cc(OCCF)ccc4[nH]3)cn2)C1]

Step-1):

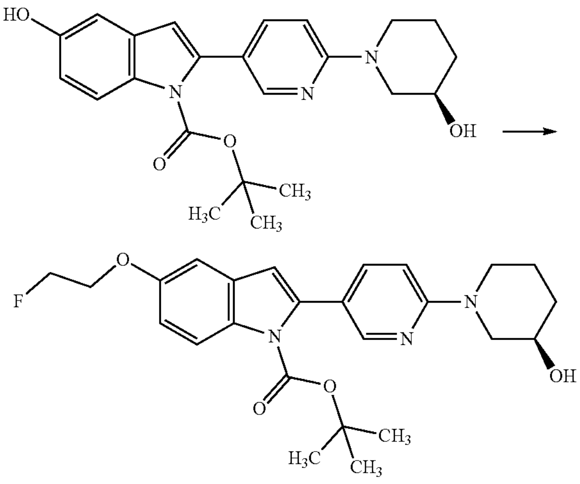

tert-Butyl 5-hydroxy-2-{6-[(3R)-3-hydroxypiperidin-1-yl]pyridin-3-yl}-1(H-indole-1-carboxylate (Intermediate 11, 60 mg, 147 μmol) and 1-fluoro-2-iodoethane (20 μl, 1.5 eq) were dissolved in DMF (800 μl) followed by the addition of by cesium carbonate (120 mg, 2.5 eq). The reaction stirred for 1 h at 40° C.

The reaction mixture was diluted with ethyl acetate, washed with water, treated with brine, dried with $MgSO_4$, filtered and the solvent was removed in vacuo to give the crude product.

The crude intermediate was purified on the ISCO (4 g silica, applied with DCM, eluted with 30-50% ethyl acetate/hexane over 4 min) to give tert-butyl 5-(2-fluoroethoxy)-2-{6-[(3R)-3-hydroxypiperidin-1-yl]pyridin-3-yl}-1H-indole-1-carboxylate (67 mg oil, 100% yield, HPLC Rf 3.52 min, MS m/z (M+1) 456.3, (M−1) 454.3, TLC 70% ethyl acetate/hexane Rf 0.33).

Step 2):

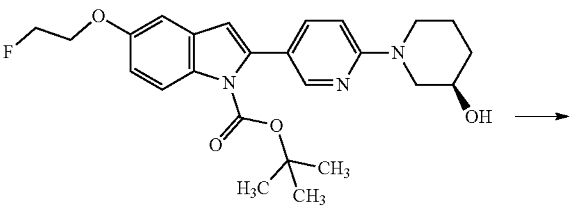

-continued

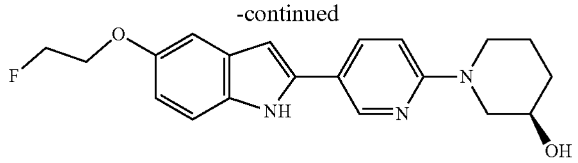

Using a new method, tert-butyl 5-(2-fluoroethoxy)-2-{6-[(3R)-3-hydroxypiperidin-1-yl]pyridin-3-yl}-1H-indole-1-carboxylate (67 mg, 147 μmol) was dissolved in methanol (1.8 ml) and subjected to the microwave for 60 min at 150° C.

The solution was cooled and the solid was filtered and washed with cold methanol to give (3R)-1-{5-[5-(2-fluoroethoxy)-1H-indol-2-yl]pyridin-2-yl}piperidin-3-ol (9 mg solid, 15% yield, HPLC Rf 2.89 min, MS m/z (M+1) 356.2, (M−1) 354.2).

Example Compound 29: (3R)-1-[5-(5-{2-[2-(2-Fluoroethoxy)ethoxy]ethoxy}-1H-indol-2-yl)pyridin-2-yl]piperidin-3-ol

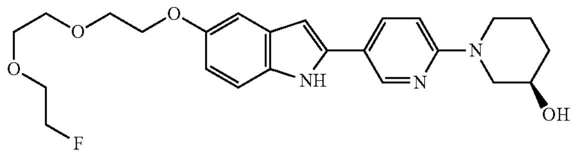 [SMILES: O[C@@H]1CCCN(c2ccc(-c3cc4cc(OCCOCCOCCF)ccc4[nH]3)cn2)C1]

Step-1):

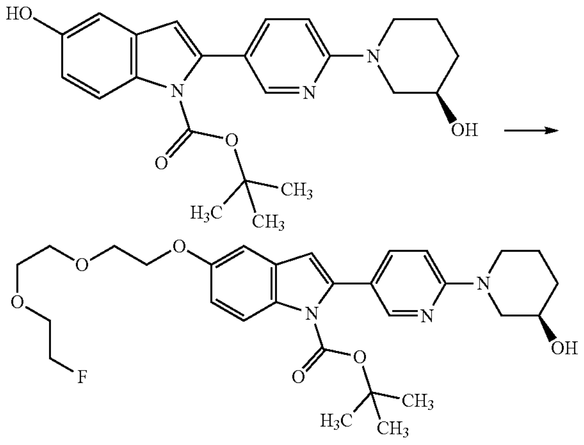

tert-Butyl 5-hydroxy-2-{6-[(3R)-3-hydroxypiperidin-1-yl]pyridin-3-yl}-1(H-indole-1-carboxylate (Intermediate 11, 60 mg, 147 μmol) and 2-[2-(2-fluoroethoxy)ethoxy]ethyl 4-methylbenzene-1-sulfonate (55 μl, 1.5 eq) were dissolved in DMF (1.5 ml) followed the addition of by cesium carbonate (120 mg, 2.5 eq). The reaction stirred for 1 h at 40° C.

The reaction mixture was diluted with ethyl acetate, washed with water, treated with brine, dried with $MgSO_4$, filtered and the solvent was removed in vacuo to give the crude product.

The crude intermediate was purified on the ISCO (4 g silica, applied with DCM, eluted with 40-65% ethyl acetate/hexane over 4 min) to give tert-butyl 5-{2-[2-(2-fluoroethoxy)ethoxy]ethoxy}-2-{6-[(3R)-3-hydroxypiperidin-1-yl]pyridin-3-yl}-1H-indole-1-carboxylate (80 mg oil, 100% yield, HPLC Rf 3.47 min, MS m/z (M+1) 544.4, (M−1) 542.2, TLC 70% ethyl acetate/hexane Rf 0.20).

Step 2):

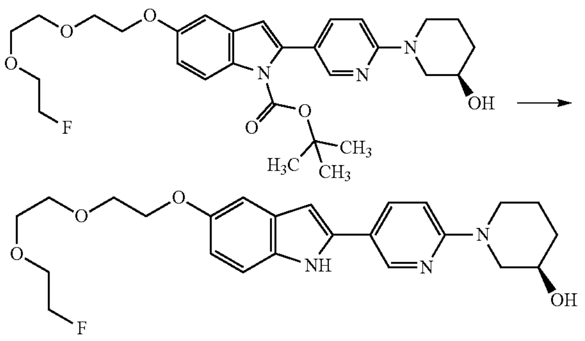

Using a new method, tert-butyl 5-{2-[2-(2-fluoroethoxy)ethoxy]ethoxy}-2-{6-[(3R)-3-hydroxypiperidin-1-yl]pyridin-3-yl}-1H-indole-1-carboxylate (67 mg, 147 μmol) was dissolved in methanol (1.8 ml) and subjected to the microwave for 60 min at 150° C.

The solution was cooled and the solid was filtered and washed with cold methanol to give (3R)-1-[5-(5-{2-[2-(2-fluoroethoxy)ethoxy]ethoxy}-1H-indol-2-yl)pyridin-2-yl]piperidin-3-ol (37 mg solid, 57% yield, HPLC Rf 2.84 min, MS m/z (M+1) 444.2, (M−1) 442.2).

Example Compound 30: 2-{2-[(3R)-3-Hydroxypiperidin-1-yl]pyrimidin-5-yl}-1H-indol-5-ol

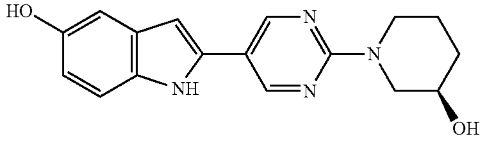 [SMILES: Oc1ccc2[nH]c(-c3cnc(N4CCC[C@@H](O)C4)nc3)cc2c1]

Using a new method, tert-butyl 5-hydroxy-2-{2-[(3R)-3-hydroxypiperidin-1-yl]pyrimidin-5-yl}-1H-indole-1-carboxylate (Intermediate 13, 39 mg, 95 μmol) was dissolved in methanol (1.5 ml) and subjected to the microwave for 60 min at 150° C.

The solid was filtered and washed with cold methanol to give 2-{2-[(3R)-3-hydroxypiperidin-1-yl]pyrimidin-5-yl}-1H-indol-5-ol (21 mg solid, 81% yield, HPLC Rf 2.23 min, MS m/z (M+1) 311.2, (M−1) 309.1).

Example Compound 31: (3R)-1-{5-[5-(2-Fluoroethoxy)-1H-indol-2-yl]pyrimidin-2-yl}piperidin-3-ol

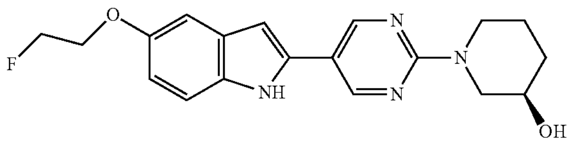 [SMILES: O[C@@H]1CCCN(c2ncc(-c3cc4cc(OCCF)ccc4[nH]3)cn2)C1]

Step-1):

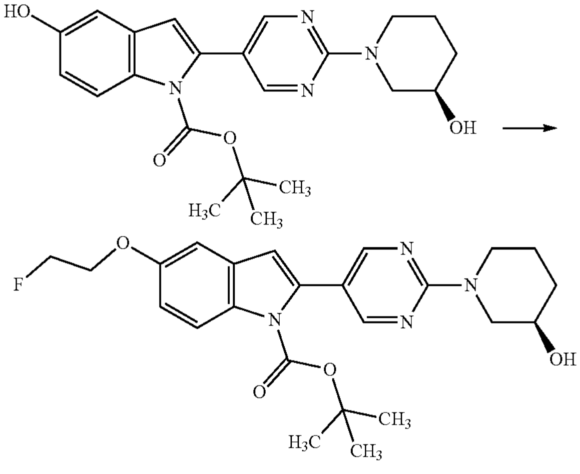

tert-Butyl 5-hydroxy-2-{2-[(3R)-3-hydroxypiperidin-1-yl]pyrimidin-5-yl}-1H-indole-1-carboxylate (Intermediate 13, 60 mg, 147 μmol) and 1-fluoro-2-iodoethane (20 μl, 1.5 eq) were dissolved in DMF (800 μl) followed the addition of by cesium carbonate (120 mg, 2.5 eq). The reaction stirred for 1 h at 40° C.

The reaction mixture was diluted with ethyl acetate, washed with water, treated with brine, dried with $MgSO_4$, filtered and the solvent was removed in vacuo to give the crude product.

The crude intermediate was purified on the ISCO (4 g silica, applied with DCM, eluted with 30-50% ethyl acetate/hexane over 4 min) to give tert-butyl 5-(2-fluoroethoxy)-2-{2-[(3R)-3-hydroxypiperidin-1-yl]pyrimidin-5-yl}-1H-indole-1-carboxylate (58 mg oil, 87% yield, HPLC Rf 3.52 min, MS m/z (M+1) 457.3, TLC 70% ethyl acetate/hexane Rf 0.35).

Step 2):

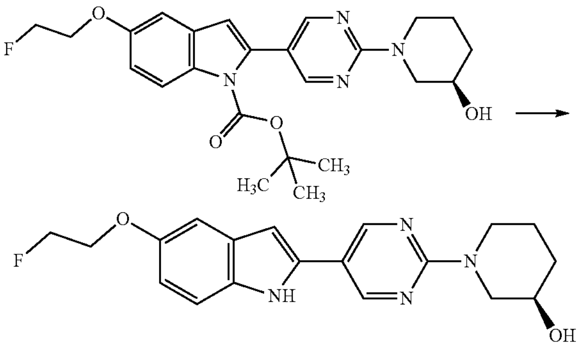

Using a new method, tert-butyl 5-(2-fluoroethoxy)-2-{2-[(3R)-3-hydroxypiperidin-1-yl]pyrimidin-5-yl}-1H-indole-1-carboxylate (58 mg, 127 μmol) was dissolved in methanol (1.8 ml) and subjected to the microwave for 60 min at 150° C.

The solution was cooled, the solid was filtered and washed with cold methanol to give (3R)-1-{5-[5-(2-fluoroethoxy)-1H-indol-2-yl]pyrimidin-2-yl}piperidin-3-ol (10 mg solid, 22% yield, HPLC Rf 2.85 min, MS m/z (M+1) 357.2, (M−1) 355.1).

Example Compound 32: (3R)-1-[5-(5-{2-[2-(2-Fluoroethoxy)ethoxy]ethoxy}-1H-indol-2-yl)pyrimidin-2-yl]piperidin-3-ol

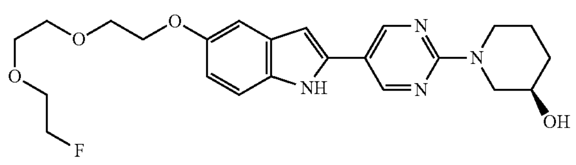 [SMILES: O[C@@H]1CCCN(c2ncc(-c3cc4cc(OCCOCCOCCF)ccc4[nH]3)cn2)C1]

Step-1):

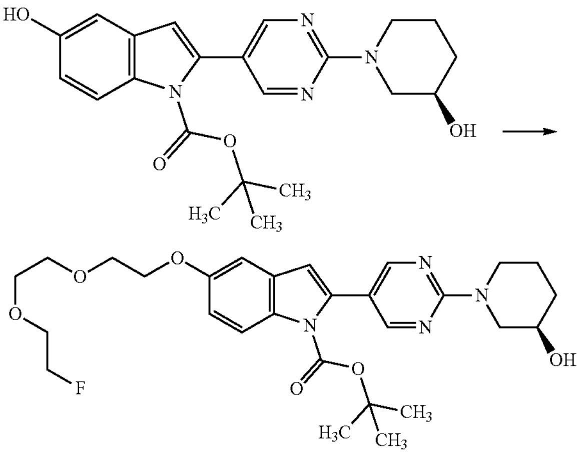

tert-Butyl 5-hydroxy-2-{2-[(3R)-3-hydroxypiperidin-1-yl]pyrimidin-5-yl}-1H-indole-1-carboxylate (Intermediate 13, 60 mg, 147 μmol) and 2-[2-(2-fluoroethoxy)ethoxy]ethyl 4-methylbenzene-1-sulfonate (55 μl, 1.5 eq) were dissolved in DMF (1.5 ml) followed the addition of by cesium carbonate (120 mg, 2.5 eq). The reaction stirred for 1 h at 40° C.

The reaction mixture was diluted with ethyl acetate, washed with water, treated with brine, dried with $MgSO_4$, filtered and the solvent was removed in vacuo to give the crude product.

The crude intermediate was purified on the ISCO (4 g silica, applied with DCM, eluted with 40-65% ethyl acetate/hexane over 4 min) to give tert-butyl 5-{2-[2-(2-fluoroethoxy)ethoxy]ethoxy}-2-{2-[(3R)-3-hydroxypiperidin-1-yl]pyrimidin-5-yl}-1H-indole-1-carboxylate (80 mg oil, 100% yield, HPLC Rf 3.47 min, MS m/z (M+1) 545.4, TLC 70% ethyl acetate/hexane Rf 0.20).

Step 2):

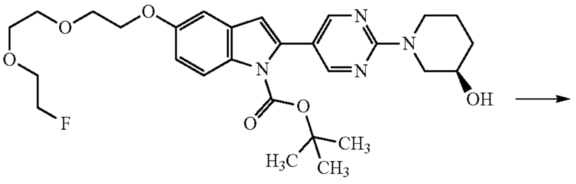

-continued

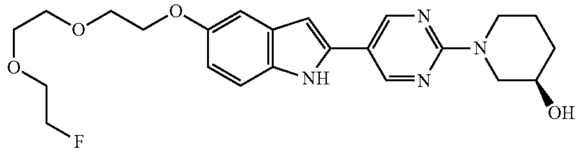

Using a new method, tert-butyl 5-{2-[2-(2-fluoroethoxy)ethoxy]ethoxy}-2-{2-[(3R)-3-hydroxypiperidin-1-yl]pyrimidin-5-yl}-1H-indole-1-carboxylate (80 mg, 147 μmol) was dissolved in methanol (1.9 ml) and subjected to the microwave for 60 min at 150° C.

The solution was cooled and the solid was filtered and washed with cold methanol to give (3R)-1-[5-(5-{2-[2-(2-fluoroethoxy)ethoxy]ethoxy}-1H-indol-2-yl)pyrimidin-2-yl]piperidin-3-ol (44 mg solid, 68% yield, HPLC Rf 2.84 min, MS m/z (M+1) 445.3, (M−1) 443.2).

Example Compound 33: Methyl 1-[6-Fluoro-5-(5-hydroxy-1H-indol-2-yl)pyridin-2-yl]azetidine-3-carboxylate

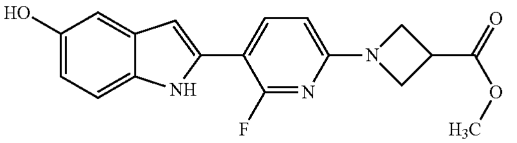 [SMILES: COC(=O)C1CN(c2ccc(-c3cc4cc(O)ccc4[nH]3)c(F)n2)C1]

Step (i):

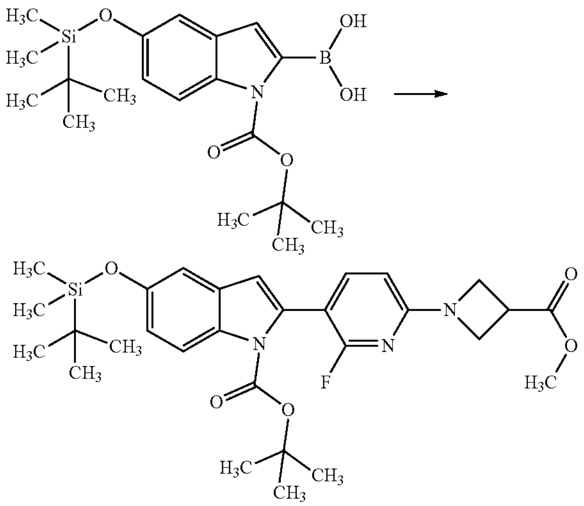

Using the general method 'GP3-1', {1-[(tert-butoxy)carbonyl]-5-[(tert-butyldimethylsilyl)oxy]-1H-indol-2-yl}boronic acid and methyl 1-(5-bromo-6-fluoropyridin-2-yl)azetidine-3-carboxylate (Intermediate 14) were reacted on a 0.5 mmol scale.

The crude intermediate was purified on the ISCO (25 g silica, applied with DCM, eluted with 10-20% ethyl acetate/hexane over 5 min) to give tert-butyl 5-[(tert-butyldimethylsilyl)oxy]-2-{2-fluoro-6-[3-(methoxycarbonyl)azetidin-1-yl]pyridin-3-yl}-1H-indole-1-carboxylate (197 mg oil, 72% yield, HPLC Rf 4.62 min, MS m/z (M+1) 556.4, TLC 30% ethyl acetate/hexane Rf 0.24).

Step (ii):

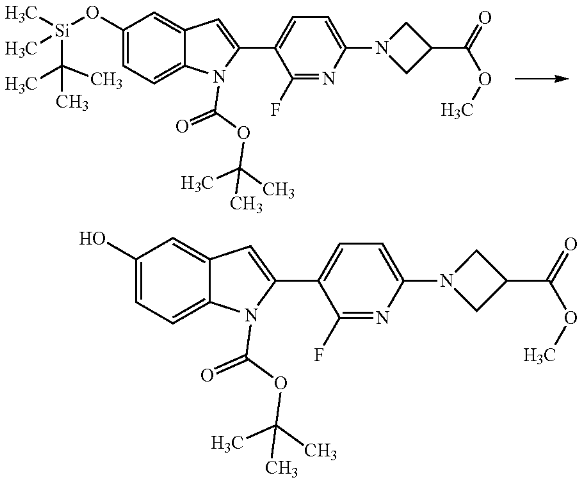

Using the general method 'GP3-2', tert-butyl 5-[(tert-butyldimethylsilyl)oxy]-2-{2-fluoro-6-[3-(methoxycarbonyl)azetidin-1-yl]pyridin-3-yl}-1H-indole-1-carboxylate (190 mg, 0.34 mmol) was reacted to remove the silyl protecting group.

The crude intermediate was purified on the ISCO (12 g silica, applied with DCM, eluted with 20-35% ethyl acetate/hexane over 54 min) to give tert-butyl 2-{2-fluoro-6-[3-(methoxycarbonyl)azetidin-1-yl]pyridin-3-yl}-5-hydroxy-1H-indole-1-carboxylate (20 mg oil, 13% yield, HPLC Rf 3.30 min, MS m/z (M+1) 442.2, (M−1) 440.2, TLC 35% ethyl acetate/hexane Rf 0.15).

Step (iii):

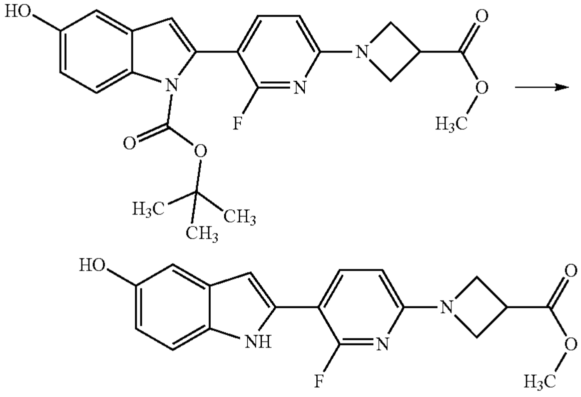

Using a new method, tert-butyl 2-{2-fluoro-6-[3-(methoxycarbonyl)azetidin-1-yl]pyridin-3-yl}-5-hydroxy-1H-indole-1-carboxylate (20 mg, 45 μmol) was dissolved in methanol (1 ml) and subjected to the microwave for 75 min at 150° C.

The reaction mixture was cooled, the solid was filtered and washed with cold methanol to give methyl 1-[6-fluoro-5-(5-hydroxy-1H-indol-2-yl)pyridin-2-yl]azetidine-3-carboxylate (8 mg solid, 53% yield, HPLC Rf 2.66 min, MS m/z (M+1) 342.2, (M−1) 340.1).

Example Compound 34: ($^3H_3$)Methyl 1-[6-fluoro-5-(5-hydroxy-1H-indol-2-yl)pyridin-2-yl]azetidine-3-carboxylate

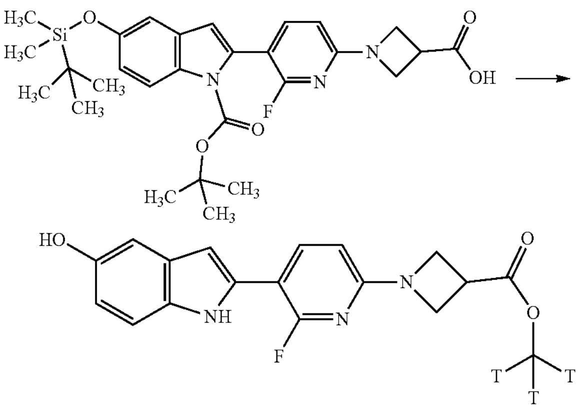

1-(5-{1-[(tert-Butoxy)carbonyl]-5-[(tert-butyldimethylsilyl)oxy]-1H-indol-2-yl}-6-fluoropyridin-2-yl)azetidine-3-carboxylic acid (0.76 mg, 1.4 μmol) was dissolved in DMF (400 μl), potassium carbonate (1.7 mg) was added followed by a DMF solution of [$^3$H]MeI. The reaction stirred for 1 h at rt.

The reaction was diluted with water, extracted with ethyl acetate, treated with brine, dried (sodium sulfate), filtered and the solvent was removed with a stream of nitrogen.

The crude tert-butyl 5-[(tert-butyldimethylsilyl)oxy]-2-(2-fluoro-6-{3-[($^3H_3$)methoxycarbonyl]azetidin-1-yl}pyridin-3-yl)-1H-indole-1-carboxylate was taken into THF (1 ml), cooled on an ice-bath and a 1 M TBAF solution in THF (10 μl) was added. After stirring 10 min the solvent was removed with a stream of nitrogen. The residue was purified on silica eluting with 40-90% ethyl acetate/hexane to give tert-butyl 2-(2-fluoro-6-{3-[($^3H_3$)methoxycarbonyl]azetidin-1-yl}pyridin-3-yl)-5-hydroxy-1H-indole-1-carboxylate.

The purified tert-butyl 2-(2-fluoro-6-{3-[($^3H_3$)methoxycarbonyl]azetidin-1-yl}pyridin-3-yl)-5-hydroxy-1H-indole-1-carboxylate was dissolved in acetonitrile (1 ml) was subjected to the microwave, 1 h at 150° C.

The target compound was purified by HPLC, Kromosil C18, 7 μm 250×10 mm, eluting with 55% acetonitrile in 50 mM ammonium acetate, 2.0 ml/min. The pure fractions were combined and diluted with ethanol (3 ml) to give ($^3H_3$)methyl 1-[6-fluoro-5-(5-hydroxy-1H-indol-2-yl)pyridin-2-yl]azetidine-3-carboxylate (molar activity 82.6 Ci/mmol, 11% yield MS m/z (M+1) 348.3, (M−1) 336.2).

A summary of the structure of example compounds 1 to 33, the C Log P of the compounds, is provided below in Table 1.

TABLE 1

| Example Compound No. | Structure | CLogP |
|---|---|---|
| 1 | 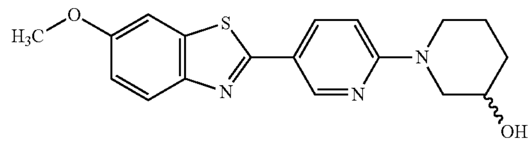 [SMILES: COc1ccc2nc(-c3ccc(N4CCCC(O)C4)nc3)sc2c1] | 3.2 |
| 2 | 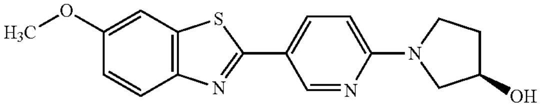 [SMILES: COc1ccc2nc(-c3ccc(N4CC[C@@H](O)C4)nc3)sc2c1] | 2.8 |
| 3 | 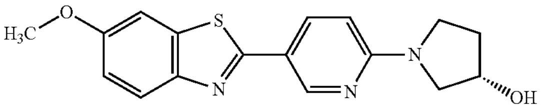 [SMILES: COc1ccc2nc(-c3ccc(N4CC[C@H](O)C4)nc3)sc2c1] | 2.8 |
| 4 | 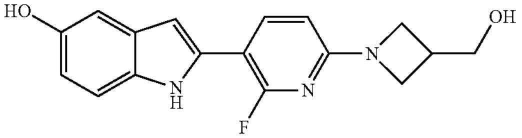 [SMILES: OCC1CN(c2ccc(-c3cc4cc(O)ccc4[nH]3)c(F)n2)C1] | 2.6 |
| 5 | 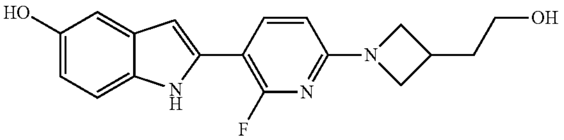 [SMILES: OCCC1CN(c2ccc(-c3cc4cc(O)ccc4[nH]3)c(F)n2)C1] | 2.7 |

TABLE 1-continued
| Example Compound No. | Structure | CLogP |
|---|---|---|
| 6 | 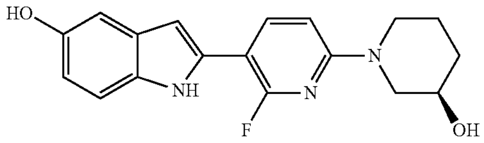 [SMILES: Oc1ccc2[nH]c(-c3ccc(N4CCC[C@@H](O)C4)nc3F)cc2c1] | 3.1 |
| 7 | 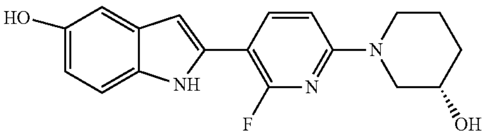 [SMILES: Oc1ccc2[nH]c(-c3ccc(N4CCC[C@H](O)C4)nc3F)cc2c1] | 3.1 |
| 8 | 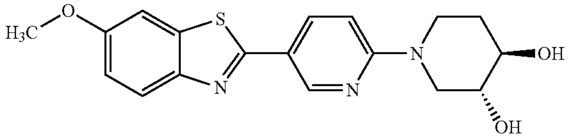 [SMILES: COc1ccc2nc(-c3ccc(N4CC[C@@H](O)[C@H](O)C4)nc3)sc2c1] | 2.1 |
| 9 | 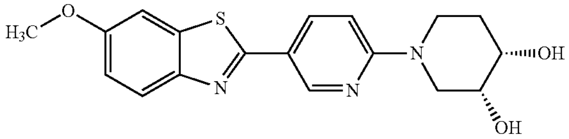 [SMILES: COc1ccc2nc(-c3ccc(N4CC[C@H](O)[C@H](O)C4)nc3)sc2c1] | n.d |
| 10 | 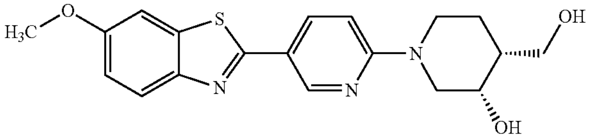 [SMILES: COc1ccc2nc(-c3ccc(N4CC[C@H](CO)[C@H](O)C4)nc3)sc2c1] | n.d |
| 11 | 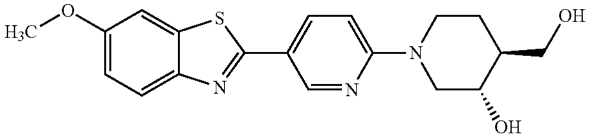 [SMILES: COc1ccc2nc(-c3ccc(N4CC[C@@H](CO)[C@H](O)C4)nc3)sc2c1] | 2.2 |
| 12 | 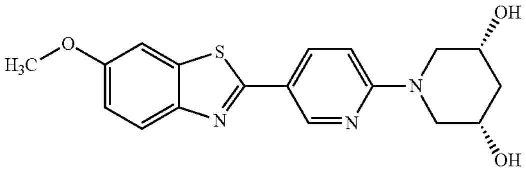 [SMILES: COc1ccc2nc(-c3ccc(N4C[C@H](O)C[C@H](O)C4)nc3)sc2c1] | 2.1 |
| 13 | 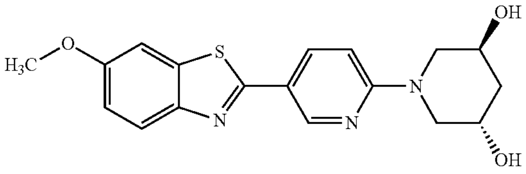 [SMILES: COc1ccc2nc(-c3ccc(N4C[C@@H](O)C[C@H](O)C4)nc3)sc2c1] | n.d |
| 14 | 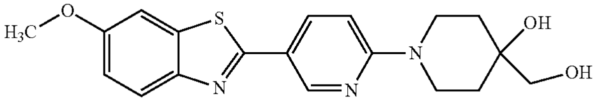 [SMILES: COc1ccc2nc(-c3ccc(N4CCC(O)(CO)CC4)nc3)sc2c1] | 2.0 |
| 15 | 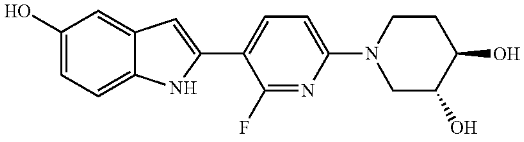 [SMILES: Oc1ccc2[nH]c(-c3ccc(N4CC[C@@H](O)[C@H](O)C4)nc3F)cc2c1] | n.d |

TABLE 1-continued
| Example Compound No. | Structure | CLogP |
|---|---|---|
| 16 | 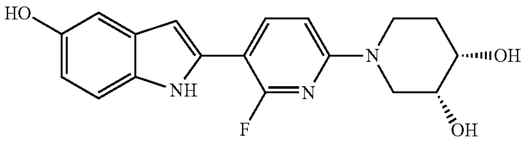 [SMILES: Oc1ccc2[nH]c(-c3ccc(N4CC[C@H](O)[C@H](O)C4)nc3F)cc2c1] | n.d |
| 17 | 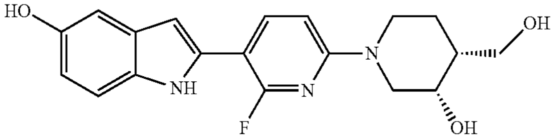 [SMILES: OC[C@H]1CCN(c2ccc(-c3cc4cc(O)ccc4[nH]3)c(F)n2)C[C@H]1O] | n.d |
| 18 | 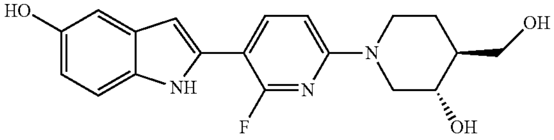 [SMILES: OC[C@@H]1CCN(c2ccc(-c3cc4cc(O)ccc4[nH]3)c(F)n2)C[C@H]1O] | 2.1 |
| 19 | 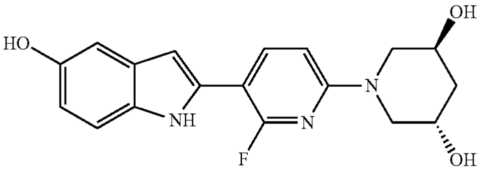 [SMILES: Oc1ccc2[nH]c(-c3ccc(N4C[C@@H](O)C[C@H](O)C4)nc3F)cc2c1] | n.d |
| 20 | 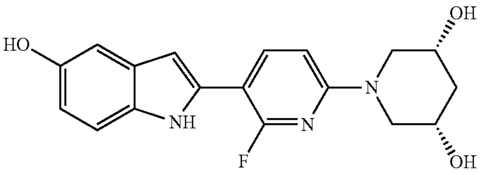 [SMILES: Oc1ccc2[nH]c(-c3ccc(N4C[C@H](O)C[C@H](O)C4)nc3F)cc2c1] | n.d |
| 21 | 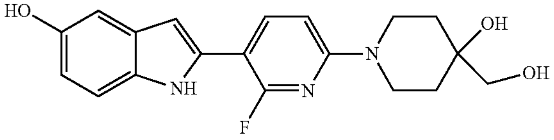 [SMILES: OCC1(O)CCN(c2ccc(-c3cc4cc(O)ccc4[nH]3)c(F)n2)CC1] | 1.9 |
| 22 | 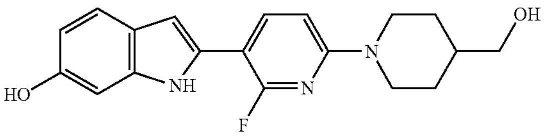 [SMILES: OCC1CCN(c2ccc(-c3cc4ccc(O)cc4[nH]3)c(F)n2)CC1] | 3.1 |
| 23 | 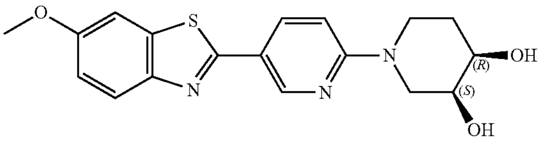 | 2.1 |
| 24 | 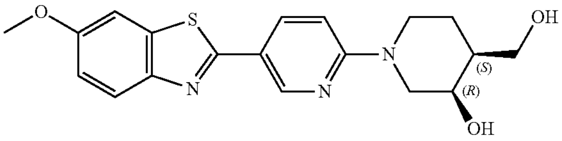 | 2.2 |

TABLE 1-continued
| Example Compound No. | Structure | CLogP |
|---|---|---|
| 25 | 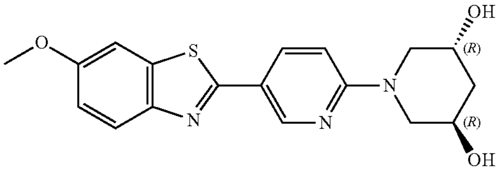 | 2.1 |
| 26 | 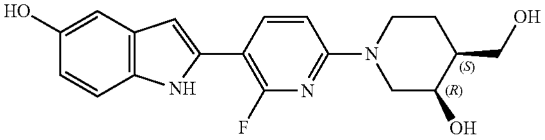 | 2.1 |
| 27 | 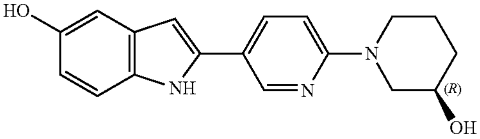 | 2.6 |
| 28 | 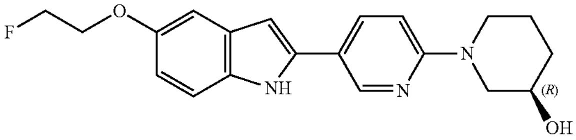 | 2.9 |
| 29 | 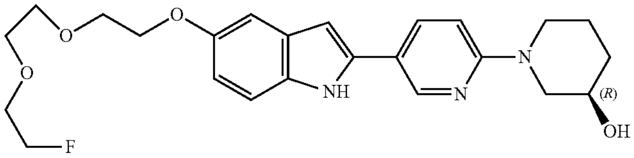 | 2.8 |
| 30 | 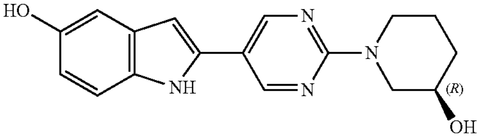 | 2.0 |
| 31 | 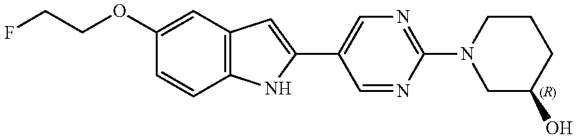 | 2.3 |
| 32 | 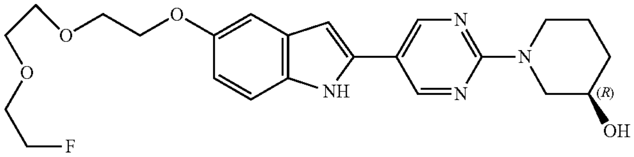 | 2.2 |
| 33 | 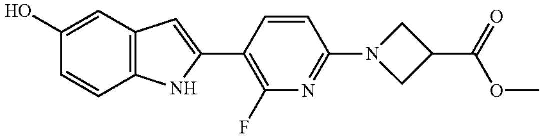 [SMILES: COC(=O)C1CN(c2ccc(-c3cc4cc(O)ccc4[nH]3)c(F)n2)C1] | 3.0 |
n.d = not determined.

Biological Testing

Example (a): Biological Assay Methods and Results $^3$H-THK5117 Competition Binding to Tau Fibrils In Vitro Preparation of recombinant 0N4R Tau fibrils was performed as previously described in Morozova, O. A., Biochemistry (2013), Vol., 52(40), pages 6960-6967. Competition binding experiments to 0N4R Tau fibrils were performed by incubating increasing concentrations [$10^{-10}$-$10^{-6}$ M] of the Example compounds of the invention, or the known tau specific ligand PBB3 (PBB3 was synthesized as previously described in M. Maruyama, et al, Neuron 2013, 79, 1094-1108) or MK6240 (Novandi Chemistry AB), in the presence of 3 nM of the known tau ligand [$^3$H]-THK5117 (Novandi Chemistry) and 0.2 mM 0N4R tau fibrils in binding buffer (50 mM Tris-HCl, pH 7.4, 0.1% BSA) for 1 h in the dark, and at 22° C. The incubation was terminated by filtration through a Whatman GF/B glass filter (Whatman International, Kent, UK) using a Brandel cell harvester. The filter was then washed rapidly four times with 3 mL of ice-cold wash buffer (5 mM Tris-HCl, 0.25 mM NaCl, 5% EtOH), and equilibrated for 1 h in scintillation vials containing 5 mL of Ultima Gold scintillation fluid before being analysed using a Liquid Scintillation Analyzer.

The results are shown in Table 2 in the column labeled "Tau $IC_{50}$". For compounds that were run in the competition binding experiment more than once, the Tau $IC_{50}$ value in Table 2 is the average of the results of each experiment.

$^3$H-AZD2184 Competition Binding to Aβ(1-42) Fibrils In Vitro

Competition binding experiments to Aβ(1-42) amyloid fibrils were performed as previously described in Jureus, A., et al, Journal of Neurochemistry (2010), Vol. 114, pages 784-794 for the Example compounds of the invention indicated in Table 2, or the known tau specific ligand PBB3 (PBB3 was synthesized as previously described in M. Maruyama, et al, Neuron 2013, 79, 1094-1108).

The results are shown in Table 2 in the column labeled "Aβ $IC_{50}$". For compounds that were run in the competition binding experiment more than once, the Aβ $IC_{50}$ value in Table 2 is the average of the results of each experiment.

Relative Selectivity for Tau vs. Aβ

Relative selectivity for tau compared to Aβ for the exemplified compounds was calculated using the results for the [$^3$H]-THK5117 tau and [$^3$H]-AZD2184 Aβ assays described above. The calculated results are shown in Table 2 in the column labeled "Selectivity for tau relative to Aβ".

Biological Assay Results

TABLE 2

| Example Compound No. | Tau $IC_{50}$ (nM) | Aβ $IC_{50}$ (nM) | Selectivity for tau relative to Aβ |
|---|---|---|---|
| 1 | 4 | 8 | 2 |
| 2 | 18 | 22 | 1.2 |
| 3 | 11 | 11 | 1 |
| 4 | 38 | 47 | 1.2 |
| 5 | 7 | 11 | 1.6 |
| 6 | 1 | 37 | 37 |
| 7 | 9 | 80 | 8.9 |
| 8 | 16 | n.d | — |
| 11 | 11 | n.d | — |
| 12 | 40 | n.d | — |
| 14 | 9 | 65 | 7.2 |
| 18 | 29 | n.d | — |
| 21 | 40 | 9 | 0.2 |
| 22 | 3 | 3 | 1 |
| 23 | 6 | n.d | — |
| 24 | 9 | n.d | — |
| 25 | 62 | n.d | — |
| 26 | 48 | n.d | — |
| 27 | 25 | 32 | 1.3 |
| 28 | 4 | 8 | 2 |
| 29 | 14 | 80 | 5.7 |
| 30 | 150 | 90 | 0.6 |
| 31 | 10 | 12 | 1.2 |
| 32 | 89 | 25 | 0.3 |
| 33 | 6 | n.d | — |
| PBB3 | 7 | 28 | 4 |
| MK-6420 | >1000 (inactive) | | |

n.d = not determined.

The results in Table 2 show that the Example compounds of the invention have high affinity binding to recombinant 4R tau fibrils. The results in Table 2 also show that of the Example compounds of the invention tested in the Aβ(1-42) amyloid fibrils competition binding assay, the majority of the compounds of the invention showed higher binding affinity to recombinant 4R tau fibrils compared to Aβ(1-42) amyloid fibrils. The results in Table 2 further show that several examples compounds of the invention have a higher affinity binding to recombinant 4R tau fibrils than the known tau ligand PBB13; and/or have better selectively to recombinant 4R tau fibrils compared to Aβ(1-42) amyloid fibrils than PBB3. The results in Table 2 also show that the example compounds of the invention do not share the same tau binding site as MK-6240, which was inactive in the recombinant 4R tau fibrils assay.

Further aspects of the invention are defined in the following numbered clauses:

§ 1. A compound of formula (I), or a pharmaceutically acceptable salt, ester, amide or carbamate thereof, or a salt of such an ester, amide or carbamate,

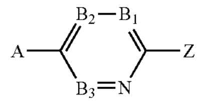

(I)

wherein

A is

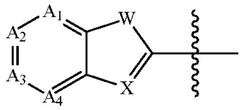

, and $A_1$ and $A_4$ are independently selected from the group consisting of N and CH;

$A_2$ is selected from the group consisting of N, $CR^2$ and CH, and $A_3$ is selected from the group consisting of N and CH, wherein at least two of $A_1$, $A_2$, $A_3$, and $A_4$ are CH, or wherein $A_2$ is $CR^2$ and at least one of $A_1$, $A_3$ and $A_4$ is CH; or $A_2$ is selected from the group consisting of N and CH, and $A_3$ is selected from the group consisting of N, $CR^2$ and CH, wherein at least two of $A_1$, $A_2$, $A_3$, and $A_4$ are CH, or wherein $A_3$ is $CR^2$ and at least one of $A_1$, $A_2$ and $A_4$ is CH;

W is selected from the group consisting of O, S and NH;

X is selected from the group consisting of N and CH;

or A is

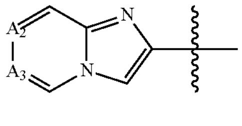, and $A_2$ is selected from the group consisting of N, $CR^2$ and CH and $A_3$ is selected from the group consisting of N and CH, or $A_2$ is selected from the group consisting of N and CH and $A_3$ is selected from the group consisting of N, $CR^2$ and CH;

$B_1$, $B_2$, and $B_3$, are each independently selected from the group consisting of N, CH and $CR^3$, wherein at least one of $B_1$, $B_2$, and $B_3$ is CH or $CR^3$;

Z is selected from the group consisting of

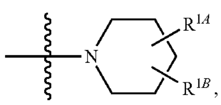
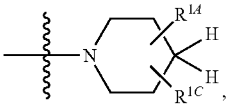,
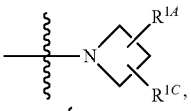
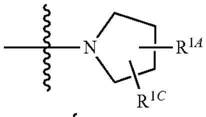,
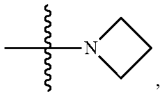, and
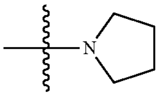

when present $R^{1A}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present $R^{1B}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present $R^{1C}$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O—C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C(O)$C_{1-6}$alkyl optionally substituted with 1, 2 or 3 halogen; —$(CH_2CH_2O)_p$—$R^e$; —$(CH_2CH_2O)_p$—$CH_2CH_2R^f$; and —$(OCH_2CH_2)_p$—$R^f$;

when present each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; $C_{2-6}$alkenyl; $C_{2-6}$alkynyl; C(O)$C_{1-6}$alkyl optionally substituted with 1, 2 or 3 halogen; C(O)—O—$C_{1-6}$alkyl optionally substituted with 1, 2 or 3 halogen; —O—Si($C_{1-6}$alkyl)$_3$ optionally substituted with 1, 2 or 3 halogen; $C_{1-6}$alkylS—; $C_{1-6}$alkylS(=O)—; $C_{1-6}$alkylS($O_2$)—; $NO_2$; —N($R^a$)$_2$; —$C_{1-6}$alkylN($R^a$)$_2$; —N($R^a$)C(O)H;

—N($R^a$)C(O)$C_{1-6}$alkyl optionally substituted with 1, 2 or 3 halogen; C(O)N($R^g$)$_2$; and —$C_{1-6}$alkylC(O)N($R^g$)$_2$;

when present $R^3$ is selected from the group consisting of halogen; OH; $C_{1-6}$alkyl optionally substituted with 1, 2 or 3 halogen (preferably 1, 2 or 3 fluorine); and —$OC_{1-6}$alkyl optionally substituted with 1, 2 or 3 halogen (preferably 1, 2 or 3 fluorine);

when present $R^a$, $R^b$, $R^c$ and $R^d$ are each independently selected from the group consisting of H and $C_{1-6}$alkyl optionally substituted with 1, 2 or 3 halogen;

when present $R^e$ is selected from the group consisting of H and $C_{1-6}$alkyl optionally substituted with 1, 2 or 3 halogens;

when present $R^f$ is selected from the group consisting of H; halogen; —$CH_2$(halogen), —CH(halogen)$_2$, —C(halogen)$_3$, and OH;

when present each $R^g$ is independently selected from the group consisting of H; $C_{1-6}$alkyl; $C_{1-6}$alkyl substituted with 1, 2 or 3 halogen; $C_{1-6}$alkyl substituted with 1, 2 or 3 OH groups; $C_{1-6}$alkyl substituted with 1, 2 or 3 —$OC_{1-3}$alkyl groups; $C_{1-6}$alkyl substituted with a —$OS(O)_2CH_3$ group; and $C_{1-6}$alkyl substituted with a —$S(O)_2OCH_3$ group; and p is 2, 3, 4, 5, 6, 7 or 8.

§ 2. A compound as defined in clause 1, wherein Z is selected from the group consisting of

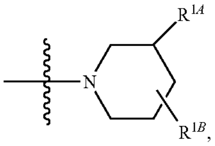
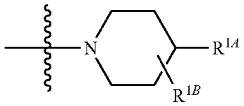
,
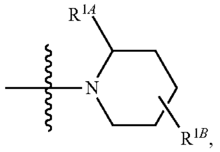
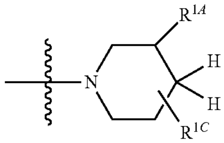
,
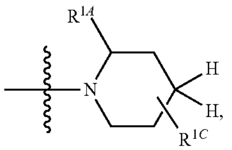
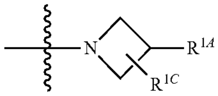
,
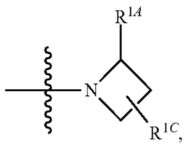
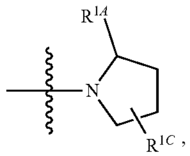
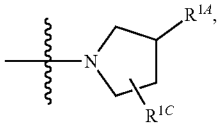
, and
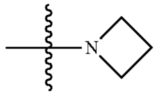
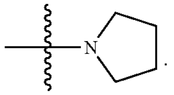
.

§ 3. A compound as defined in clause 1, wherein Z is selected from the group consisting of

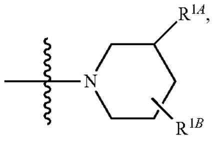
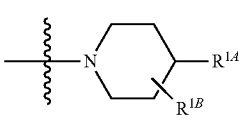
,
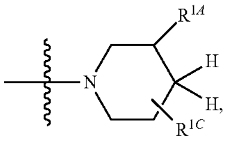
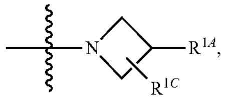
and
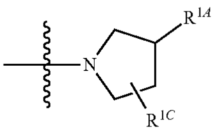
.

§ 4. A compound as defined in clause 1, wherein Z is selected from the group consisting of

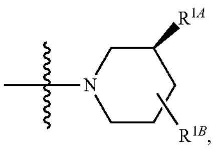
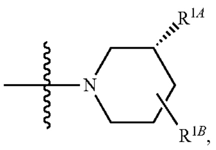
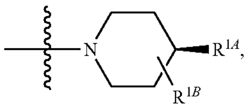
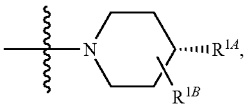
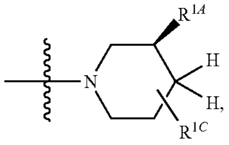
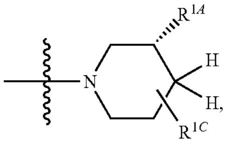
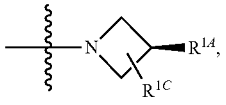
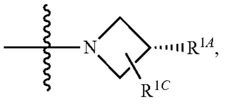
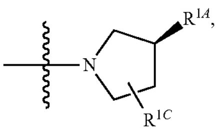
and
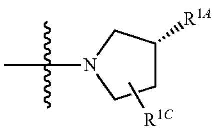

(for example Z is selected from the group consisting of

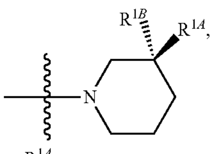
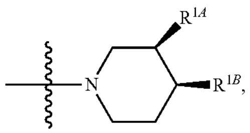
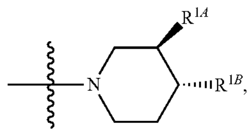

-continued

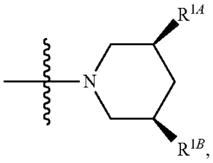
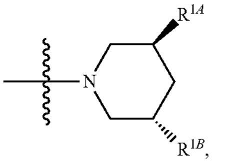
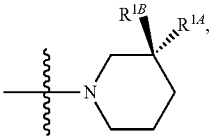
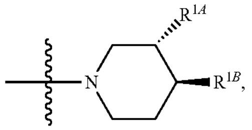
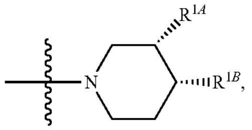
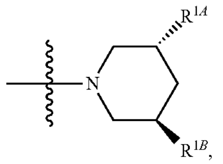
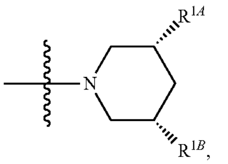
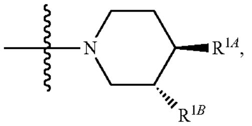
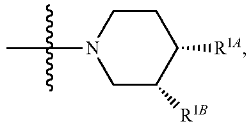
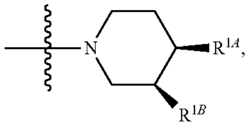
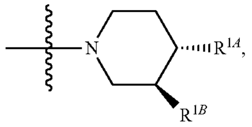
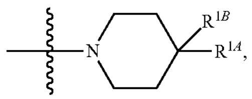
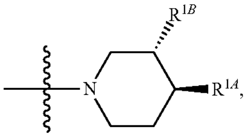
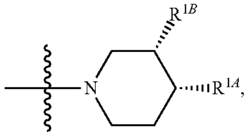
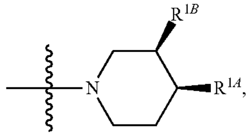
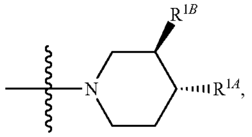
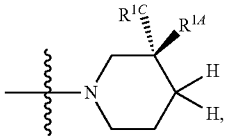
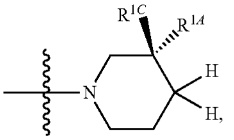
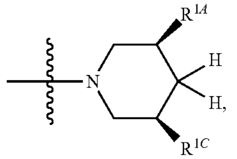
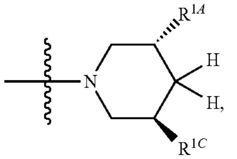
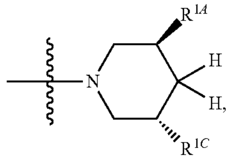
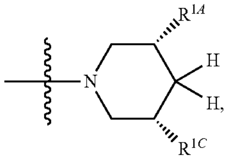

-continued

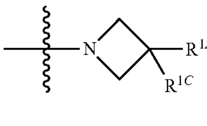
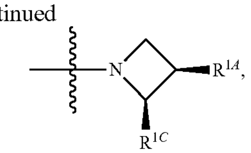
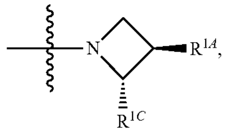
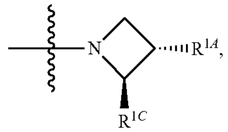
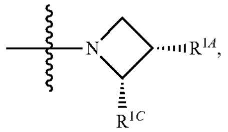
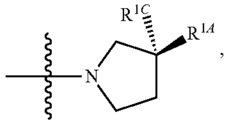
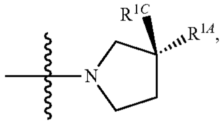
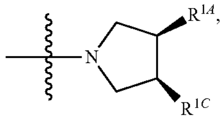
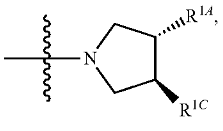
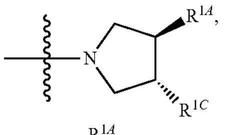 and
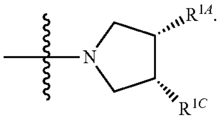

§ 5. A compound as defined in any preceding clause, wherein when present $R^{1A}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)$ $C_{1-6}$alkyl optionally substituted with 1, 2 or 3 halogen; —$C_{1-6}$alkyl-C(O)—$N(R^d)_2$; C(O)—O—$C_{1-6}$alkyl optionally substituted with 1, 2 or 3 halogen; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$;

when present $R^{1B}$ is selected from the group consisting of halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; C(O)—O—$C_{1-6}$alkyl optionally substituted with 1, 2 or 3 halogen; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$; and when present $R^{1C}$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—$S(O)_2$—$C_{1-3}$alkyl optionally substituted with 1, 2 or 3 halogen or OH groups; —$C_{1-6}$alkyl-$S(O)_2$—O—$C_{1-3}$alkyl optionally substituted with 1, 2 or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2 or 3 halogen; —C(O)—$N(R^d)_2$; $N(R^d)C(O)H$; $N(R^d)C(O)C_{1-6}$alkyl optionally substituted with 1, 2 or 3 halogen; —$C_{1-6}$alkyl-C(O)—$N(R^d)_2$; C(O)—O—$C_{1-6}$alkyl optionally substituted with 1, 2 or 3 halogen; —O—$C_{1-6}$alkyl-C(O)—$N(R^d)_2$; —$(CH_2CH_2O)_p$—$R^e$; —$(CH_2CH_2O)_p$—$CH_2CH_2R^f$; and —$(OCH_2CH_2)_p$—$R^f$;

§ 6. A compound as defined in any preceding clause, wherein when present $R^{1A}$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—$N(R^d)_2$; and C(O)—O—$C_{1-6}$alkyl optionally substituted with 1 halogen (preferably F);

when present $R^{1B}$ is selected from the group consisting of OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—$N(R^d)_2$; and C(O)—O—$C_{1-6}$alkyl optionally substituted with 1 halogen (preferably F); and when present $R^{1C}$ is selected from the group consisting of hydrogen; OH; —$C_{1-6}$alkyl optionally substituted with 1 halogen (preferably F) or OH group; —$C_{1-6}$alkyl-O—$S(O)_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-$S(O)_2$—O-phenyl wherein said phenyl is optionally substituted with 1 $C_{1-3}$alkyl group and said $C_{1-3}$alkyl is optionally substituted with 1 halogen (preferably F); C(O)—$N(R^d)_2$; and C(O)—O—$C_{1-6}$alkyl optionally substituted with 1 halogen (preferably F).

§ 7. A compound as defined in any preceding clause, wherein when present $R^{1A}$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and preferably wherein $R^{1A}$ is selected from the group consisting of OH; $C_{1-6}$alkyl optionally substituted with 1 OH group; C(O)—$N(H)_2$; and C(O)—O—$C_{1-6}$alkyl;

when present $R^{1B}$ is selected from the group consisting of —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and preferably wherein $R^{1B}$ is selected from the group consisting of OH; $C_{1-6}$alkyl optionally substituted with 1 OH group; C(O)—$N(H)_2$; and C(O)—O—$C_{1-6}$alkyl; and when present $R^{1C}$ is selected from the group consisting of hydrogen; —$C_{1-6}$alkyl optionally substituted with 1 halogen (preferably F) or OH group; C(O)—$N(R^d)_2$ (preferably wherein each $R^d$ is H); and C(O)—O—$C_{1-6}$alkyl optionally substituted with 1 halogen (preferably F); and preferably wherein $R^{1C}$ is selected from the group consisting of hydrogen; OH; $C_{1-6}$alkyl optionally substituted with 1 OH group; C(O)—$N(H)_2$; and C(O)—O—$C_{1-6}$alkyl § 8. A compound as defined in any one of clauses 1 to 7, wherein when present $R^{1A}$ is OH; —$C_{1-3}$alkyl optionally substituted with 1, 2 or 3 (preferably 1) halogen (preferably F) or OH groups; C(O)—$N(H)_2$ or C(O)—O—$C_{1-3}$alkyl (preferably OH; or —$C_{1-3}$alkyl optionally substituted with 1, 2 or 3 (preferably 1) halogen (preferably F) or OH groups);

when present $R^{1B}$ is OH; —$C_{1-3}$alkyl optionally substituted with 1, 2 or 3 (preferably 1) halogen (preferably F) or OH groups; C(O)—$N(H)_2$ or C(O)—O—$C_{1-3}$alky (hydrogen; OH; or —$C_{1-3}$alkyl optionally substituted with 1, 2 or 3 (preferably 1) halogen (preferably F) or OH groups); and when present $R^{1C}$ is hydrogen; OH; —$C_{1-3}$alkyl optionally substituted with 1, 2 or 3 (preferably 1) halogen (preferably F) or OH groups; C(O)—$N(H)_2$ or C(O)—O—$C_{1-3}$alkyl (preferably hydrogen; OH; or —$C_{1-3}$alkyl optionally substituted with 1, 2 or 3 (preferably 1) halogen (preferably F) or OH groups).

§ 9. A compound as defined in any preceding clause, wherein when Z is

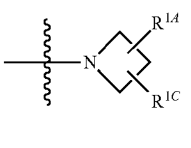 or 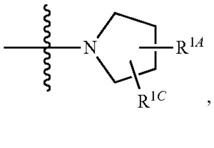 , $R^{1C}$ is hydrogen.

§ 10. A compound as defined in any preceding clause, wherein Z is

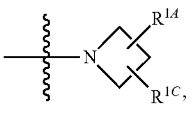 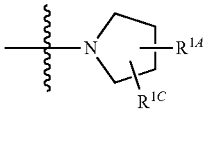 or

-continued

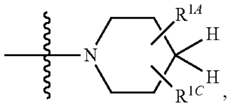, and $R^{1C}$ is hydrogen (i.e. Z is

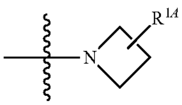, 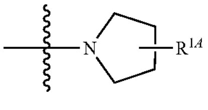 or

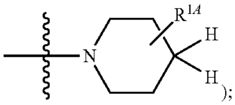);

and preferably wherein Z is:

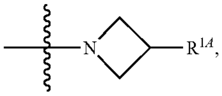, 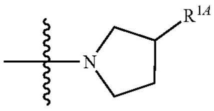 or

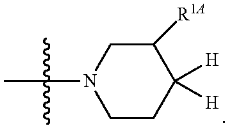.

§ 11. A compound as defined in any preceding clause, wherein when present $R^3$ is selected from the group consisting of halogen and —$OC_{1-6}$alkyl optionally substituted with 1 halogen (preferably fluorine); and preferably when present $R^3$ is fluorine.

§ 12. A compound as defined in any preceding clause, wherein A is

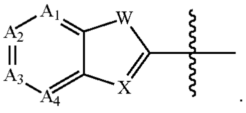.

§ 13. A compound as defined in any preceding clause, wherein W is S or NH; and X is N or CH (and preferably wherein W is S and X is N; or W is NH and X is CH).

§ 14. A compound as defined in any one of clauses 1 to 12, wherein W is S and X is N or CH; or W is NH and X is CH; or W is O and X is CH or N (and preferably wherein W is S and X is N or CH; or W is NH and X is CH; or W is O and X is CH).

§ 15. A compound as defined in any preceding clause, wherein W is NH and X is CH.

§ 16. A compound as defined in any preceding clause, wherein $A_1$ and $A_4$ are CH, or wherein $A_1$ is N and $A_4$ is CH.

§ 17. A compound as defined in any preceding clause, wherein $A_1$ and $A_4$ are CH.

§ 18. A compound as defined in any preceding clause, wherein $A_3$ is selected from the group consisting of N and CH, and at least three of $A_1$, $A_2$, $A_3$ and $A_4$ are CH (and preferably wherein $A_1$, $A_2$, and $A_4$ are CH, and $A_3$ is N or CH).

§ 19. A compound as defined in any preceding clause, wherein the compound is a compound of formula (Ia)

(Ia)

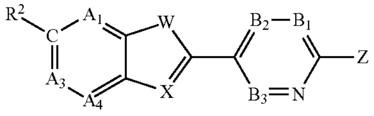

wherein $A_1$, $A_3$, and $A_4$ are independently selected from the group consisting of N and CH, and at least one of $A_1$, $A_3$, and $A_4$ is CH (and preferably wherein each of $A_1$ and $A_4$ is CH, and $A_3$ is N or CH; and more preferably wherein each of $A_1$, $A_3$, and $A_4$ is CH; or preferably wherein $A_1$ is N, $A_4$ is CH, and $A_3$ is N or CH; and more preferably wherein $A_1$ is N, $A_4$ is CH, $A_3$ is N).

§ 20. A compound as defined in any one of clauses 1 to 18, wherein the compound is a compound of formula (Ib)

(Ib)

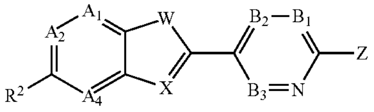

wherein $A_1$, $A_2$, and $A_4$ are independently selected from the group consisting of N and CH, and at least one of $A_1$, $A_2$, and $A_4$ is CH (and preferably wherein each of $A_1$ and $A_4$ is CH, and $A_2$ is N or CH; and more preferably where each of $A_1$, $A_2$, and $A_4$ is CH).

§ 21. A compound as defined in any preceding clause, wherein at least two of $B_1$, $B_2$, and $B_3$ are selected from the group consisting of CH and $CR^3$ (for example, two of $B_1$, $B_2$, and $B_3$ are CH).

§ 22. A compound as defined in any preceding clause, wherein at least one of $B_1$, $B_2$, and $B_3$ is CH, and at least one of $B_1$, $B_2$, and $B_3$ is $CR^3$ and CH.

§ 23. A compound as defined in any preceding clause, wherein two of $B_1$, $B_2$, and $B_3$ are CH, and the other $B_1$, $B_2$, or $B_3$ group is selected from the group consisting of N and $CR^3$.

§ 24. A compound as defined in any preceding clause, wherein $B_2$ and $B_3$ are independently selected from the group consisting of $CR^3$ and CH, and $B_1$ is selected from the group consisting of N, $CR^3$ and CH (and preferably $B_1$ is selected from the group consisting of N and CH).

§ 25. A compound as defined in any preceding clause, wherein $B_1$ and $B_2$ are selected from the group consisting of N and CH, and $B_3$ is selected from the group consisting of N, CH and $CR^3$ (and preferably $B_3$ is selected from the group consisting of CH and $CR^3$).

§ 26. A compound as defined in any preceding clause, wherein $B_1$ or $B_3$ is $CR^3$ (preferably $B_1$ or $B_3$ is CF).

§ 27. A compound as defined in any preceding clause, wherein $B_1$ and $B_2$ are CH and $B_3$ is CH or $CR^3$; and preferably $B_1$ and $B_2$ are CH and $B_3$ is $CR^3$; $B_1$ is N, $B_2$ is CH, and $B_3$ is CH or $CR^3$; and preferably $B_1$ is N, $B_2$ is CH, and $B_3$ is CH.

§ 28. A compound as defined in any preceding clause, wherein when present each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; —N($R^a$)C(O)H; —N($R^a$)C(O) $C_{1-6}$alkyl optionally substituted with 1, 2 or 3 halogen; C(O)N($R^g$)$_2$; and —$C_{1-6}$alkylC(O)N($R^g$)$_2$ (and more preferably when present each $R^2$ is independently selected from the group consisting of halogen; OH; CN; $C_{1-6}$alkyl optionally substituted with 1, 2 or 3 halogen or OH groups; O—$C_{1-6}$alkyl optionally substituted with 1, 2 or 3 halogen or OH groups; C(O)$C_{1-6}$alkyl optionally substituted with 1, 2 or 3 halogen; C(O)—O—$C_{1-6}$alkyl optionally substituted with 1, 2 or 3 halogen; and C(O)N($R^g$)$_2$).

§ 29. A compound as defined in any preceding clause, wherein when present $R^2$ is independently selected from the group consisting of OH and O—$C_{1-6}$alkyl optionally substituted with 1, 2 or 3 halogen (for example fluorine) or OH groups (and more preferably wherein when present $R^2$ is independently selected from the group consisting of OH and 0-$C_{1-3}$alkyl optionally substituted with 1 halogen (for example fluorine) or OH group).

§ 30. A compound of formula (X), or a pharmaceutically acceptable salt, ester, amide or carbamate thereof, or a salt of such an ester, amide or carbamate, (X)

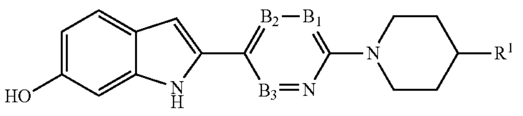

wherein $B_1$, $B_2$, and $B_3$, are each independently selected from the group consisting of N, CH and $CR^3$, wherein at least one of $B_1$, $B_2$, and $B_3$ is CH or $CR^3$;

$R^1$ is selected from the group consisting of hydrogen; halogen; —OH; —CN; —$C_{1-6}$alkyl optionally substituted with 1, 2 or 3 halogen or OH groups; —O —$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—S(O)$_2$—$C_{1-3}$alkyl optionally substituted with 1, 2 or 3 halogen or OH groups; —$C_{1-6}$alkyl-S(O)$_2$—O—$C_{1-3}$alkyl optionally substituted with 1, 2 or 3 halogen or OH groups; —$C_{1-6}$alkyl-O—S(O)$_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-S(O)$_2$—O-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2 or 3 halogen; —O —C(O)$C_{1-6}$alkyl optionally substituted with 1, 2 or 3 halogen; —$C_{1-6}$alkyl-C(O)—O—$C_{1-6}$alkyl optionally substituted with 1, 2 or 3 halogen; —$C_{1-6}$alkyl-O—C (O)$C_{1-6}$alkyl optionally substituted with 1, 2 or 3 halogen; —($CH_2CH_2O$)$_p$—$R^e$; —($CH_2CH_2O$)$_p$—$CH_2CH_2R^f$; and —($OCH_2CH_2$)$_p$—$R^f$;

when present $R^3$ is selected from the group consisting of halogen; OH; $C_{1-6}$alkyl optionally substituted with 1, 2 or 3 halogen (preferably 1, 2 or 3 fluorine); and —O$C_{1-6}$alkyl optionally substituted with 1, 2 or 3 halogen (preferably 1, 2 or 3 fluorine);

when present $R^b$, $R^c$ and $R^d$ are each independently selected from the group consisting of H and $C_{1-6}$alkyl optionally substituted with 1, 2 or 3 halogen;

when present $R^e$ is selected from the group consisting of H and $C_{1-6}$alkyl optionally substituted with 1, 2 or 3 halogens;

when present $R^f$ is selected from the group consisting of H; halogen; —$CH_2$(halogen), —CH(halogen)$_2$, —C(halogen)$_3$, and OH; and p is 2, 3, 4, 5, 6, 7 or 8.

§ 31. A compound as defined in clause 30, wherein $R^1$ is selected from the group consisting of hydrogen; halogen; —OH; —CN; —$C_{1-6}$alkyl optionally substituted with 1, 2 or 3 halogen or OH groups; —O—$C_{1-6}$alkyl optionally substituted with 1, 2 or 3 halogen or OH groups; —$C_{1-3}$alkyl-O—$C_{1-6}$alkyl optionally substituted with 1, 2 or 3 halogen or OH groups; —$C_{1-6}$alkyl-O—S(O)$_2$—$C_{1-3}$alkyl optionally substituted with 1, 2 or 3 halogen or OH groups; —$C_{1-6}$alkyl-S(O)$_2$—O—$C_{1-3}$alkyl optionally substituted with 1, 2 or 3 halogen or OH groups; —$C_{1-6}$alkyl-O—S(O)$_2$-phenyl wherein said phenyl is optionally substituted with 1 $C_{1-3}$alkyl group and said $C_{1-3}$alkyl is optionally substituted with 1, 2 or 3 halogen; —$C_{1-6}$alkyl-S(O)$_2$—O-phenyl wherein said phenyl is optionally substituted with 1 $C_{1-3}$alkyl group and said $C_{1-3}$alkyl is optionally substituted with 1, 2 or 3 halogen; —C(O)—N($R^d$)$_2$; N($R^d$)C(O)H; N($R^d$)C(O)$C_{1-6}$alkyl optionally substituted with 1, 2 or 3 halogen; —$C_{1-6}$alkyl-C(O) —N($R^d$)$_2$; C(O)—O—$C_{1-6}$alkyl optionally substituted with 1, 2 or 3 halogen; —O—$C_{1-6}$alkyl-C(O)—N($R^d$)$_2$; —($CH_2CH_2O$)$_p$—$R^e$; —($CH_2CH_2O$)$_p$—$CH_2CH_2R^f$; and —($OCH_2CH_2$)$_p$—$R^f$.

§ 32. A compound as defined in any one of clauses 30 or 31, wherein $R^1$ is selected from the group consisting of —$C_{1-6}$alkyl optionally substituted with 1 halogen (preferably F) or OH group; —$C_{1-6}$alkyl-O—S(O)$_2$-phenyl wherein said phenyl is optionally substituted with 1 $C_{1-3}$alkyl group and said $C_{1-3}$alkyl is optionally substituted with 1 halogen (preferably F); —$C_{1-6}$alkyl-S(O)$_2$—O-phenyl wherein said phenyl is optionally substituted with 1 $C_{1-3}$alkyl group and said $C_{1-3}$alkyl is optionally substituted with 1 halogen (preferably F); C(O)—N($R^d$)$_2$; and C(O)—O—$C_{1-6}$alkyl optionally substituted with 1 halogen (preferably F).

§ 33. A compound as defined in any one of clauses 30 to 32, wherein $R^1$ is selected from the group consisting of —$C_{1-6}$alkyl optionally substituted with 1 halogen (preferably F) or OH group; C(O)—N($R^d$)$_2$ (preferably wherein each $R^d$ is H); and C(O)—O—$C_{1-6}$alkyl optionally substituted with 1 halogen (preferably F); and preferably wherein $R^1$ is selected from the group consisting of $C_{1-6}$alkyl optionally substituted with 1 OH group; C(O)—N(H)$_2$; and C(O)—O—$C_1$-6alkyl.

§ 34. A compound as defined in any one of clauses 30 to 33, wherein $R^1$ $CH_2OH$.

§ 35. A compound as defined in any one of clauses 30 to 33, wherein $R^1$ is —$C_{1-3}$alkyl optionally substituted with 1, 2 or 3 (preferably 1) halogen (preferably F) or OH groups; C(O)—$N(H)_2$ or C(O)—O—$C_{1-3}$alkyl.

§ 36. A compound as defined in any one of clauses 30 to 35, wherein when present $R^3$ is selected from the group consisting of halogen and —$OC_{1-6}$alkyl optionally substituted with 1 halogen (preferably fluorine); and preferably when present $R^3$ is fluorine.

§ 37. A compound as defined in any one of clauses 30 to 36, wherein at least two of $B_1$, $B_2$, and $B_3$ are selected from the group consisting of CH and $CR^3$ (for example, two of $B_1$, $B_2$, and $B_3$ are CH).

§ 38. A compound as defined in any one of clauses 30 to 37, wherein at least one of $B_1$, $B_2$, and $B_3$ is CH, and at least one of $B_1$, $B_2$, and $B_3$ is $CR^3$ and CH.

§ 39. A compound as defined in any one of clauses 30 to 38, wherein two of $B_1$, $B_2$, and $B_3$ are CH, and the other $B_1$, $B_2$, or $B_3$ group is selected from the group consisting of N and $CR^3$.

§ 40. A compound as defined in any one of clauses 30 to 39, wherein $B_2$ and $B_3$ are independently selected from the group consisting of $CR^3$ and CH, and $B_1$ is selected from the group consisting of N, $CR^3$ and CH (and preferably $B_1$ is selected from the group consisting of N and CH).

§ 41. A compound as defined in any one of clauses 30 to 40, wherein $B_1$ and $B_2$ are selected from the group consisting of N and CH, and $B_3$ is selected from the group consisting of N, CH and $CR^3$ (and preferably $B_3$ is selected from the group consisting of CH and $CR^3$).

§ 42. A compound as defined in any one of clauses 30 to 41, wherein $B_1$ or $B_3$ is $CR^3$ (preferably $B_1$ or $B_3$ is CF).

§ 43. A compound as defined in any one of clauses 30 to 42, wherein $B_1$ and $B_2$ are CH and $B_3$ is CH or $CR^3$; and preferably $B_1$ and $B_2$ are CH and $B_3$ is $CR^3$; $B_1$ is N, $B_2$ is CH, and $B_3$ is CH or $CR^3$; and preferably $B_1$ is N, $B_2$ is CH, and $B_3$ is CH.

§ 44. A compound as defined in any preceding clause, wherein the compound comprises one or more radioisotopes.

§ 45. A compound as defined in any preceding clause, wherein the compound comprises one or more radioisotopes at the $R^1$, $R^2$, $R^3$ and/or $R^e$ position.

§ 46. A compound as defined in any preceding clause, wherein the compound comprises one or more radioisotopes, wherein the one or more radioisotopes is independently selected from the group consisting of $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^3H$, $^{11}C$, $^{14}C$, $^{13}N$, $^{15}O$, $^{18}F$, $^{19}F$, $^{120}I$, $^{123}I$ and $^{125}I$, more preferably $^3H$, $^{11}C$, $^{13}N$, $^{15}O$, $^{18}F$, $^{120}I$, $1^{123}$, and $^{125}I$, even more preferably $^{11}C$, $^{13}N$, $^{15}O$, and $^{18}F$, and most preferably $^{18}F$ and $^{11}C$.]

§ 47. A compound as defined in clause 1, wherein the compound is selected from the group consisting of:

1-[5-(6-Methoxy-1,3-benzothiazol-2-yl)pyridin-2-yl]piperidin-3-ol;

(3R)-1-[5-(6-Methoxy-1,3-benzothiazol-2-yl)pyridin-2-yl]pyrrolidin-3-ol);

(3S)-1-[5-(6-Methoxy-1,3-benzothiazol-2-yl)pyridin-2-yl]pyrrolidin-3-ol);

2-{2-Fluoro-6-[3-(hydroxymethyl)azetidin-1-yl]pyridin-3-yl}-1H-indol-5-ol;

2-{2-Fluoro-6-[3-(hydroxyethyl)azetidin-1-yl]pyridin-3-yl}-1H-indol-5-ol;

2-{2-Fluoro-6-[(3R)-3-hydroxypiperidin-1-yl]pyridin-3-yl}-1H-indol-5-ol;

2-{2-Fluoro-6-[(3S)-3-hydroxypiperidin-1-yl]pyridin-3-yl}-1H-indol-5-ol;

(3R,4R)-1-[5-(6-Methoxy-1,3-benzothiazol-2-yl)pyridin-2-yl]piperidine-3,4-diol;

(3R,4S)-1-[5-(6-Methoxy-1,3-benzothiazol-2-yl)pyridin-2-yl]piperidine-3,4-diol;

(3S,4R)-4-(Hydroxymethyl)-1-[5-(6-methoxy-1,3-benzothiazol-2-yl)pyridin-2-yl]piperidin-3-ol;

(3S,4S)-4-(Hydroxymethyl)-1-[5-(6-methoxy-1,3-benzothiazol-2-yl)pyridin-2-yl]piperidin-3-ol;

(3R,5S)-1-[5-(6-Methoxy-1,3-benzothiazol-2-yl)pyridin-2-yl]piperidine-3,5-diol;

(3S,5S)-1-[5-(6-Methoxy-1,3-benzothiazol-2-yl)pyridin-2-yl]piperidine-3,5-diol;

4-(Hydroxymethyl)-1-[5-(6-methoxy-1,3-benzothiazol-2-yl)pyridin-2-yl]piperidin-4-ol;

(3R,4R)-1-[6-Fluoro-5-(5-hydroxy-1H-indol-2-yl)pyridin-2-yl]piperidine-3,4-diol;

(3R,4S)-1-[6-Fluoro-5-(5-hydroxy-1H-indol-2-yl)pyridin-2-yl]piperidine-3,4-diol;

2-{2-Fluoro-6-[(3S,4R)-3-hydroxy-4-(hydroxymethyl)piperidin-1-yl]pyridin-3-yl}-1H-indol-5-ol;

2-{2-Fluoro-6-[(3S,4S)-3-hydroxy-4-(hydroxymethyl)piperidin-1-yl]pyridin-3-yl}-1H-indol-5-ol;

(3S,5S)-1-[6-Fluoro-5-(5-hydroxy-1H-indol-2-yl)pyridin-2-yl]piperidine-3,5-diol;

(3R,5S)-1-[6-Fluoro-5-(5-hydroxy-1H-indol-2-yl)pyridin-2-yl]piperidine-3,5-diol; and 2-{2-Fluoro-6-[4-hydroxy-4-(hydroxymethyl)piperidin-1-yl]pyridin-3-yl}-1H-indol-5-ol;

or a pharmaceutically acceptable salt, ester, amide or carbamate thereof, or a salt of such an ester, amide or carbamate; and wherein the compound may optionally comprise one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^3H$, $^{11}C$, $^{14}C$, $^{13}N$, $^{15}O$, $^{18}F$, $^{19}F$, $^{120}I$, $^{123}I$ and $^{125}I$, and more preferably $^3H$, $^{11}C$, $^{13}N$, $^{15}O$, $^{18}F$, $^{120}I$, $I^{123}$, and $^{125}I$, and most preferably $^{18}F$ and $^{11}C$;

or a compound as defined in clause 30, wherein the compound is:

2-{2-Fluoro-6-[4-(hydroxymethyl)piperidin-1-yl]pyridin-3-yl}-1H-indol-6-ol or a pharmaceutically acceptable salt, ester, amide or carbamate thereof, or a salt of such an ester, amide or carbamate; and wherein the compound may optionally comprise one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$, preferably $^3H$, $^{11}C$, $^{14}C$, $^{13}N$, $^{15}O$, $^{18}F$, $^{19}F$, $^{120}I$, $^{123}I$ and $^{125}I$, and more preferably $^3H$, $^{11}C$, $^{13}N$, $^{15}O$, $^{18}F$, $^{120}I$, $I^{123}$, and $^{125}I$, and most preferably $^{18}F$ and $^{11}C$.

§ 48. A pharmaceutical composition comprising a compound of as defined in any one of clauses 1 to 47, together with a pharmaceutically suitable carrier.

§ 49. A composition as defined in clause 48, which also contains an additional active ingredient, for example an additional therapeutic agent or an additional diagnostic agent.

§ 50. A compound as defined in any one of clauses 1 to 47, or a composition as defined in clause 48 or 49, for use as a diagnostic agent, wherein the compound comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

§ 51. Use of a compound as defined in any one of clauses 1 to 47 for the detection of tau deposits.

§ 52. A compound as defined in any one of clauses 1 to 47, or a composition as defined in clause 48 or 49, or a compound or a composition as defined in clause 50, for use as a diagnostic agent in the diagnosis or monitoring of progression of a disease or disorder selected from the group consisting of Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugilistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.Ile383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, and white matter tauopathy with globular glial inclusions.

§ 53. A method of diagnosing a patient or monitoring disease progression in a patient comprising administering a compound as defined in any one of clauses 1 to 47 to the patient, or a composition as defined in clause 48 or 49 to the patient.

§ 54. The method of diagnosing a patient or monitoring disease progression in a patient as defined in clause 53, wherein the compound comprises one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ and $^{131}I$.

§ 55. A method of diagnosing or monitoring of progression as defined in clause 53 or 54, further comprising detecting the compound, for example using positron emission topography.

§ 56. A compound of as defined in any one of clauses 1 to 47, or a composition as defined in clause 48 or 49, for use as a medicament.

§ 57. A compound or a composition as defined in clause 56, for use in the prevention or treatment of a disease or disorder selected from the group consisting Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion—body myositis, chronic traumatic encephalopathy, Down's syndrome, Gerstman-Sträussler-Scheinker syndrome, British dementia, familial Danish dementia, dementia pugilistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.Ile383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Sträussler-Scheinker with tau, mutations in LRRK2, SLC9A6-related mental retardation, and white matter tauopathy with globular glial inclusions.

The invention claimed is:

1. A compound of formula (I):

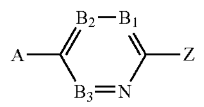

(I)

or a pharmaceutically acceptable salt, ester, ester salt, amide, amide salt, carbamate, or carbamate salt thereof, wherein:

A has formula (IA):

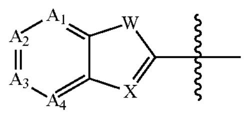

(IA)

where, in formula (IA):

W is NH;

X is CH;

and $A_1$, $A_2$, $A_3$, and $A_4$ are chosen according to (i) or (ii):

(i) $A_1$ and $A_4$ are independently selected from the group consisting of N and CH; $A_2$ is selected from the group consisting of N, $CR^2$, and CH; and $A_3$ is selected from the group consisting of N and CH, provided at least one of (a) or (b) applies:

(a) at least two of $A_1$, $A_2$, $A_3$, or $A_4$ are CH; or (b) $A_2$ is $CR^2$ and at least one of $A_1$, $A_3$, or $A_4$ is CH; or (ii) $A_1$ and $A_4$ are independently selected from the group consisting of N and CH; $A_2$ is selected from the group consisting of N and CH; and $A_3$ is selected from the group consisting of N, $CR^2$ and CH, provided at least one of (a) or (b) applies:

(a) at least two of $A_1$, $A_2$, $A_3$, or $A_4$ are CH; or (b) $A_3$ is $CR^2$ and at least one of $A_1$, $A_2$, or $A_4$ is CH;

or A has formula (IB):

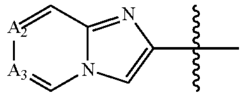

(IB)

where, in formula (IB), either:

(i) $A_2$ is selected from the group consisting of N, $CR^2$, and CH, and $A_3$ is selected from the group consisting of N and CH; or (ii) $A_2$ is selected from the group consisting of N and CH, and $A_3$ is selected from the group consisting of N, $CR^2$, and CH;

$B_1$, $B_2$, and $B_3$, are each independently selected from the group consisting of N, CH, and $CR^3$, wherein at least one of $B_1$, $B_2$, and $B_3$ is CH or $CR^3$;

Z is selected from the group consisting of

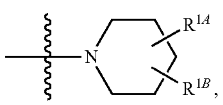
,
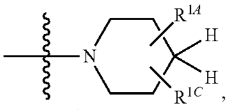
,
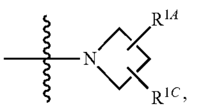
, and
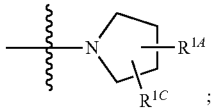
;

$R^{1A}$ is selected from the group consisting of Cl; Br; I; —OH; —CN; —$C_{1-6}$alkyl optionally substituted with 1, 2, or 3 halogen or OH groups; —O—$C_{1-6}$alkyl optionally substituted with 1, 2, or 3 halogen or OH group; —$C_{1-3}$alkyl-O—$C_{1-6}$alkyl optionally substituted with 1, 2, or 3 halogen or OH groups;

—$C_{1-6}$alkyl-O—$S(O)_2$—$C_{1-3}$alkyl optionally substituted with 1, 2, or 3 halogen or OH groups; —$C_{1-6}$alkyl-$S(O)_2$—O—$C_{1-3}$alkyl optionally substituted with 1, 2, or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^d$)C(O)H; N($R^d$)C(O)$C_{1-6}$alkyl optionally substituted with 1, 2, or 3 halogen; —$C_{1-6}$alkyl-C(O)—N($R^d$)$_2$; —O—$C_{1-6}$alkyl-C(O)—N($R^4$)$_2$; —C(O)—O—$C_{1-6}$alkyl optionally substituted with 1, 2, or 3 halogen; —O—C(O)$C_{1-6}$alkyl optionally substituted with 1, 2, or 3 halogen; —$C_{1-6}$alkyl-C(O)—O—$C_{1-6}$alkyl optionally substituted with 1, 2, or 3 halogen; —$C_{1-6}$alkyl-O—C(O)$C_{1-6}$alkyl optionally substituted with 1, 2, or 3 halogen; —$(CH_2CH_2O)_p$—$R^e$; —$(CH_2CH_2O)_p$—$CH_2CH_2R^f$; and —$(OCH_2CH_2)_p$—$R^f$;

$R^{1B}$ is selected from the group consisting of halogen; —OH; —CN; —$C_{1-6}$alkyl optionally substituted with 1, 2, or 3 halogen or OH groups; —O—$C_{1-6}$alkyl optionally substituted with 1, 2, or 3 halogen or OH group; —$C_{1-3}$alkyl-O—$C_{1-6}$alkyl optionally substituted with 1, 2, or 3 halogen;

—$C_{1-6}$alkyl-O—$S(O)_2$—$C_{1-3}$alkyl optionally substituted with 1, 2, or 3 halogen or OH groups; —$C_{1-6}$alkyl-$S(O)_2$—O—$C_{1-3}$alkyl optionally substituted with 1, 2, or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-O—S(halogen)$_2$N($R^b$)$_2$; —N($R^c$)$_2$; —$C_{1-6}$alkylN($R^c$)$_2$; —C(O)—N($R^d$)$_2$; N($R^4$)C(O)H; N($R^4$)C(O)$C_{1-6}$alkyl optionally substituted with 1, 2, or 3 halogen; $C_{1-6}$alkyl-C(O)—N($R^d$)$_2$; —O—$C_{1-6}$alkyl-C(O)—N($R^d$)$_2$; —C(O)—O—$C_{1-6}$alkyl optionally substituted with 1, 2, or 3 halogen; —O—C(O)$C_{1-6}$alkyl optionally substituted with 1, 2, or 3 halogen; —$C_{1-6}$alkyl-C(O)—O—$C_{1-6}$alkyl optionally substituted with 1, 2, or 3 halogen; —$C_{1-6}$alkyl-O—C(O)$C_{1-6}$alkyl optionally substituted with 1, 2, or 3 halogen; —$(CH_2CH_2O)_p$—$R^f$; —$(CH_2CH_2O)_p$—$CH_2CH_2R^f$, and —$(OCH_2CH_2)_p$—$R^f$, $R^{1C}$ is selected from the group consisting of hydrogen; halogen; —OH; —CN; —$C_{1-6}$alkyl optionally substituted with 1, 2, or 3 halogen or OH groups; —O—$C_{1-6}$alkyl optionally substituted with 1, 2, or 3 halogen or OH groups;

—$C_{1-3}$alkyl-O—$C_{1-6}$alkyl optionally substituted with 1, 2, or 3 halogen or OH groups; —$C_{1-6}$alkyl-O—$S(O)_2$—$C_{1-3}$alkyl optionally substituted with 1, 2, or 3 halogen or OH groups; —$C_{1-6}$alkyl-O—$S(O)_2$—$C_{1-3}$alkyl optionally substituted with 1, 2, or 3 halogen or OH groups; —$C_{1-6}$alkyl-O—$S(O)_2$-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-$S(O)_2$—O-phenyl wherein said phenyl is optionally substituted with 1 $C_{1-3}$alkyl group and said $C_{1-3}$alkyl is optionally substituted with 1, 2, or 3 halogen;

—$C_{1-6}$alkyl-O—S(halogen)$_2$N($R^b$)$_2$; —N($R^c$)$_2$; —$C_{1-6}$alkylN($R^c$)$_2$; —C(O)—N($R^4$)$_2$; N($R^d$)C(O)H; N($R^4$)C(O)$C_{1-6}$alkyl optionally substituted with 1, 2, or 3 halogen; —$C_{1-6}$alkyl-C(O)—N($R^d$)$_2$; —C(O)—O—$C_{1-6}$alkyl optionally substituted with 1, 2, or 3 halogen; —O—C(O)$C_{1-6}$alkyl optionally substituted with 1, 2, or 3 halogen; —$C_{1-6}$alkyl-C(O)—O—$C_{1-6}$alkyl optionally substituted with 1, 2, or 3 halogen; —$C_{1-6}$alkyl-O—C(O)$C_{1-6}$alkyl optionally substituted with 1, 2, or 3 halogen; —$(CH_2CH_2O)_p$—$R^e$; —$(CH_2CH_2O)_p$—$CH_2CH_2R^f$; and —$(OCH_2CH_2)_p$—$R^f$, each $R^2$ is independently selected from the group consisting of halogen; OH; CN; $C_{1-6}$alkyl optionally substituted with 1, 2, or 3 halogen or OH groups; O—$C_{1-6}$alkyl optionally substituted with 1, 2, or 3 halogen or OH groups; $C_{2-6}$alkenyl; $C_{2-6}$alkynyl;

$C(O)C_{1-6}$alkyl optionally substituted with 1, 2, or 3 halogen; $C(O)—O—C_{1-6}$alkyl optionally substituted with 1, 2, or 3 halogen; $—O—Si (C_{1-6}alkyl)_3$ optionally substituted with 1, 2, or 3 halogen; $C_{1-6}$alkylS—; $C_{1-6}$alkylS(═O)—; $—C_{1-6}alkylS(O_2)—$; $NO_2$; $—N(R^a)_2$; $—C_{1-6}alkylN(R^a)_2$; $—N(R^a)C(O)H$; $—N(R^a)C(O)C_{1-6}$alkyl optionally substituted with 1, 2, or 3 halogen; $C(O)N(R^g)_2$; $—C_{1-6}alkylC(O)N(R^g)_2$; and $—(OCH_2CH_2)_p—R^f$;

$R^3$ is selected from the group consisting of halogen; OH; $C_{1-6}$alkyl optionally substituted with 1, 2, or 3 halogen; and $—OC_{1-6}$alkyl optionally substituted with 1, 2, or 3 halogen;

$R^a$, $R^b$, $R^c$ and $R^d$ are each independently selected from the group consisting of H and $C_{1-6}$alkyl optionally substituted with 1, 2, or 3 halogen;

$R^e$ is selected from the group consisting of H and $C_{1-6}$alkyl optionally substituted with 1, 2, or 3 halogen;

$R^f$ is selected from the group consisting of H; halogen; $—CH_2$ (halogen); —CH $(halogen)_2$; $—C(halogen)_3$; and OH;

each $R^g$ is independently selected from the group consisting of H; $C_{1-6}$alkyl; $C_{1-6}$alkyl substituted with 1, 2, or 3 halogen; $C_{1-6}$alkyl substituted with 1, 2, or 3 OH groups; $C_{1-6}$alkyl substituted with 1, 2, or 3 $—OC_{1-3}$alkyl groups; $C_{1-6}$alkyl substituted with a $—OS(O)_2CH_3$ group; and $C_{1-6}$alkyl substituted with a $—S(O)_2OCH_3$ group; and p is 2, 3, 4, 5, 6, 7, or 8.

2. The compound of claim 1, wherein Z is selected from the group consisting of:

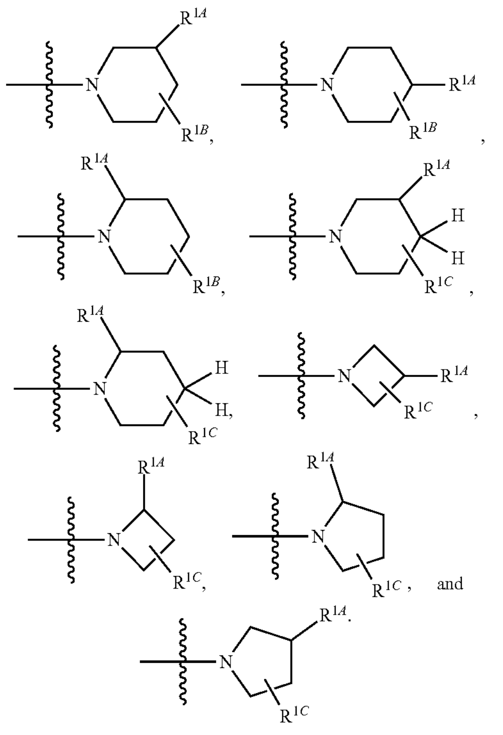

3. The compound of claim 1, wherein Z is selected from the group consisting of:

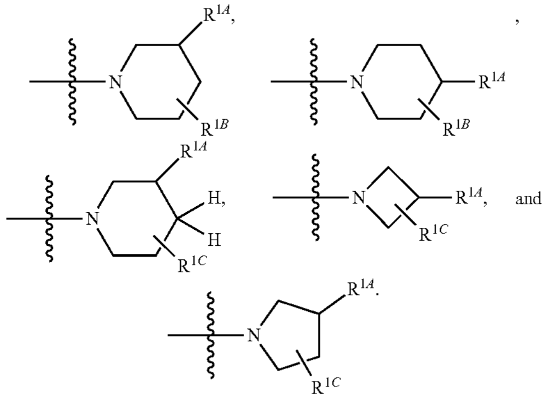

4. The compound of claim 1, wherein:

$R^{1A}$ is selected from the group consisting of Cl; Br; I; —OH; —CN; $—C_{1-6}$alkyl optionally substituted with 1, 2, or 3 halogen or OH groups; $—O—C_{1-6}$alkyl optionally substituted with 1, 2, or 3 halogen or OH groups; $—C_{1-3}alkyl-O—C_{1-6}$alkyl optionally substituted with 1, 2, or 3 halogen or OH groups; $—C_{1-6}alkyl-O—S(O)_2—C_{1-3}$alkyl optionally substituted with 1, 2, or 3 halogen or OH groups; $—C_{1-6}alkyl-O—S(O)_2—O—C_{1-3}$alkyl optionally substituted with 1, 2, or 3 halogen or OH groups; $—C_{1-6}alkyl-O—S(O)_2$-phenyl wherein said phenyl is optionally substituted with 1 $C_{1-3}$alkyl group and said $C_{1-3}$alkyl is optionally substituted with 1, 2, or 3 halogen; $—C_{1-6}alkyl-S(O)_2—O$-phenyl wherein said phenyl is optionally substituted with 1 $C_{1-3}$alkyl group and said $C_{1-3}$alkyl is optionally substituted with 1, 2, or 3 halogen; $—C(O)—N(R^d)_2$; $N(R^4)C(O)H$; $N(R^4)C(O)C_{1-6}$alkyl optionally substituted with 1, 2, or 3 halogen; $—C_{1-6}alkyl-C(O)—N(R^4)_2$; $C(O)—O—C_{1-6}$alkyl optionally substituted with 1, 2, or 3 halogen; $—O—C_{1-6}alkyl-C(O)—N(R^d)_2$; $—(CH_2CH_2O)_p—R^e$; $—(CH_2CH_2O)_p—CH_2CH_2R^f$; and $—(OCH_2CH_2)_p—R^f$;

$R^{1B}$ is selected from the group consisting of halogen; —OH; —CN; $—C_{1-6}$alkyl optionally substituted with 1, 2, or 3 halogen or OH groups; $—O—C_{1-6}$alkyl optionally substituted with 1, 2, or 3 halogen or OH groups; $—C_{1-3}alkyl-O—C_{1-6}$alkyl optionally substituted with 1, 2, or 3 halogen or OH groups; $—C_{1-6}alkyl-O—S(O)_2—O—C_{1-3}$alkyl optionally substituted with 1, 2, or 3 halogen or OH groups; $—C_{1-6}alkyl-S(O)_2—O—C_{1-3}$alkyl optionally substituted with 1, 2, or 3 halogen OH groups; $—C_{1-6}alkyl-O—S(O)_2$-phenyl wherein said phenyl is optionally substituted with 1 $C_{1-3}$alkyl group and said $C_{1-3}$alkyl is optionally substituted with 1, 2, or 3 halogen; $—C_{1-6}alkyl-S(O)_2—O$-phenyl wherein said phenyl is optionally substituted with 1 $C_{1-3}$alkyl group and said $C_{1-3}$alkyl is optionally substituted with 1, 2, or 3 halogen; $—C(O)—N(R^4)_2$; $N(R^d)C(O)H$; $N(R^4)C(O)C_{1-6}$alkyl optionally substituted with 1, 2, or 3 halogen; $—C_{1-6}alkyl-C(O)—N(R^d)_2$; $C(O)—O—C_{1-6}$alkyl optionally substituted with 1, 2, or 3 halogen; $—O—C_{1-6}alkyl-C(O)—N(R^4)_2$;

—$(CH_2CH_2O)_p$—$R^e$; —$(CH_2CH_2O)_p$—$CH_2CH_2R^f$; and —$(OCH_2CH_2)_p$—$R^f$; and $R^{1C}$ is selected from the group consisting of hydrogen; halogen; —OH; —CN; —$C_{1-6}$alkyl optionally substituted with 1, 2, or 3 halogen or OH groups; —O—$C_{1-6}$alkyl optionally substituted with 1, 2, or 3 halogen or OH groups;

—$C_{1-3}$alkyl-O—$C_{1-6}$alkyl optionally substituted with 1, 2, or 3 halogen or OH groups; —$C_{1-6}$alkyl-O—S$(O)_2$—$C_{1-3}$alkyl optionally substituted with 1, 2, or 3 halogen or OH groups; —$C_{1-6}$alkyl-S$(O)_2$—O—$C_{1-3}$alkyl optionally substituted with 1, 2, or 3 halogen or OH groups; —$C_{1-6}$alkyl-O—S$(O)_2$-phenyl wherein said phenyl is optionally substituted with 1 $C_{1-3}$alkyl group and said $C_{1-3}$alkyl is optionally substituted with 1, 2, or 3 halogen; —$C_{1-6}$alkyl-S$(O)_2$—O-phenyl wherein said phenyl is optionally substituted with 1 $C_{1-3}$alkyl group and said $C_{1-3}$alkyl is optionally substituted with 1, 2, or 3 halogen; —C(O)—$N(R^4)_2$; $N(R^4)$C(O)H; $N(R^4)C(O)C_{1-6}$alkyl optionally substituted with 1, 2, or 3 halogen; —$C_{1-6}$alkyl-C(O)—$N(R^4)_2$; C(O)—O—$C_{1-6}$alkyl optionally substituted with 1, 2, or 3 halogen; —O—$C_{1-6}$alkyl-C(O)—$N(R^4)_2$; —$(CH_2CH_2O)_p$—$R^e$; —$(CH_2CH_2O)_p$—$CH_2CH_2R^f$; and —$(OCH_2CH_2)_p$—$R^f$.

5. The compound of claim 1, wherein $R^{1A}$ is selected from the group consisting of OH; —$C_{1-6}$alkyl optionally substituted with 1 halogen or OH group; —$C_{1-6}$alkyl-O—S$(O)_2$-phenyl wherein said phenyl is optionally substituted with 1 $C_{1-3}$alkyl group and said $C_{1-3}$alkyl is optionally substituted with 1 halogen; —$C_{1-6}$alkyl-S$(O)_2$—O-phenyl wherein said phenyl is optionally substituted with 1 $C_{1-3}$alkyl group and said $C_{1-3}$alkyl is optionally substituted with 1 halogen; C(O)—$N(R^d)_2$; and C(O)—O—$C_{1-6}$alkyl optionally substituted with 1 halogen;

$R^{1B}$ is selected from the group consisting of OH; —$C_{1-6}$alkyl optionally substituted with 1 halogen or OH group; —$C_{1-6}$alkyl-O—S$(O)_2$-phenyl wherein said phenyl is optionally substituted with 1 $C_{1-3}$alkyl group and said $C_{1-3}$alkyl is optionally substituted with 1 halogen; —$C_{1-6}$alkyl-S$(O)_2$—O-phenyl wherein said phenyl is optionally substituted with 1 $C_{1-3}$alkyl group and said $C_{1-3}$alkyl is optionally substituted with 1 halogen; C(O)—$N(R^4)_2$; and C(O)—O—$C_{1-6}$alkyl optionally substituted with 1 halogen; and $R^{1C}$ is selected from the group consisting of hydrogen; OH; —$C_{1-6}$alkyl optionally substituted with 1 halogen or OH group; —$C_{1-6}$alkyl-O—S$(O)_2$-phenyl wherein said phenyl is optionally substituted with 1 $C_{1-3}$alkyl group and said $C_{1-3}$alkyl is optionally substituted with 1 halogen; —$C_{1-6}$alkyl-S$(O)_2$—O-phenyl wherein said phenyl is optionally substituted with 1 $C_{1-3}$alkyl group and said $C_{1-3}$alkyl is optionally substituted with 1 halogen; C(O)—$N(R^4)_2$; and C(O)—O—$C_{1-6}$alkyl optionally substituted with 1 halogen.

6. The compound of claim 1, wherein:

$R^{1A}$ is selected from the group consisting of —$C_{1-6}$alkyl optionally substituted with 1 halogen or OH group; C(O)—$N(R^4)_2$; and C(O)—O—$C_{1-6}$alkyl optionally substituted with 1 halogen;

$R^{1B}$ is selected from the group consisting of —$C_{1-6}$alkyl optionally substituted with 1 halogen or OH group; C(O)—$N(R^d)_2$; and C(O)—O—$C_{1-6}$alkyl optionally substituted with 1 halogen; and $R^{1C}$ is selected from the group consisting of hydrogen; —$C_{1-6}$alkyl optionally substituted with 1 halogen or OH group; C(O)—$N(R^4)_2$.

7. The compound of claim 1, wherein:

$R^{1A}$ is selected from OH; —$C_{1-3}$alkyl optionally substituted with 1, 2, or 3 halogen or OH groups; C(O)—N$(H)_2$; or C(O)—O—$C_{1-3}$alkyl;

$R^{1B}$ is selected from OH; —$C_{1-3}$alkyl optionally substituted with 1, 2, or 3 halogen or OH groups; C(O)—N$(H)_2$; or C(O)—O—$C_{1-3}$alkyl; and $R^{1C}$ is selected from hydrogen; OH; —$C_{1-3}$alkyl optionally substituted with 1, 2, or 3 halogen or OH groups; C(O)—N$(H)_2$; or C(O)—O—$C_{1-3}$alkyl.

8. The compound of claim 1, wherein $R^3$ is selected from the group consisting of halogen and —$OC_{1-6}$alkyl optionally substituted with 1 halogen.

9. The compound of claim 1, wherein A has formula (IA).

10. The compound of claim 1, wherein $A_1$ and $A_4$ are CH, or wherein $A_1$ is N and $A_4$ is CH.

11. The compound of claim 1, wherein at least two of $B_1$, $B_2$, and $B_3$ are selected from the group consisting of CH and $CR^3$.

12. The compound of claim 1, wherein:

each $R^2$ is independently selected from the group consisting of halogen; OH; CN; $C_{1-6}$alkyl optionally substituted with 1, 2, or 3 halogen or OH groups; O—$C_{1-6}$alkyl optionally substituted with 1, 2, or 3 halogen or OH groups; $C(O)C_{1-6}$alkyl optionally substituted with 1, 2, or 3 halogen; C(O)—O—$C_{1-6}$alkyl optionally substituted with 1, 2, or 3 halogen; —$N(R^a)$C(O)H; —$N(R^a)C(O)C_{1-6}$alkyl optionally substituted with 1, 2, or 3 halogen; —C(O)$N(R^g)_2$; —$C_{1-6}$alkylC(O)$N(R^g)_2$; and —$(OCH_2CH_2)_p$—$R^f$.

13. The compound of claim 1, wherein $R^2$ is independently selected from the group consisting of OH and O—$C_{1-6}$alkyl optionally substituted with 1, 2, or 3 halogen or OH groups.

14. A compound selected from the group consisting of compounds (1)-(33); pharmaceutically acceptable salts, esters, ester salts, amides, amide salts, carbamate, or carbamate salts thereof; and compounds (1)-(33) or pharmaceutically acceptable salts, esters, ester salts, amides, amide salts, carbamate, or carbamate salts thereof containing one or more radioisotopes selected from $^{3}H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ or 131I:

(1) 1-[5-(6-methoxy-1,3-benzothiazol-2-yl)pyridin-2-yl]piperidin-3-ol;

(2) (3R)-1-[5-(6-methoxy-1,3-benzothiazol-2-yl)pyridine-2-yl]pyrrolidin-3-ol;

(3) (3S)-1-[5-(6-methoxy-1,3-benzothiazol-2-yl)pyridine-2-yl]pyrrolidin-3-ol;

(4) 2-{2-fluoro-6-[3-(hydroxymethyl)azetidin-1-yl]pyridine-3-yl}-1H-indol-5-ol;

(5) 2-{2-fluoro-6-[3-(hydroxyethyl)azetidin-1-yl]pyridine-3-yl}-1H-indol-5-ol;

(6) 2-{2-fluoro-6-[(3R)-3-hydroxypiperidin-1-yl]pyridine-3-yl}-1H-indol-5-ol;

(7) 2-{2-fluoro-6-[(3S)-3-hydroxypiperidin-1-yl]pyridine-3-yl}-1H-indol-5-ol;

(8) (3R,4R)-1-[5-(6-methoxy-1,3-benzothiazol-2-yl)pyridine-2-yl]piperidine-3,4-diol;

(9) (3R,4S)-1-[5-(6-methoxy-1,3-benzothiazol-2-yl)pyridine-2-yl]piperidine-3,4-diol;

(10) (3S,4R)-4-(Hydroxymethyl)-1-[5-(6-methoxy-1,3-benzothiazol-2-yl)pyridin-2-yl]piperidin-3-ol;

(11) (3S,4S)-4-(Hydroxymethyl)-1-[5-(6-methoxy-1,3-benzothiazol-2-yl)pyridine-2-yl]piperidin-3-ol;

(12) (3R,5S)-1-[5-(6-methoxy-1,3-benzothiazol-2-yl) pyridine-2-yl]piperidine-3,5-diol;

(13) (3S,5S)-1-[5-(6-methoxy-1,3-benzothiazol-2-yl) pyridine-2-yl]piperidine-3,5-diol;

(14) 4-(Hydroxymethyl)-1-[5-(6-methoxy-1,3-benzothiazol-2-yl)pyridin-2-yl]piperidine-4-ol;

(15) (3R,4R)-1-[6-fluoro-5-(5-hydroxy-1H-indol-2-yl) pyridin-2-yl]piperidine-3,4-diol;

(16) (3R,4S)-1-[6-fluoro-5-(5-hydroxy-1H-indol-2-yl) pyridine-2-yl]piperidine-3,4-diol;

(17) 2-{2-fluoro-6-[(3S,4R)-3-hydroxy-4(hydroxymethyl)piperidin-1-yl]pyridin-3-yl}-1H-indol-5-ol;

(18) 2-{2-fluoro-6-[(3S,4S)-3-hydroxy-4-(hydroxymethyl) piperidin-1-yl]pyridin-3-yl}-1H-indol-5-ol;

(19) (3S,5S)-1-[6-fluoro-5-(5-hydroxy-1H-indol-2-yl) pyridin-2-yl]piperidine-3,5-diol;

(20) (3R,5S)-1-[6-fluoro-5-(5-hydroxy-1H-indol-2-yl) pyridin-2-yl]piperidine-3,5-diol;

(21) 2-{2-fluoro-6-[4-hydroxy-4-(hydroxymethyl) piperidin-1-yl]pyridin-3-yl}-1H-indol-5-ol;

(22) (3S,4R)-1-[5-(6-methoxy-1,3-benzothiazol-2-yl) pyridin-2-yl]piperidine-3,4-diol;

(23) (3R,4S)-4-(Hydroxymethyl)-1-[5-(6-methoxy-1,3-benzothiazol-2-yl)pyridin-2-yl]piperidin-3-ol;

(24) (3R,5R)-1-[5-(6-methoxy-1,3-benzothiazol-2-yl) pyridine-2-yl]piperidine-3,5-diol;

(25) 2-{2-fluoro-6-[(3R,4S)-3-hydroxy-4-(hydroxymethyl) piperidin-1-yl]pyridine-3-yl}-1H-indol-5-ol;

(26) 2-{6-[(3R)-3-Hydroxypiperidin-1-yl]pyridin-3-yl}-1H-indol-5-ol;

(27) (3R)-1-{5-[5-(2-fluoroethoxy)-1H-indol-2-yl]pyridine-2-yl}piperidin-3-ol;

(28) (3R)-1-[5-(5-{2-[2-(2-fluoroethoxy)ethoxy]ethoxy}-1H-indol-2-yl)pyridine-2-yl]piperidin-3-ol;

(29) 2-{2-[(3R)-3-Hydroxypiperidin-1-yl]pyrimidin-5-yl}-1H-indol-5-ol;

(30) (3R)-1-{5-[5-(2-fluoroethoxy)-1H-indol-2-yl]pyrimidin-2-yl}piperidin-3-ol;

(31) (3R)-1-[5-(5-{2-[2-(2-fluoroethoxy)ethoxy]ethoxy}-1H-indol-2-yl)pyrimidin-2-yl]piperidin-3-ol;

(32) methyl 1-[6-fluoro-5-(5-hydroxy-1H-indol-2-yl) pyridin-2-yl]azetidine-3-carboxylate; and

(33) ($^3H_3$)methyl 1-[6-fluoro-5-(5-hydroxy-1H-indol-2-yl)pyridine-2-yl]azetidine-3-carboxylate.

15. A pharmaceutical composition comprising:

a compound according to claim 1;

a pharmaceutically suitable carrier; and optionally, an additional active ingredient.

16. A method for detecting tau deposits in a subject, the method comprising:

contacting a sample from the subject, or a specific body part or body area of the subject with a compound according to claim 1; and allowing the compound to bind to tau deposits to form a compound/tau deposits complex; and detecting the formation of the compound/tau deposits complex; and correlating a presence or absence of the compound/tau deposits complex in the sample or specific body part or area with a presence or absence of tau deposits in the subject.

17. A method of diagnosing or monitoring disease progression in a patient, the method comprising:

administering to a patient a compound according to claim 1;

allowing the compound to distribute into a tissue of interest of the subject;

imaging the tissue of interest; and comparing a level of binding of the compound to the tissue of interest with a normal or control level of binding, whereby an increase in binding of the compound to the tissue of interest compared to the normal or control level of binding indicates that the subject is suffering from or is at risk of developing a disorder associated with tau deposits.

18. The method of claim 17, wherein the compound comprises one or more radioisotopes selected from $^3H$, $^{11}C$, $^{13}C$, $^{14}C$, $^{13}N$, $^{15}O$, $^{18}F$, $^{19}F$, $^{75}Br$, $^{76}Br$, $^{120}I$, $^{123}I$, $^{125}I$ or $^{131}I$.

19. The method of claim 17, further comprising detecting the compound in the tissue of interest by radiosontigraphy, assays, chemiluminescence, electrochemiluminescence, autoradiography, near infrared luminescence, fluorescence, spectroscopy, liquid scintillation counting, gamma imaging, scintigraphy, magnetic resonance imaging (MRI), magnetic resonance spectroscopy (MRS), positron emission spectroscopy (PET), single-photon emission computed tomography (SPECT), or computed tomography (CT scan).

20. The method of claim 17, wherein the disease is selected from the group consisting of Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugilistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.Ile383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Straussler-Scheinker with tau mutations in LRRK2, SLC9A6-related mental retardation, and white matter tauopathy with globular glial inclusions.

21. A method for treating a condition associated with a disease or disorder associated with tau deposits in a mammal, the method comprising administering to the mammal having the condition a therapeutically effective amount of a compound according to claim 1.

22. The method of claim 21, wherein the disease or disorder is selected from the group consisting of Alzheimer's disease, corticobasal degeneration, Pick's disease, progressive supranuclear palsy, Parkinson's disease, Creutzfeldt-Jacob disease, familial Alzheimer's disease, argyrophilic grain disease, prion protein cerebral amyloid angiopathy, traumatic brain injury, amyotrophic lateral sclerosis, frontotemporal dementia and Parkinsonism linked to chromosome 17, postencephalitic Parkinsonism, Guadeloupean parkinsonism, globular glial tauopathies, ageing-related tau astrogliopathy, Parkinsonism-dementia complex of Guam, Niemann-Pick disease type C, myotonic dystrophy, inclusion-body myositis, chronic traumatic encephalopathy, Down's syndrome, Gerstman-Sträussler-Scheinker syndrome, British dementia, familial Danish dementia, dementia pugilistica, tangle predominant senile dementia, Huntington's disease, Lewy body disorders, Prion disease, subacute sclerosing panencephalitis, subacute sclerosing panencephalitis, diffuse neurofibrillary tangles with calcification, neurodegeneration with brain iron accumulation, mutation affecting the sodium/proton exchanger, cerebrotendinous xanthomatosis with the c.379C>T (p.R127W) mutation in the CYP27A1 gene, TARDBP mutation p.Ile383Val associated with semantic dementia, non-Guamanian motor neuron disease with neurofibrillary tangles, argyrophilic grain disease, Hallervorden-Spatz disease, multiple system atrophy, pallido-ponto-nlgral degeneration, progressive subcortical gliosis, tangle only dementia, myotonic dystrophy, tau panencephalopathy, AD-like with astrocytes, Gerstmann-Straussler-Scheinker with tau mutations in LRRK2, SLC9A6-related mental retardation, and white matter tauopathy with globular glial inclusions.

* * * * *